(12) United States Patent
Paik et al.

(10) Patent No.: US 11,639,931 B2
(45) Date of Patent: May 2, 2023

(54) APPARATUSES AND METHODS FOR DETECTING MOLECULES AND BINDING ENERGY

(71) Applicant: Analog Devices, Inc., Wilmington, MA (US)

(72) Inventors: Kee-Hyun Paik, Corte Madera, CA (US); Kaveh M. Milaninia, San Jose, CA (US); Kilian Dill, San Francisco, CA (US)

(73) Assignee: Analog Devices, Inc., Wilmington, MA (US)

( * ) Notice: Subject to any disclaimer, the term of this patent is extended or adjusted under 35 U.S.C. 154(b) by 499 days.

(21) Appl. No.: 16/559,304

(22) Filed: Sep. 3, 2019

(65) Prior Publication Data

US 2020/0326297 A1     Oct. 15, 2020

Related U.S. Application Data

(63) Continuation of application No. 15/662,168, filed on Jul. 27, 2017, now Pat. No. 10,444,179, which is a
(Continued)

(51) Int. Cl.

| | | |
|---|---|---|
| *G01N 33/543* | (2006.01) | |
| *G01N 33/487* | (2006.01) | |
| *G01N 27/327* | (2006.01) | |
| *G01N 21/64* | (2006.01) | |
| *G01N 21/552* | (2014.01) | |

(52) U.S. Cl.
CPC ..... *G01N 33/54373* (2013.01); *G01N 21/553* (2013.01); *G01N 21/6428* (2013.01); *G01N 27/3272* (2013.01); *G01N 33/487* (2013.01); *G01N 33/5438* (2013.01);
(Continued)

(58) Field of Classification Search
CPC ............. G01N 27/3272; G01N 21/553; G01N 21/6428; G01N 33/487; G01N 33/54353; G01N 33/54373; G01N 33/5438; G01N 33/48721; G01N 2021/6439
See application file for complete search history.

(56) References Cited

U.S. PATENT DOCUMENTS 5,363,697 A    11/1994  Nakagawa
5,445,970 A     8/1995  Rohr
(Continued)

FOREIGN PATENT DOCUMENTS

EP           2196796 A1    6/2010
KR      20070080098    *   8/2007
(Continued)

OTHER PUBLICATIONS

Allen, et al. Detection of antigen-antibody binding events with the atomic force microscope. Biochemistry. 36 (1997):7457-7463.
(Continued)

*Primary Examiner* — Melanie Brown
(74) *Attorney, Agent, or Firm* — ArentFox Schiff LLP

(57) ABSTRACT

The present disclosure provides apparatuses and methods for analyzing the presence of a target analyte. The apparatuses and methods of the present disclosure can be operated in a multiplexed format to perform various assays of clinical significance.

19 Claims, 48 Drawing Sheets

Specification includes a Sequence Listing.

Related U.S. Application Data continuation-in-part of application No. 15/451,133, filed on Mar. 6, 2017, now Pat. No. 9,816,988.

(60) Provisional application No. 62/373,241, filed on Aug. 10, 2016, provisional application No. 62/373,158, filed on Aug. 10, 2016.

(52) U.S. Cl.
CPC .. *G01N 33/54353* (2013.01); *G01N 33/48721* (2013.01); *G01N 2021/6439* (2013.01)

(56) References Cited

U.S. PATENT DOCUMENTS

| | | | |
|---|---|---|---|
| 5,445,971 | A | 8/1995 | Rohr |
| 5,831,070 | A | 11/1998 | Pease et al. |
| 5,925,525 | A | 7/1999 | Fodor et al. |
| 5,992,226 | A | 11/1999 | Green et al. |
| 6,086,821 | A | 7/2000 | Lee |
| 6,180,418 | B1 | 1/2001 | Lee |
| 6,428,959 | B1 | 8/2002 | Deamer |
| 6,780,584 | B1 | 8/2004 | Edman et al. |
| 7,736,889 | B2 | 6/2010 | Rife et al. |
| 7,744,737 | B1 | 6/2010 | James et al. |
| 8,324,914 | B2 | 12/2012 | Chen et al. |
| 8,592,225 | B2 | 11/2013 | Ronaghi et al. |
| 8,810,787 | B2 | 8/2014 | Van Dorpe et al. |
| 9,188,560 | B2 | 11/2015 | Liu et al. |
| 9,816,988 | B1 | 11/2017 | Paik et al. |
| 9,981,273 | B2 | 5/2018 | Javanmard et al. |
| 10,444,179 | B2 | 10/2019 | Paik et al. |
| 2003/0064699 | A1 | 4/2003 | Olsen |
| 2004/0038426 | A1 | 2/2004 | Manalis |
| 2004/0045829 | A1* | 3/2004 | Ingenhoven ..... G01N 27/44704 204/615 |
| 2008/0035180 | A1 | 2/2008 | Mutharasan et al. |
| 2009/0109441 | A1 | 4/2009 | Hartman |
| 2009/0205977 | A1 | 8/2009 | Shew et al. |
| 2009/0283700 | A1 | 11/2009 | Ohtsuka |
| 2010/0152057 | A1 | 6/2010 | Lieber et al. |
| 2010/0243449 | A1 | 9/2010 | Oliver |
| 2010/0327874 | A1 | 12/2010 | Liu et al. |
| 2011/0031123 | A1 | 2/2011 | Schulze et al. |
| 2011/0036719 | A1 | 2/2011 | Neyts et al. |
| 2011/0162963 | A1 | 7/2011 | Hibbs et al. |
| 2013/0048499 | A1 | 2/2013 | Mayer et al. |
| 2013/0203608 | A1 | 8/2013 | Shim et al. |
| 2013/0264207 | A1 | 10/2013 | Ju et al. |
| 2014/0034497 | A1 | 2/2014 | Davis et al. |
| 2014/0090981 | A1 | 4/2014 | Paik et al. |
| 2014/0106472 | A1 | 4/2014 | Ervin et al. |
| 2014/0134618 | A1 | 5/2014 | Kokoris et al. |
| 2014/0158540 | A1 | 6/2014 | Ohura |
| 2014/0360890 | A1 | 12/2014 | Mutharasan et al. |
| 2015/0204873 | A1 | 7/2015 | Ervin et al. |
| 2015/0246146 | A1 | 9/2015 | Agnew et al. |
| 2015/0377830 | A1 | 12/2015 | Baldauf et al. |
| 2016/0003798 | A1 | 1/2016 | Paik et al. |
| 2017/0097332 | A1 | 4/2017 | Paik et al. |
| 2017/0356904 | A1 | 12/2017 | Paik et al. |

FOREIGN PATENT DOCUMENTS

| | | |
|---|---|---|
| WO | WO-9309250 A1 | 5/1993 |
| WO | WO-03100012 A2 | 12/2003 |
| WO | WO-2008102120 A1 | 8/2008 |
| WO | WO-2009035647 A1 | 3/2009 |
| WO | WO-2009155423 A1 | 12/2009 |
| WO | WO-2010004273 A1 | 1/2010 |
| WO | WO-2011027379 A1 | 3/2011 |
| WO | WO-2013154999 A2 | 10/2013 |
| WO | WO-2013191793 A1 | 12/2013 |
| WO | WO-2015100170 A1 | 7/2015 |
| WO | WO-2015110777 A1 | 7/2015 |
| WO | WO-2015196148 A1 | 12/2015 |
| WO | WO-2016059375 A1 | 4/2016 |
| WO | WO-2016160131 A1 | 10/2016 |
| WO | WO-2018031247 A1 | 2/2018 |

OTHER PUBLICATIONS

Chilkoti, A., et al., The relationship between ligand-binding thermodynamics and protein-ligand interaction forces measured by atomic force microscopy. Biophysical Journal. 1995; 69(5):2125-2130.

Co-pending U.S. Appl. No. 16/530,040, filed Aug. 2, 2019.

Dammer, et al. Specific antigen/antibody interactions measured by force microscopy. Biophysical Journal. 70 (1996): 2437-2441.

Drummond, et al. Electrochemical DNA sensors. Nature Biotechnology. 21 (2003): 1192-1199.

Dudko, O.K., et al., Extracting kinetics from single-molecule force spectroscopy: nanopore unzipping of DNA hairpins. Biophysical Journal. 2007; 92(12): 4188-4195.

Dunbar. Applications of luminex® xMAP™ technology for rapid, high-throughput multiplexed nucleic acid detection. Clinica Chimica Acta. 363 (2006): 71-82.

Ekins, et al. Development of microspot multi-analyte ratiometric immunoassay using dual fluorescent-labelled antibodies. Analytica Chimica Acta. 227 (1989): 73-96.

Ekins, et al. Multispot, Multi-analyte immunoassay. Journal of Pharmaceutical & Biomedical Analysis, 7.2 (1989): 155-168.

Emaminejad, et al. Multiplexed actuation using ultra dielectrophoresis for proteomics applications: A comprehensive electrical and electrothermal design methodology. Lab on a chip. 14 (2014): 2105.

Eric, et al. Antibacterial drug discovery in the resistance era. Nature. 529 (2016): 336-343.

European search report with written opinion dated Sep. 13, 2018 for EP Application No. 16773620.6.

European search report with written opinion dated Dec. 15, 2017 for EP Application No. 15810443.0.

Evans, E. et al., Dynamic strength of molecular adhesion bonds. Biophysical Journal. 1997; 72(4): 1541-1555.

Falk, et al. Unbinding forces of single antibody-antigen complexes correlate with their thermal dissociation rates. Proceedings of the National Academy of Sciences of the United States of America. 97 (2000): 9972-9977.

Fingerova, et al. Antioxidant capacity of seminal plasma measured by TAS randox. Biomedical papers of the Medical Faculty of the University Palacky, Olomouc, Czechoslovakia. 151 (2007): 37-40.

Fletcher, et al. Plasma cytokines in women with chronic fatigue syndrome. Journal of translational medicine. 7 (2009): 96.

Florin, E.L., et al. Adhesion Forces between Individual ligand-receptor pairs. Science. 1994;264 (5157); 415-417.

Frances,. Perspective on optical biosensors and integrated sensor systems. Analytical Chemistry. 81 (2009): 519-526.

Gong, et al. Simple method to prepare oligonucleotide-antibodies and its application to multiplex protein detection in single cells. Bioconjugate Chemsitry. 27 (2014): 217-225.

Houser,. Bio-rad's bio-plex® suspension array system, xMAP technology overview. Archives of Physiology and Biochemistry. 118 (2012): 192-196.

Howorka, et al. Sequence-specific Detection of Individual DNA Strands Using Engineered Nanopores. Nat Biotechnol. Jul. 2001;19(7):636-639. doi: 10.1038/90236.

International search report with written opinion dated Aug. 8, 2016 for PCT/US2016/017181.

International search report with written opinion dated Sep. 14, 2015 for PCT/US2015/036800.

International search report with written opinion dated Oct. 6, 2017 for PCT/US2017/044252.

Iqbal, S.M. et al. (2007) "Solid-state nanopore channels with DNA selectivity," Nature Nanotechnology 2(4):243-248.

Juncker, D. et al., Cross-reactivity in antibody microarrays and multiplexed sandwich assays: shedding light on the dark side of multiplexing. Current Opinion in Chemical Biology. 2014; 18:29-37.

(56) References Cited

OTHER PUBLICATIONS

Kahng,. The ITRS design technology and system drivers roadmap: Process and Status. DAC. (2013): 1-6.
Katsanis, et al. Molecular genetic testing and the future of clinical genomics. Nature reviews. Genetics. 14 (2013): 415-426.
Kazane, et al. Site-specific DNA-antibody conjugates for specific and sensitive immune-PCR. Proceedings National Academy of Sciences. 109 (2012): 3731-3736.
Kee-Hyun, et al. Apparatuses and Methods for Determining Analyte Charge. 2017, 20170097332.
Kee-Hyun, et al. Flow Control Method and Apparatuses. Life Science Weekly. 2014; U.S. Appl. No. 14/043,710:4352.
Keyser, et al. Direct force measurements on DNA in a solid-state nanopore. Nature Physics, vol. 2, Jul. 2006, pp. 473-477.
Lee, et al. Implementation of force differentiation in the immunoassay. Analytical Biochemistry. 287 (2000): 261-271.
Lee, G. U., et al., Sensing discrete streptavidin biotin interactions with atomic-force microscopy. Langmuir. 1994; 10(2): 354-357.
Liu, et al. Effect of electrodiffusion current flow on electrostatic screening in aqueous pores. Journal of Applied Physics. 103 (2008): 4.
Liu, et al. Targeting alpha-fetoprotein (AFP)-MHC complex with CAR T-cell therapy for liver cancer. Clinical Cancer Research. 23 (2017): 478-488.
Mary, et al. Pharmacogenomics in the clinic. Nature. 526 (2015): 343-350.
Mastrangelo, et al. The potential and challenges of nanopore sequencing. Nature Biotechnology. 26 (2008): 1146-1153.
Mehdi, et al. Use of negative dielectrophoresis for selective elution of protein-bound particles. Analytical Chemistry. 84 (2012): 1432.
Michael, et al. Mfold web server for nucleic acid folding and hybridization prediction. Nucleic Acids Research. 31 (2003): 3406-3415.
Mostafa, et al. Array-Based Bioactivated Nanopore Devices. (2013).
Neuman, et al. Single-molecule force spectroscopy: Optical tweezers, magnetic tweezers and atomic force microscopy. Nature Methods. 5.6 (2008): 491-505.
Nguyen, G. et al. (201 0) "DNA Strands Attached Inside Single Conical Nanopores: Ionic Pore Characteristics and Insight into DNA Biophysics," J Membrane Bioi. 239(1-2): 105-113.
Notice of allowance dated Jun. 5, 2019 for U.S. Appl. No. 15/662,168.
Notice of Allowance dated Aug. 3, 2017 for U.S. Appl. No. 15/451,133.
Notice of Allowance dated Oct. 19, 2017 for U.S. Appl. No. 15/451,133.
Office action dated Feb. 6, 2019 for U.S. Appl. No. 15/673,653.
Office action dated Mar. 14, 2017 for U.S. Appl. No. 15/382,364.
Office action dated Apr. 30, 2018 for U.S. Appl. No. 15/382,364.
Office Action dated May 24, 2017 for U.S. Appl. No. 15/382,364.
Office action dated Jun. 20, 2018 for U.S. Appl. No. 15/673,653.
Office action dated Oct. 3, 2019 for U.S. Appl. No. 15/382,364.
Office action dated Nov. 2, 2017 for U.S. Appl. No. 15/382,364.
Office action dated Dec. 14, 2018 for U.S. Appl. No. 15/382,364.
Office action dated Dec. 28, 2018 for U.S. Appl. No. 15/662,168.
Paik, et al. Apparatuses and Methods for Detecting Molecules and Binding Energy. 2017,U.S. Pat. No. 9,816,988B1.
Paik, et al. Control of DNA capture by nanofluidic transistors. ACS nano. 6.8 (2012): 6767-6775.
Prescher, et al. Copper-free click chemistry for dynamic in vivo imaging. Proceedings of the National Academy of Sciences. 104 (2007): 16793-16797.
Rothberg, et al. An integrated semiconductor device enabling non-optical genome sequencing. Nature. 475 (2011): 348-352.
Sano, et al. Immuno-PCR: Very sensitive antigen detection by means of specific antibody-DNA conjugates. Science. 258 (1992): 120-122.
Schwenk, et al. Toward next generation plasma profiling via heat-induced epitope retrieval and array-based assays. Molecular & cellular proteomics : MCP. 9 (2010): 2497-2507.
Sheth, et al. Point of care testing for improving risk-benefit ratio of aspirin and warfarin. Molecular cytogenetics. 7 (2014): 154.
Smith, et al. Measurement of protein using bicinchoninic acid. Anal. Biochem. 150 (1985): 76-85.
Spindel, et al. Evaluation of optical detection platforms for multi-plexed detection of proteins and the need for point-of-care biosensors for clinical use. Sensors (Basel, Switzerland). 14 (2014): 22313-22341.
Tabard-Cossa, et al. Single-molecule bonds characterized by solid-state nanopore force spectroscopy. ACS nano. 3 (2009): 3009.
ThermoFisher. IL-8 Human Matched Antibody Pair. Catalog No. CHC1303. 3 pages. Retrieved online at https://www.thermofisher.com/order/catalog/product/CHC1303.
ThermoFisher. SiteClick™ Antibody Azido Modification Kit— User Guide. Catalog No. S20026. Pub. No. MAN0017078. Rev. A.0. May 11, 2017. 12 pages.
ThermoFisher. SiteClick™ Antibody Labeling System. 3 pages. Retrieved online at https://www.thermofisher.com/us/en/home/life-science/cell-analysis/labeling-chemistry/protein-and-antibody-chemical-labeling/antibody-protein-labeling-kits/siteclick-labeling.html.
Tighe, et al. ELISA in the multiplex era: Potentials and pitfalls. Proteomics—Clinical Applications. 9 (2015): 406-422.
Tropini, et al. Multi-nanopore force spectroscopy for DNA analysis. Biophysical Journal. 92 (2007): 1632-1637.
Van, et al. A covalent and cleavable antibody-DNA conjugation strategy for sensitive protein detection via immune-PCR. Scientific Reports. 6.22675 (2016): 2045-2322.
Wilco, et al. Simultaneous detection of 15 human cytokines in a single sample of stimulated peripheral blood mononuclear cells. Clinical and Diagnostic Laboratory Immunology. 10 (2003): 133-139.
Wong, et al. Direct force measurements of the streptavidin-biotin interaction. Biomolecular Engineering. 16 (1999): 45-55.
Yan, et al. A universal approach to prepare reagents for DNA-assisted protein analysis. Plos One. 9(2014): 1-8.
Yang, et al. Electro-Diffusion Enhanced Bio-Molecule Charge Detection using Electrostatic Interaction. 2015.
Yang, et al. Overcoming the screening-induced performance limits of nanowire biosensors: A simulation study on the effect of electro-diffusion flow. IEDM. (2008): 1-4.
You, et al. 3-(4-Carboxybenzoyl)quinoline-2-carboxaldehyde, a reagent with broad dynamic range for the assay of proteins and lipoproteins in solution. Anal Biochem. 244 (1997): 277-282.

\* cited by examiner

```
                              SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tcatctccta gtagataaaa                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tcatctcgta gtagataaaa                                                     20

<210> SEQ ID NO 3
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atctactagg agatgaatag actaccaaca ggagcaccgg aacccatgta tgactcccag         60
taagttaaag ttaggtcagt cgtgtaaccg tagtataga                                99

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcacggtagc ataaggtgca cgttaccttg attcccgtcc                               40

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccaaaccaac cacc                                                           14
```

US 11,639,931 B2

APPARATUSES AND METHODS FOR DETECTING MOLECULES AND BINDING ENERGY

CROSS-REFERENCE

This application is continuation application of U.S. application Ser. No. 15/662,168, filed Jul. 27, 2017, which is a continuation-in-part application of U.S. application Ser. No. 15/451,133, Mar. 6, 2017, now U.S. Pat. No. 9,816,988, which claims the benefit of U.S. Provisional Patent Application Ser. No. 62/373,158, filed Aug. 10, 2016, and U.S. Provisional Patent Application Ser. No. 62/373,241, filed Aug. 10, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 4, 2020, is named 48109_710_302_SL.txt and is 1,646 bytes in size.

BACKGROUND

Various types of molecules can recognize other molecules by the formation of multiple (numbers and/or types of) non-covalent bonds (e.g., van der Waals, hydrogen bonds, coulombic attractions and hydrophobic bonds), which can be combined in a particular spatial orientation. These molecular recognition interactions can be reversible and of moderate to high specificity. Examples of such molecular interactions include antibody-antigen interactions and nucleic acid hybridizations. Such interactions are important for biology and several mature and developing industries, such as medical diagnostics, therapeutics, biotechnology, agriculture, fuel and chemical production, defense, environmental monitoring, food and food safety to name a few.

SUMMARY

Recognized herein is the need for new and improved sensors and methods for detecting the presence of molecular interactions and for measuring the force associated with molecular interactions. The present disclosure provides such sensors and methods for using the sensors. Without limitation, the apparatuses, systems and methods of the present disclosure have advantages in differentiating between specific (e.g., strong) and non-specific (e.g., weak) molecular interactions and therefore, can distinguish between false positive and true positive signals. The present apparatuses and methods may be suitable for multiplexing (e.g., performing 5, 10, $10^2$, $10^3$, $10^4$, $10^5$, $10^6$ or more measurements in parallel) and directly using complex mixtures having two or more analytes such as biological fluids (e.g., blood) or environmental samples. In some embodiments, the apparatuses and methods described herein can be used to measure the force associated with molecular interactions, spanning multiple orders of magnitude in strength (e.g., between about 1 piconewton (pN) and about 400 pN).

In an aspect, the present disclosure provides a method for detecting a target analyte. The method comprises (a) providing a sensor comprising a plurality of electrodes capable of applying an electric field to at least one surface that comprises a capture probe coupled thereto and in proximity to a sensing location; (b) contacting the at least one surface with a solution containing or suspected of containing a target analyte and a non-target analyte, under conditions sufficient to (i) permit the target analyte to couple to the at least one surface through a first non-covalent interaction, which first non-covalent interaction is with the capture probe, and (ii) permit the non-target analyte to couple to the at least one surface through a second non-covalent interaction; (c) using a first set of electrodes of the plurality of electrodes to apply a first electric field that is sufficient to disrupt the second non-covalent interaction between the non-target analyte and the at least one surface; (d) subsequent to (c), using a second set of electrodes of the plurality of electrodes to apply a second electric field that is sufficient to disrupt the first non-covalent interaction between the target analyte and the capture probe; and (e) detecting a signal indicative of (1) a presence or absence of the target analyte, or (2) a disruption of the first non-covalent interaction.

In some embodiments, the non-target analyte is charged, and the first electric field provides a force on the non-target analyte that is sufficient to disrupt the second non-covalent interaction. In some embodiments, the target analyte is charged, and applying the second electric field provides a force on the target analyte sufficient to disrupt the first non-covalent interaction.

In some embodiments, the method further comprises applying a third electric field that is sufficient to dissociate the capture probe from the at least one surface.

In some embodiments, the first electric field and the second electric field are applied by establishing a first voltage and a second voltage across the first set of electrodes and the second set of electrodes, respectively. In some embodiments, the second voltage is greater than the first voltage. In some embodiments, the first voltage and the second voltage are individual voltages of a continuously applied voltage changed over time. In some embodiments, the method further comprises increasing the first voltage to the second voltage at a rate of at least about 1 millivolt per second or over a period of time of less than about 1 second.

In some embodiments, the method further comprises detecting an additional signal indicative of (1) a presence or absence of the non-target analyte, or (2) a disruption of the second non-covalent interaction between the non-target analyte and the at least one surface. In some embodiments, the additional signal is detected before applying the second electric field.

In some embodiments, the target analyte is detected using a detectable tag. In some embodiments, the detectable tag is a fluorophore. In some embodiments, the detectable tag is coupled to a detectable antibody that binds to the target analyte.

In some embodiments, in (b), the second non-covalent interaction is with another capture probe coupled to the at least one surface.

In some embodiments, the first electric field is not sufficient to release the target analyte. In some embodiments, the first electric field and/or second electric field is stabilized using a bias stabilization unit. In some embodiments, the first electric field has a strength of less than about $10^9$ volts per meter (V/m). In some embodiments, the first electric field and/or the second electric field is applied without washing the at least one surface.

In some embodiments, the signal is indicative of a binding energy associated with the first non-covalent interaction between the target analyte and the capture probe. In some embodiments, the capture probe is a nucleic acid molecule. In some embodiments, the capture probe is an antibody. In some embodiments, the capture probe (e.g., nucleic acid molecule, antibody) is coupled to the at least one surface using a linker. In some embodiments, the linker is a NHS-PEG-maleimide linker. In some embodiments, the capture probe is coupled to the surface using a linker having a dibenzocyclooctyne (DIBO) group and a maleimide moiety.

In some embodiments, the signal is detected with a sensing unit operatively coupled to the sensing location. In some embodiments, the sensing unit is an optical sensing unit, and the signal is an optical signal. In some embodiments, the signal is detected substantially in real time.

In some embodiments, the first set of electrodes or the second set of electrodes comprises two or more electrodes. In some embodiments, the first set of electrodes is the second set of electrodes.

In an aspect, the present disclosure provides a system for detecting a target analyte. The system comprises a sensor comprising a plurality of electrodes capable of applying an electric field to at least one surface that comprises a capture probe coupled thereto and in proximity to a sensing location; a solution chamber in fluid communication with the at least one surface, wherein the solution chamber is configured to retain a solution containing or suspected of containing the target analyte and a non-target analyte, under conditions sufficient to (i) permit the target analyte to couple to the at least one surface through a first non-covalent interaction, which first non-covalent interaction is with the capture probe, and (ii) the non-target analyte to couple to the at least one surface through a second non-covalent interaction; and a controller operatively coupled to the plurality of electrodes, wherein the controller is programmed to: (i) use a first set of electrodes of the plurality of electrodes to apply a first electric field that is sufficient to disrupt the second non-covalent interaction between the non-target analyte and the at least one surface, (ii) subsequent to applying the first electric field, use a second set of electrodes of the plurality of electrodes to apply a second electric field that is sufficient to disrupt the first non-covalent interaction between the target analyte and the capture probe, and (iii) detect a signal indicative of (1) a presence or absence of the target analyte, or (2) a disruption of the first non-covalent interaction.

In some embodiments, the sensor is part of an array of sensors. In some embodiments, each sensor of the array of sensors is independently addressable.

In some embodiments, the sensor comprises a bias stabilization unit.

In some embodiments, the sensor further comprises a sensing unit operatively coupled to the controller, wherein the controller detects the signal using the sensing unit. In some embodiments, the sensing unit is an optical sensing unit, and the signal indicative of the presence of the target analyte is an optical signal.

In some embodiments, the first set of electrodes is the second set of electrodes.

In some embodiments, the capture probe comprises an antibody. In some embodiments, the capture probe comprises a nucleic acid. In some embodiments, the capture probe (e.g., nucleic acid, antibody) is coupled to the at least one surface using a linker. In some embodiments, the linker is an NHS-PEG-maleimide linker. In some embodiments, the capture probe is coupled to the at least one surface using a linker comprising a dibenzocyclooctyne (DIBO) group and a maleimide moiety.

In an aspect, the present disclosure provides a method for coupling a target molecule to a sensor surface. The method comprises (a) providing (i) the sensor surface comprising a thiol group, (ii) the target molecule comprising an azide group, and (iii) a linker molecule comprising a maleimide moiety and a strained triple bond; and (b) reacting the linker molecule with the sensor surface and the target molecule such that (i) the azide group of the target molecule and the strained triple bond of the linker molecule undergo cycloaddition, and (ii) the thiol group of the sensor surface forms a covalent bond with the maleimide moiety of the linker molecule, thereby coupling the target molecule to the sensor surface via the linker molecule. In some embodiments, the strained triple bond is part of a cyclooctyne ring. In some embodiments, the cyclooctyne ring is part of a dibenzocyclooctyne (DIBO) group.

In some embodiments, reacting the linker molecule with the sensor surface and the target molecule is not catalyzed by copper. In some embodiments, the linker molecule is reacted simultaneously with the sensor surface and the target molecule. In some embodiments, the linker molecule is reacted with the sensor surface prior to being reacted with the target molecule. In some embodiments, the linker molecule is reacted with the sensor surface subsequent to being reacted with the target molecule.

In some embodiments, the target molecule is a nucleic acid molecule. In some embodiments, the target molecule is an antibody. In some embodiments, the azide group of the antibody is not in proximity to a binding region of the antibody. In some embodiments, the azide group of the antibody is located in a constant region of the antibody. In some embodiments, the azide group of the antibody is not located in a variable region of the antibody.

In some embodiments, the azide group is added to the antibody at least in part by (a) removing terminal galactose residues of terminal N-acetylglucosamine (GlcNAc) residues using the enzyme beta-galactosidase and (b) incorporating a N-azidoacetylgalactosamine-tetraacylated (GalNAz) which contains the azide group into the antibody using a beta-galactosyltransferase (GalT), thereby adding the azide group to antibody.

In some embodiments, the sensor surface is part of a sensor that comprises a plurality of electrodes capable of applying an electric field. In some embodiments, the reacting in (b) is at an efficiency of at least about 5%, 10%, 20%, 30%, 40%, 50%, 60%, 70%, 80%, or 90%.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGS." herein), of which:

DETAILED DESCRIPTION

Figure 1A:
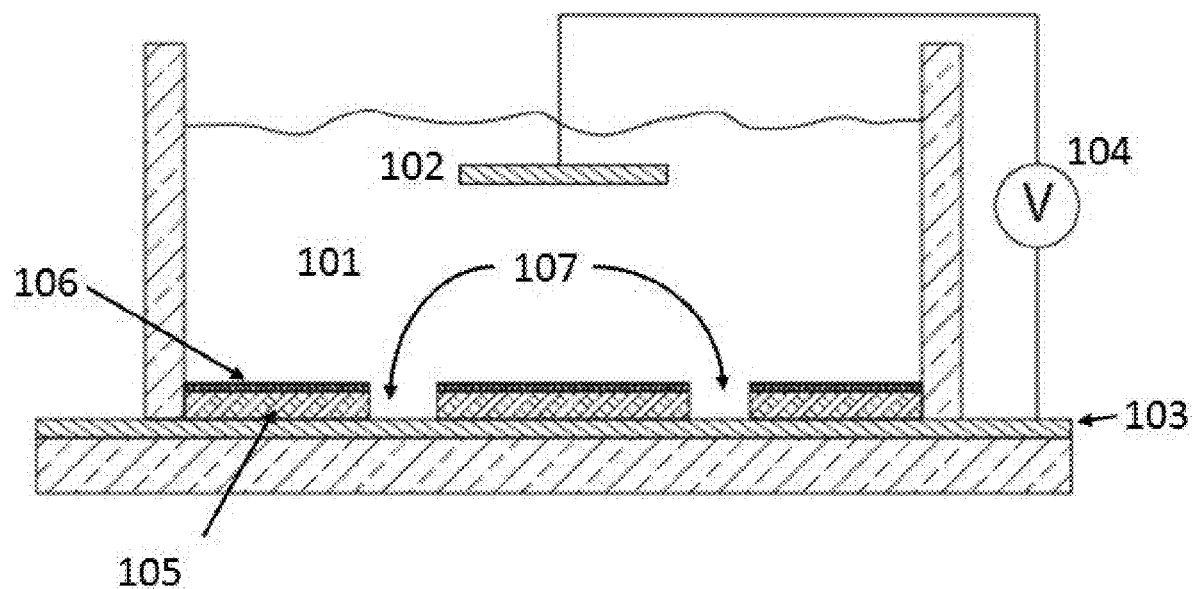
FIG. 1A shows an example of a cross-sectional profile view of an apparatus of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides methods and systems for detecting and/or analyzing a target analyte. Methods and systems provided herein may be used to detect a target analyte, such as a protein, small molecule or target nucleic acid molecule having a target sequence. This can be used to identify the target molecule (e.g., sequence), including, without limitation, identifying a genetic aberration in the sequence, such as a polymorphism, single nucleotide variant or gene fusion.

The term "analyte," as used herein, generally refers to a species of interest for detection. An analyte may be biological analyte, such as an nucleic acid molecule or protein. An analyte may be an atom or molecule. An analyte be a subunit of a larger unit, such as, e.g., a given sequence of a polynucleotide sequence or a sequence as part of a larger sequence.

An externally applied electric field in an aqueous solution can apply a force on a charged particle (e.g., molecule or analyte) in the solution. Such force on the charged particle (F) can be proportional to the applied electric field (E) and the net electric charge of the particle (q) according to the equation $F=qE$.

Using the linear relation among these parameters, the present method correlates the applied force to the input parameters (e.g., applied external biases). Provided herein is an apparatus that may utilize such force to perform a force spectroscopy and force differentiation assay. The assay can be performed on antigen-antibody bonds or used for nucleic acid analysis (e.g., single nucleotide polymorphism (SNP) analysis). In some cases, the binding force between the analyte and a capture probe can be from about 1 piconewton (pN) to about 400 pN.

Given an example of a charged particle having a charge of 100e− (e.g., equivalent to a nucleic acid with 100 bases), the external electric field strength used to disrupt some bonds of interest are shown as follows in Table 1.

TABLE 1

Electric field needed to disrupt bonds of interest (assuming 100e− of charge on the labeling molecule).

| Molecule | Force [pN] | Efield needed [V/m] |
|---|---|---|
| Streptavidin Biotin | 141 | 8.8E+06 |
| 14mer SNP (CCAAACCAACCACC) (SEQ ID NO: 5) | 178 | 1.1E+07 |
| 14mer SNP 1 base change $8^{th}$ C to G | 130 | 8.1E+06 |
| 14mer SNP 1 base change $8^{th}$ C to A | 133 | 8.3E+06 |
| Biotin-Antibiotin | 112 | 7.0E+06 |
| Ferritin-Antiferritin | 49 | 3.1E+06 |

The field strengths needed may be relatively large, which may be difficult to generate in an open structure. Therefore, the present apparatus employs (physical) confinement using (micro or nano-scale) structures to significantly boost the applied electric field strength. These structures are referred to herein as "field confinement features" and can include pores, channels, gaps and slits (e.g., orifices), as well as raised structures associated with a sensing surface. Nanopores are a type of field confinement feature which can physically confine translocation of molecules, enabling single molecule detection via blocking of the nanopore.

In some cases, an advantage of such physical confinement is the electrical confinement that comes with it. When designed with the orifice being the smallest feature, the orifice can dominate the electrical characteristics of the entire system. The potential drop (thus the electric field) can occur primarily near the orifice and less (to very little) elsewhere. When the orifice is small (e.g., micro or nano scale) such confinement can generate a large electric field with relatively low applied bias. For example, a synthetic nanopore on a 100 nm thick $SiN_x$ membrane can generate about 10,000,000 V/m of electric field across it with application of 1 V. The present disclosure encompasses any size, shape or arrangement of field confining features (e.g., orifices), including the embodiments shown in FIG. 1A, FIG. 1B and FIG. 1C.

By preparing a group of recognition molecules (e.g., capture probes) in advance, the present method can look for the presence of their respective target molecules (e.g., analytes) in a sample by observing the quantity and force by which the analytes bind to the capture probes. In some cases, the present method can look for the presence of a target molecule using a detection probe (e.g., labeled or labeling agent) to detect an analyte bound to a capture probe. An analyte can be bound directly to a capture probe or bound indirectly to a capture probe. An analyte that is bound indirectly to a capture probe may be bound via an intermediate molecule such as a molecular linker. The molecular linker can be covalently or non-covalently associated with the analyte. Examples of linkers include, but are not limited to, chemical compounds (e.g., polyethylene glycol), proteins (e.g., one of a protein-protein binding pair, e.g., biotin-avidin, or protein-binding partner pair), nucleic acids (e.g., a nucleic acid that is hybridizable to a capture probe comprising a nucleic acid or a nucleic acid of a nucleic acid-binding partner pair), or any combination of these. The present method of analyzing such molecular recognition (e.g., binding) events can be referred to as a binding assay.

Non-specific binding may present a challenge in existing binding assays. Other limitations of existing binding assays include an inability to multiplex the assay, inability to perform the assay on a micro or nano-scale (e.g., be densely integrated), and inability to generate sufficient forces. Examples of existing binding assays include, but are not limited to: enzyme-linked immunosorbent assay (ELISA); sandwich ELISA; proximity ligation assay (in situ PLA); force differentiation assays (as described in Juncker, D., S. Bergeron, et al. (2014) "Cross-reactivity in antibody microarrays and multiplexed sandwich assays: shedding light on the dark side of multiplexing." Current Opinion in Chemical Biology 18: 29-37); micropipettes used in conjunction with optical microscopy (as described in Evans, E. and K. Ritchie (1997) "Dynamic strength of molecular adhesion bonds." Biophysical Journal 72(4): 1541-1555); use of laminar fluid flow to generate physical force onto beads of certain sizes (as described in U.S. Pat. No. 7,736,889); ultrasound excitation used to agitate bound molecules (as described in U.S. Pat. No. 6,086,821); use of magnetic field to deliver the forces to intermolecular bonds (as described in U.S. Pat. Nos. 5,445,970; 5,445,971 and 6,180,418); use of dielectrophoresis (as described in U.S. Patent Application Publication No. 20140102901); use of atomic force microscopy (AFM) (as described in U.S. Pat. Nos. 5,363,697; 5,992,226; 5,992,226; Florin, E. L., V. T. Moy, et al. (1994) "Adhesion Forces between Individual Ligand-Receptor Pairs." Science 264(5157): 415-417; Lee, G. U., D. A. Kidwell, et al. (1994) "Sensing Discrete Streptavidin Biotin Interactions with Atomic-Force Microscopy." Langmuir 10(2): 354-357; Dammer, U., M. Hegner, et al. (1996) "Specific antigen/antibody interactions measured by force microscopy." Biophysical Journal 70(5): 2437-2441; Chilkoti, A., T. Boland, et al. (1995) "The relationship between ligand-binding thermodynamics and protein-ligand interaction forces measured by atomic force microscopy." Biophysical Journal 69(5): 2125-2130 and Allen, S., X. Y. Chen, et al. (1997). "Detection of antigen-antibody binding events with the atomic force microscope." Biochemistry 36(24): 7457-7463); use of synthetic pores (as described in U.S. Pat. No. 8,810,787 and Tabard-Cossa, V., M. Wiggin, et al. (2009) "Single-Molecule Bonds Characterized by Solid-State Nanopore Force Spectroscopy." ACS Nano 3(10): 3009-3014); and use of biological pores (as described in Dudko, O. K., J. Mathe, et al. (2007) "Extracting kinetics from single-molecule force spectroscopy: Nanopore unzipping of DNA hairpins." Biophysical Journal 92(12): 4188-4195 and Tropini, C. and A. Marziali (2007). "Multi-nanopore force Spectroscopy for DNA analysis." Biophysical Journal 92(5): 1632-1637), each of which (patent and/or research paper) publications are incorporated herein by reference in their entirety for all purposes.

Figure 14:
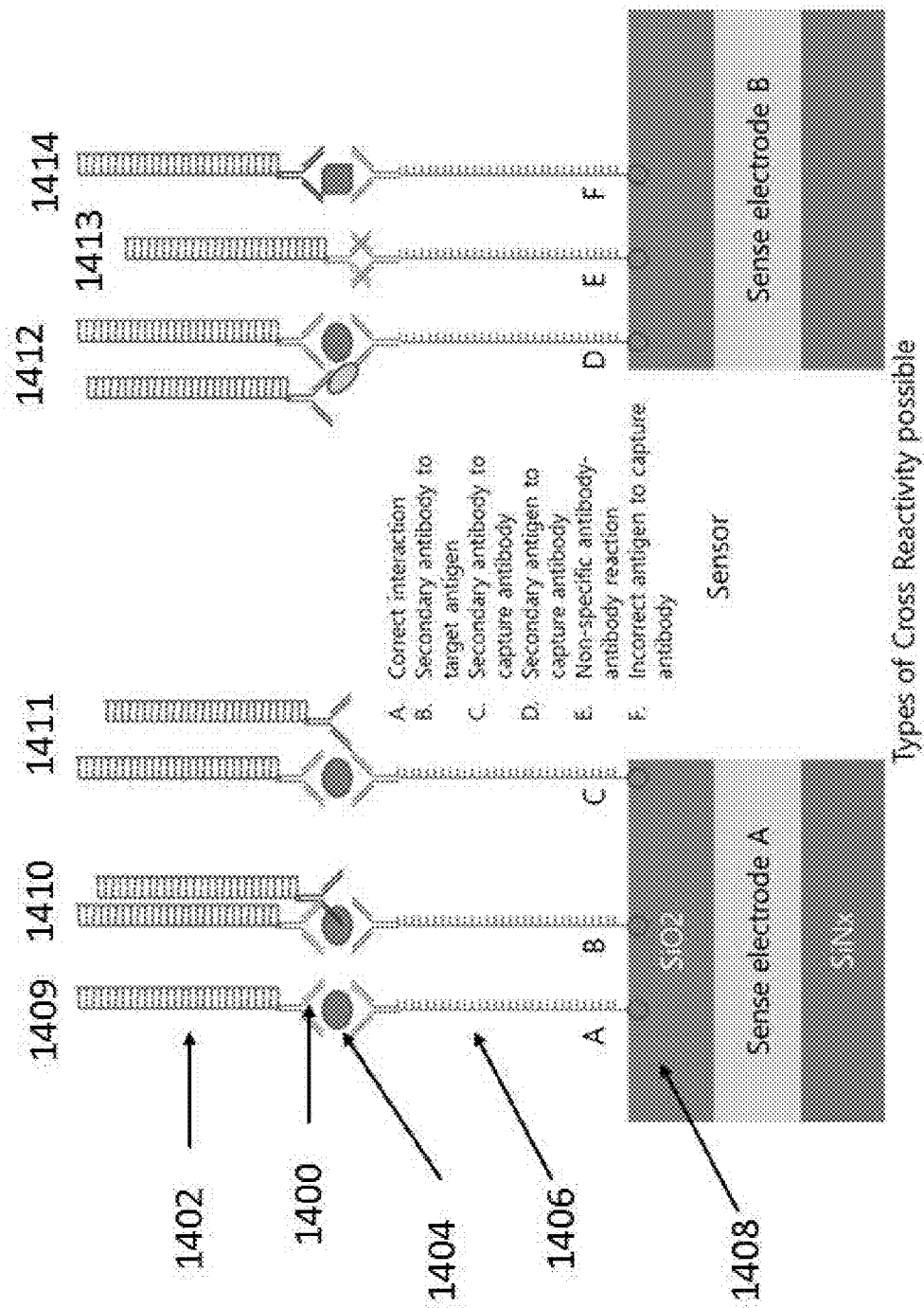
FIG. 14 shows an example of a multiplexed immunoassay where secondary antibodies have an attached nucleic acid to increase and control the amount of charge associated with the analyte.

Various types of cross-reactivity may occur in binding assays, FIG. 14 shows some examples. Given a variety of labels or detection probes, an incorrect label or detection probe can bind to the target in addition to a correct label or detection probe, 1410. An incorrect label or detection probe can bind to the capture probe, 1413. An incorrect label or detection probe can bind to the correct label or detection probe bound to the correct target, 1411. An incorrect label or detection probe-target compound can bind to the correct probe, 1414. An incorrect target can bind to the correct capture probe which has the correct target and correct label or detection probe bound, 1412. An incorrect label or detection probe can be gravitationally or coulombically adsorbed to the detecting surface in absence of any probes. Each of these events can cause an excess of labels or probes to remain on an assay surface resulting in false positives results. Such false positive results can be reduced by the apparatus and methods of the present disclosure, e.g., by applying a force to a surface that is sufficient to remove undesirable labels or probes or targets and/or by having an a priori expectation of the binding force of the capture probe-target-label/detection probe or probe-target complex and correspondingly measuring the force required to break the complex in comparison with the expected binding force.

In an aspect, the present disclosure describes a method for measuring intermolecular interactions, including but not limited to receptor/ligand, protein/protein, nucleic acid/protein and nucleic acid/nucleic acid interactions. A method for measuring intermolecular interactions can involve the simultaneous use of (1) a sensor for detecting the attachment of target molecules in solution to their specific, complementary or near complementary capture molecule bound to a surface (e.g., the hybridization of a nucleic acid in solution to a complementary or near complementary nucleic acid capture probe on the surface) and (2) the use an electric field to apply an electrokinetic force on the bound molecule complex (e.g., a target molecule attached or bound to a capture molecule). When the electrokinetic force exceeds the attachment force of the bound molecule complex, the target molecules can become detached from the capture molecule. This can occur because the attachment force of the capture molecule to the surface can far exceed the attachment force of the target molecule to the capture probe. The electrokinetic force applied by the electric field is such that molecules can be pulled away from the sensor. An electric field may be generated by applying a voltage on two opposing electrodes on the surface of the sensor and device or in solution or a combination. This target molecule may have sufficient charge to create an electrokinetic force that is sufficient to cause the target molecule to become detached from the capture molecule. In some cases, the target molecule can be modified with additional charge to create a greater electrokinetic force on the target molecule. As an example, target nucleic acid molecules can be modified during polymerase chain reaction (PCR) using primers comprising a polyanionic polymer. In the case of immunoassays, a secondary antibody or detection antibody can be labeled with nucleic acid or a polyanionic polymer to enable the application of an electrokinetic force on the antibody in the case that the target molecule has insufficient charge.

The present disclosure also provides several apparatuses capable of employing this method, including an all-electronic platform. In an aspect, the present disclosure provides an apparatus for detecting a charged analyte. The apparatus can comprise a fluidic chamber adapted to contain an electrolyte. The apparatus can further include two or more electrodes, such as a first electrode and a second electrode, capable of providing an electric field within the electrolyte and a surface located between the first electrode and the second electrode and in contact with the fluidic chamber. The surface can include an electrically conducting layer and an electrically insulating layer. There can be a field confining feature located in proximity to the surface. The field confining feature can concentrate the electric field to a strength of at least about $10^3$ volts per meter (V/m), at least about $10^4$ V/m, at least about $10^5$ V/m, at least about $10^6$ V/m, at least about $10^7$ V/m, at least about $10^8$ V/m, at least about $10^9$ V/m or greater in proximity to the field confining feature.

In another aspect, the present disclosure provides a method for detecting binding of a charged analyte. The method can include providing a device having two or more electrodes, such as a pair of electrodes, and a surface between the pair of electrodes. The surface can have a capture probe tethered to a surface at a sensing location. The method can further include contacting the surface with a mixture of charged analytes, where the mixture comprises a target charged analyte and a non-target charged analyte. The charged analytes can form non-covalent bonds with the capture probe. In some cases, the charged analyte binds the capture probe directly. In some cases, the charged analyte binds the capture probe indirectly, e.g., via a molecular linker such as, but not limited to, a chemical compound (e.g., polyethylene glycol), a protein (e.g., one of a protein-protein binding pair, e.g., biotin-avidin, or protein-binding partner pair), a nucleic acid (e.g., a nucleic acid that is hybridizable to a capture probe comprising a nucleic acid or a nucleic acid of a nucleic acid-binding partner pair), or any combination of these. The method can further comprise applying a first voltage across the pair of electrodes, which first voltage results in a first electric field that exerts a first applied force of at least 1 piconewton (pN) on the charged analytes that are bound to the capture probe, thereby breaking non-covalent bonds between the capture probe and the non-target charged analyte. The method can then include detecting the presence of the target charged analyte at the sensing location. In some cases, the first electric field has a strength of at least about $10^3$ volts per meter (V/m), at least about $10^4$ V/m, at least about $10^5$ V/m, at least about $10^6$ V/m, at least about $10^7$ V/m, at least about $10^8$ V/m, at least about $10^9$ V/m or greater in proximity to the sensing location.

In some cases, the method can further comprise applying a second voltage across the pair of electrodes, which second voltage results in a second electric field that exerts a second applied force of greater than 1 pN on the charged analytes that are bound to the capture probe, thereby breaking non-covalent bonds between the capture probe and the target charged analyte. The method can include detecting the absence of the target charged analyte at the sensing location.

Turning now to the figures, FIG. 1A shows an example of a cross-sectional profile view of an apparatus of the present disclosure. The apparatus can include a fluidic chamber adapted to contain an electrolyte 101. A first electrode 102 can be located in the electrolyte and form a circuit with a second electrode 103, across which electrodes a voltage can be applied by a voltage source 104. In this case, the second electrode forms one of the walls of the fluidic chamber. In some cases (e.g., see FIG. 1C), the fluidic chamber is bisected by a membrane and the first and second electrodes are on opposing sides of the membrane. A surface is laid in proximity to or upon the second electrode in this embodiment. The surface can include an electrically insulating layer 105 and an electrically conducting layer 106. In some cases, the electrically conducting layer is exposed to the electrolyte 101. The surface can have field confinement features 107 in proximity to the surface (e.g., within or upon the surface). The field confinement features can increase the magnitude of an applied electric field in proximity to the field confinement features.

The apparatus can use an electric field to draw an anchored capture probe and its attached target into a pore to detect the total charge using an auxiliary sensor. The difference in charge between the capture molecules in their non-hybridized (e.g., not bound to target) and hybridized states (e.g., bound to target) can be used to determine the presence of bound molecules. This architecture can be well suited for probing the binding energy of a molecule pair. While measuring the presence of the molecule pair under the influence of an electric field, the electric field can be gradually increased until the electrokinetic force exceeds the binding energy of the molecule pair. Once the target molecule detaches, a change in charge in the sensing area can be detected and that change can be used to determine the binding voltage of the pair.

Figure 1B:
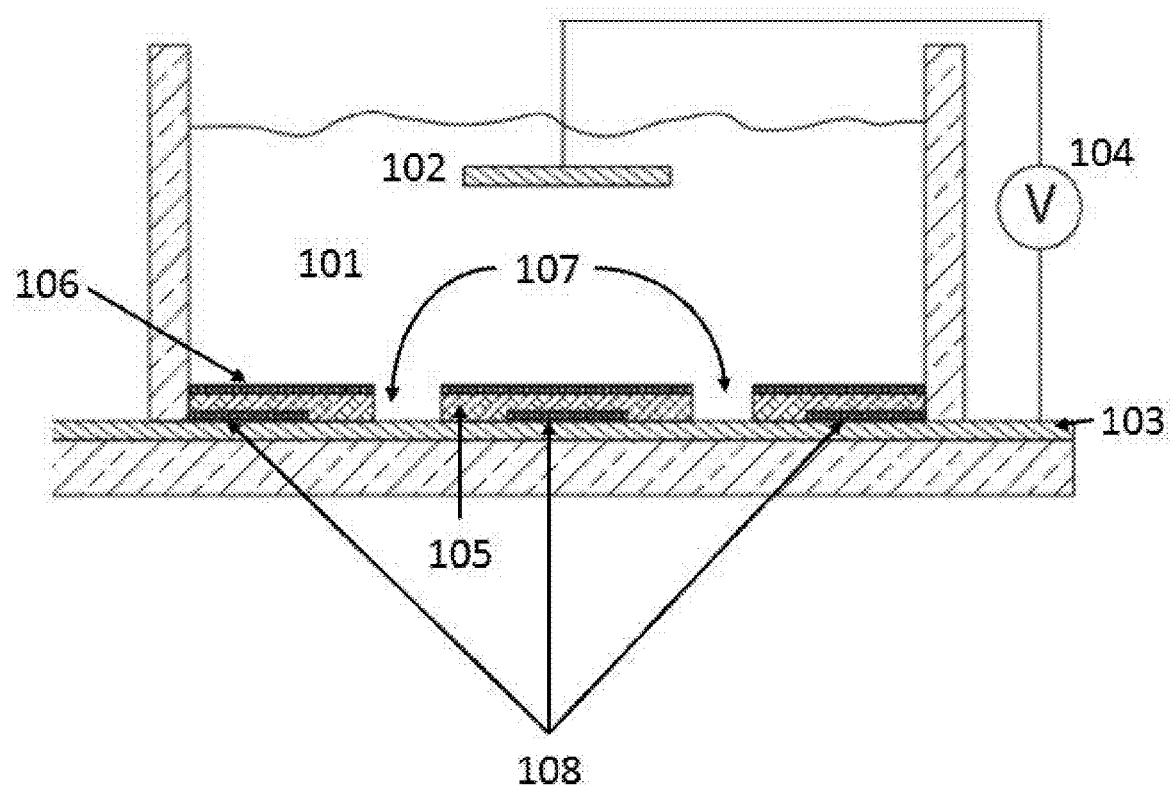
FIG. 1B shows an example of a cross-sectional profile view of an apparatus of the present disclosure having a conducting film.

In some cases, the apparatus includes a bias stabilization layer. With reference to FIG. 1B, the bias stabilization layer 108 can be made from any electrically conductive material, such as a metal (e.g., silver, copper, gold, and platinum). In cases where the bottom electrode 103 has a low conductivity (e.g., such as indium tin oxide (ITO), used for example in cases where the electrode is transparent to facilitate optical detection), the amount of current drawn by the electric field can cause a significant drop in voltage in the bottom electrode itself. This voltage drop can accentuate any differences in the electric field generated at each sensing location, which can be undesirable for maintaining a relatively constant applied force at each sensing location. The voltage drop and variation between sensing locations can be remedied, at least in part, by including the bias stabilization layer 108 in the apparatus. In some cases, the bias stabilization layer is optically opaque and does not occlude the sensing locations. The bias stabilization layer can extend out to the voltage source 104 (not shown). In some cases, the ratio of the applied voltages of the sensing location having the lowest applied voltage compared to the sensing location having the highest applied voltage is less than about 50%, less than about 40%, less than about 30%, less than about 20%, less than about 10%, less than about 5%, less than about 3%, or less than about 1%.

Figure 1C:
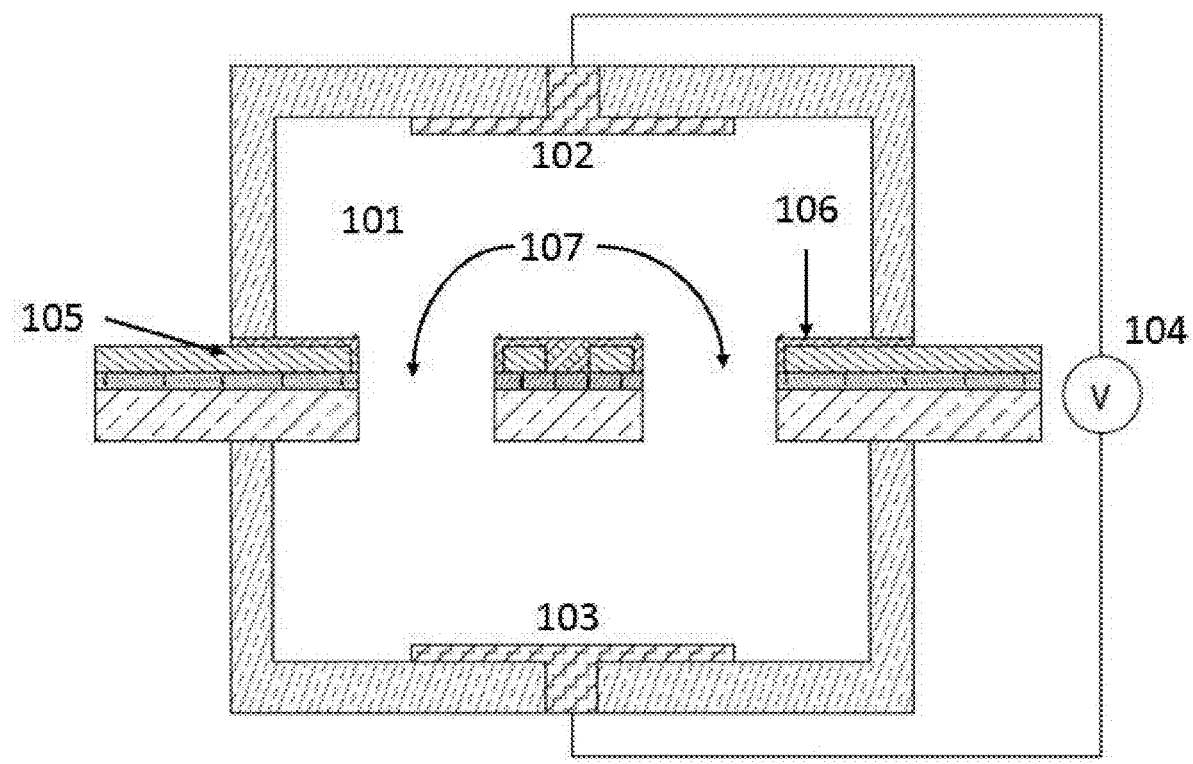
FIG. 1C shows an example of a cross-sectional profile view of an apparatus of the present disclosure having a pore.

FIG. 1C shows an example of a cross-sectional profile view of an apparatus of the present disclosure where the sensor surface bisects the fluidic chamber. The fluidic chamber of FIG. 1A, FIG. 1B and FIG. 1C can be a microfluidic chamber (e.g., having a smallest dimension of less than about 1 millimeter). As with FIG. 1A, the apparatus can include an electrolyte 101, a first electrode 102, a second electrode 103, a voltage source 104, an electrically insulating layer 105, an electrically conducting layer 106 and a field confinement feature 107.

Various factors may affect the degree of confinement of a confinement feature (e.g., orifice). The design of the confinement features, such as aspect ratio and density of features, may affect the degree of confinement. Higher aspect ratios may help to reduce the effects of a fringing field. For dense packing of the confining features, the overlap in fringing field can reduce the effect of field confinement. In some cases, the overlapping of fringing field between features can be reduced by providing a region for the fields to terminate before overlapping, such as a conducting surface near the confinement feature. Such a surface can effectively pin the potential near the orifice to allow for further enhancement of the electric field and thus the generated electrokinetic force. An in silico study of the effect of such a field terminating location along with an investigation into the effects of feature aspect ratio is shown herein. The presence of a conductive surface layer may both enhance single feature's ability to confine the electric field and be very effective against countering the reduction from integration of confinement features into an array.

Figure 2A:
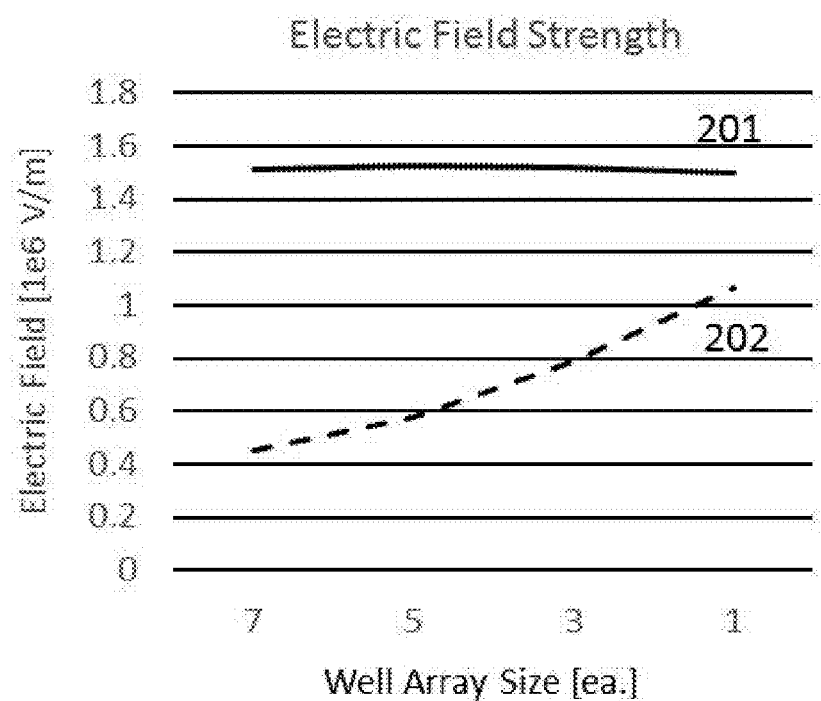
FIG. 2A shows an example of the effect of sensor array size on electric field strength.

As described herein, the size, shape, arrangement and number of field confinement features can have an effect on the magnitude of the electric field created in proximity to the field confinement features and the amount of force that can be applied to the charged analyte. FIG. 2A shows an example of the effect of sensor array size on electric field strength. As seen here, the electrically conductive layer (also referred to as the potential pinning or field terminating layer/plane) may help to create a stronger electric field, particularly as the number of sensing locations (e.g., wells) increases. The electric field in this case may be relatively constant at about $1.5 \times 10^6$ V/m when an electrically conducting layer is used 201, while the electric field in the absence of the conducting layer 202 may be both lower in magnitude and decreases as the well array size increases. The horizontal axis is number of sensing locations on a side of a square array (e.g., a single location, a 3×3 array, a 5×5 array and a 7×7 array). The electric fields depicted in FIG. 2A, FIG. 2B, FIG. 3 and FIG. 4 are achieved with confinement features having a diameter of 1 m and spaced 4 m apart.

Figure 2B:
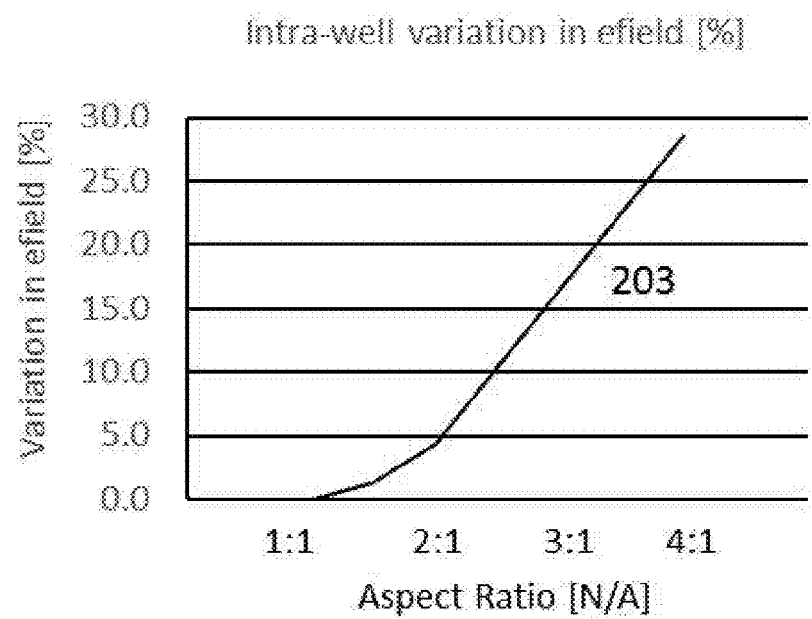
FIG. 2B shows an example of the effect of aspect ratio on the inter-sensor variation in electric field strength.

FIG. 2B shows an example of the effect of aspect ratio on the inter-sensor variation in electric field strength. The system architecture is an array of wells as shown in FIG. 1A, where the aspect ratio is defined as the width of the well (e.g., along the surface) divided by the depth of the well (e.g., into the surface). As shown, the electric field strength variation (as measured in %) 203 increases with increasing aspect ratio. The electric fields at the bottoms of the microwells are compared to determine the variation. In this example, the variation in electric field approaches 0.0% (e.g., all sensing locations have the same field) at an aspect ratio of 1:1. In some embodiments, the aspect ratio is less than about 5:1, less than about 4:1, less than about 3:1, less than about 2:1, less than about 1:1, or less than about 1:2.

Figure 3:
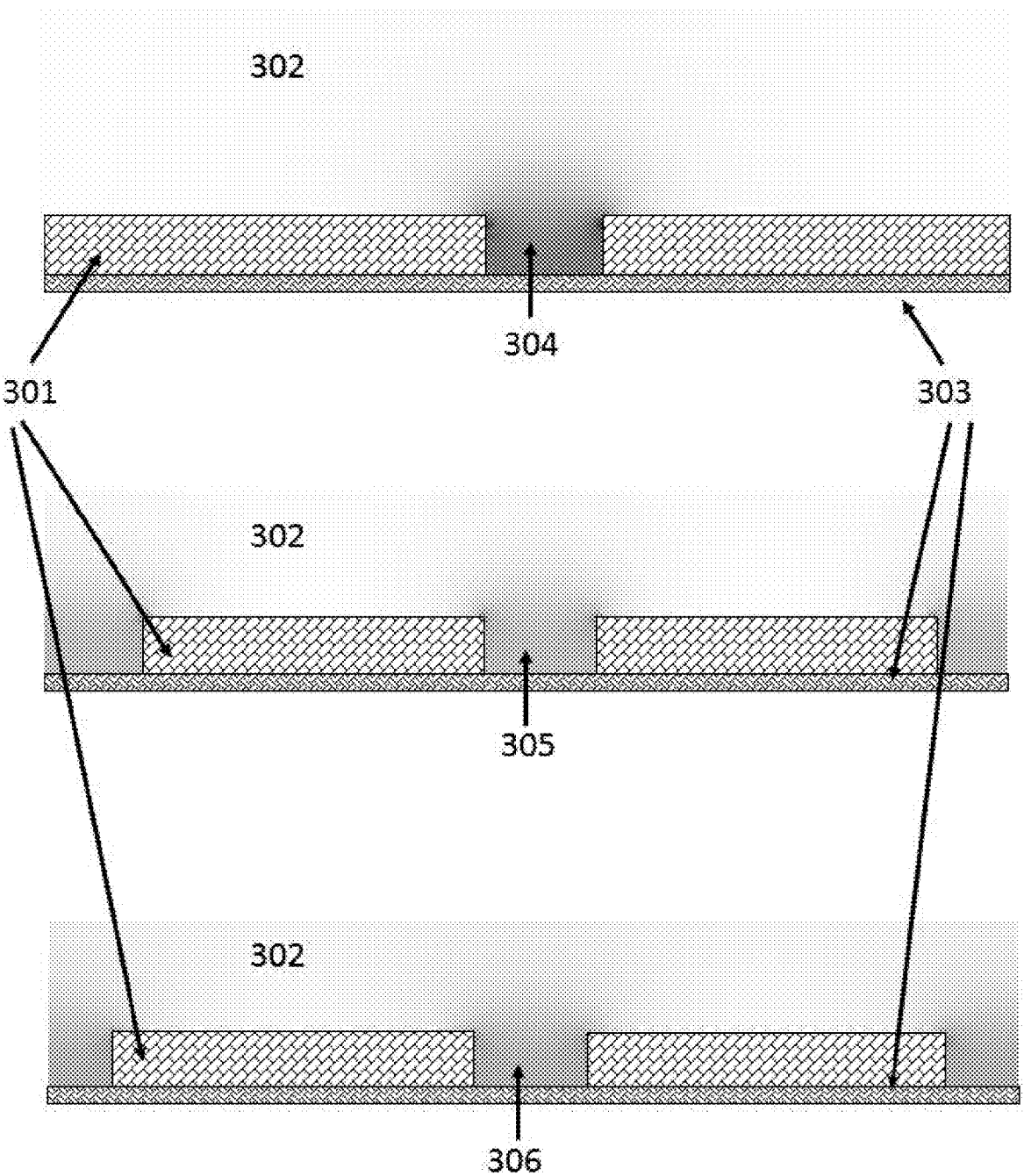
FIG. 3 shows an example of the electric field produced without an electrically conducting layer.
Figure 4:
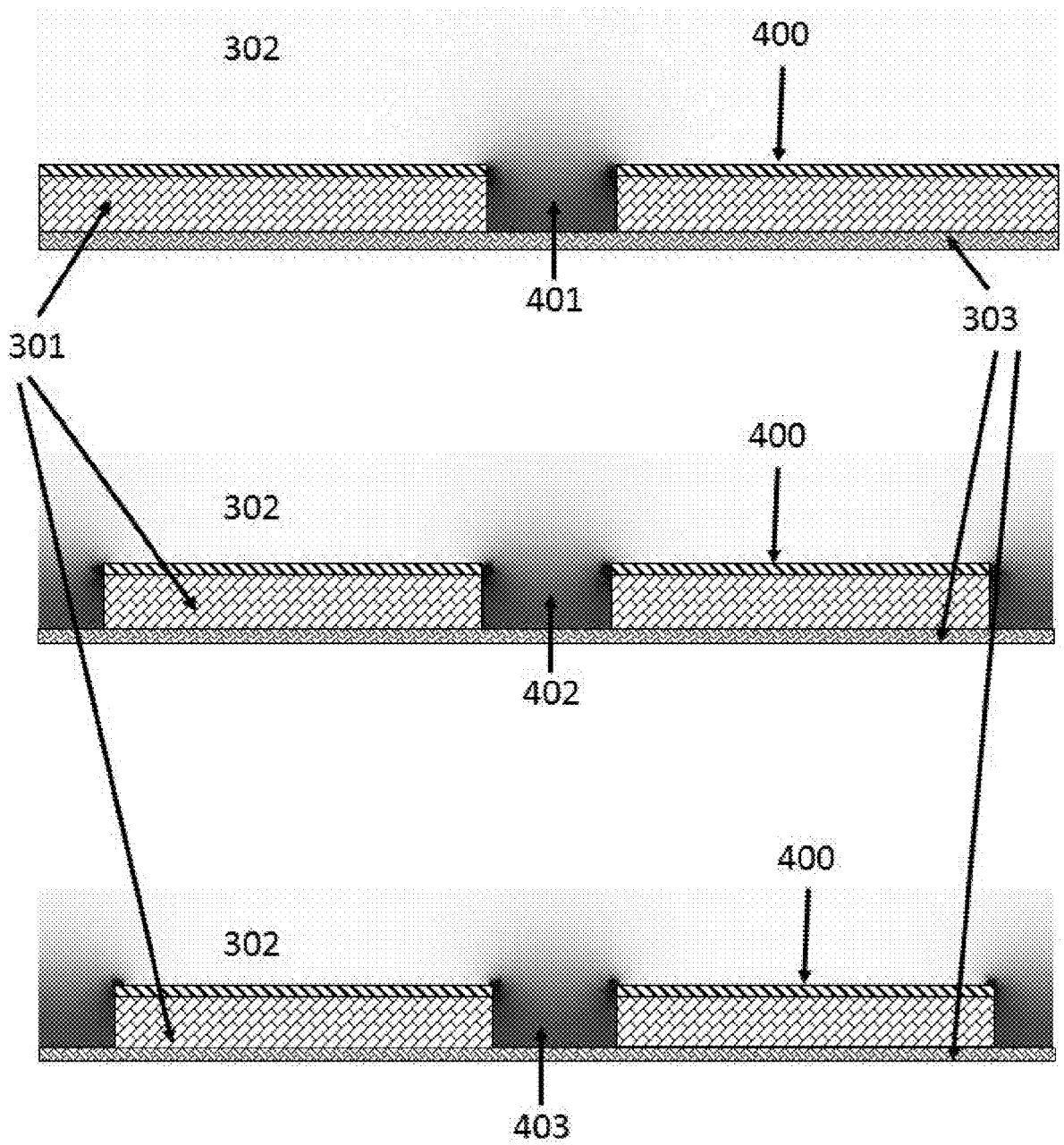
FIG. 4 shows an example of the electric field produced with an electrically conducting layer (e.g., field terminating plane)

The effect of the field terminating layer is shown graphically in FIG. 3 and FIG. 4. Referring to FIG. 3, the system includes an insulating layer 301, an electrolyte 302, and a first electrode 303. A voltage can be applied between the first electrode and second electrode (not shown) to create an electric field that is concentrated in the field confinement features (wells in this case). FIG. 3 shows a series of three profile views of sensor arrays. The magnitude of the electric field decreases as the number of wells increases from a single well 304, to a 3×3 array of 9 wells 305, to a 7×7 array of 49 wells 306.

FIG. 4 shows a system similar to FIG. 3 including an insulating layer 301, an electrolyte 302, and a first electrode 303. The system also includes an electrically conducting layer 400 disposed upon the insulating layer. In comparison to FIG. 3 without the electrically conducting layer, the magnitude of the electric field is both stronger and does not diminish with increasing array size. The magnitude of the electric field is shown with shading (darker being stronger) for a single sensor 401, a 3×3 array 402 and a 7×7 array 403.

In some embodiments, the applied electrokinetic force on the charged analyte ranges from 0 pN to 5000 pN. In some instances, the electric field confining feature (e.g., an orifice) and/or conducting potential pinning plane can be used to enhance the electrokinetic force. In some cases, the applied force is sufficient to dissociate the analytes from the capture probes (e.g., receptor/ligand, protein/protein, nucleic acid/protein or nucleic acid/nucleic acid interactions) sequentially (e.g., in the order of their binding strengths). The method can be able to judge whether molecules are correctly (specifically) or incorrectly (non-specifically) bound to their intended targets.

In some embodiments, the apparatus and methods of the present disclosure are used to detect and probe the binding force of a single nucleotide polymorphism (SNP) or to analyze immunoassays (e.g., sandwich immunoassays). In some cases, more than one sensor can be integrated in a single chip to allow for parallel analysis of SNPs, immunoassay and sandwich immunoassays by themselves or simultaneously.

The methods of the present disclosure can involve detecting charged analytes by any suitable approach, such as, for example, optical detection, electrical or electrostatic detection, or plasmonics detection.

Figure 5:
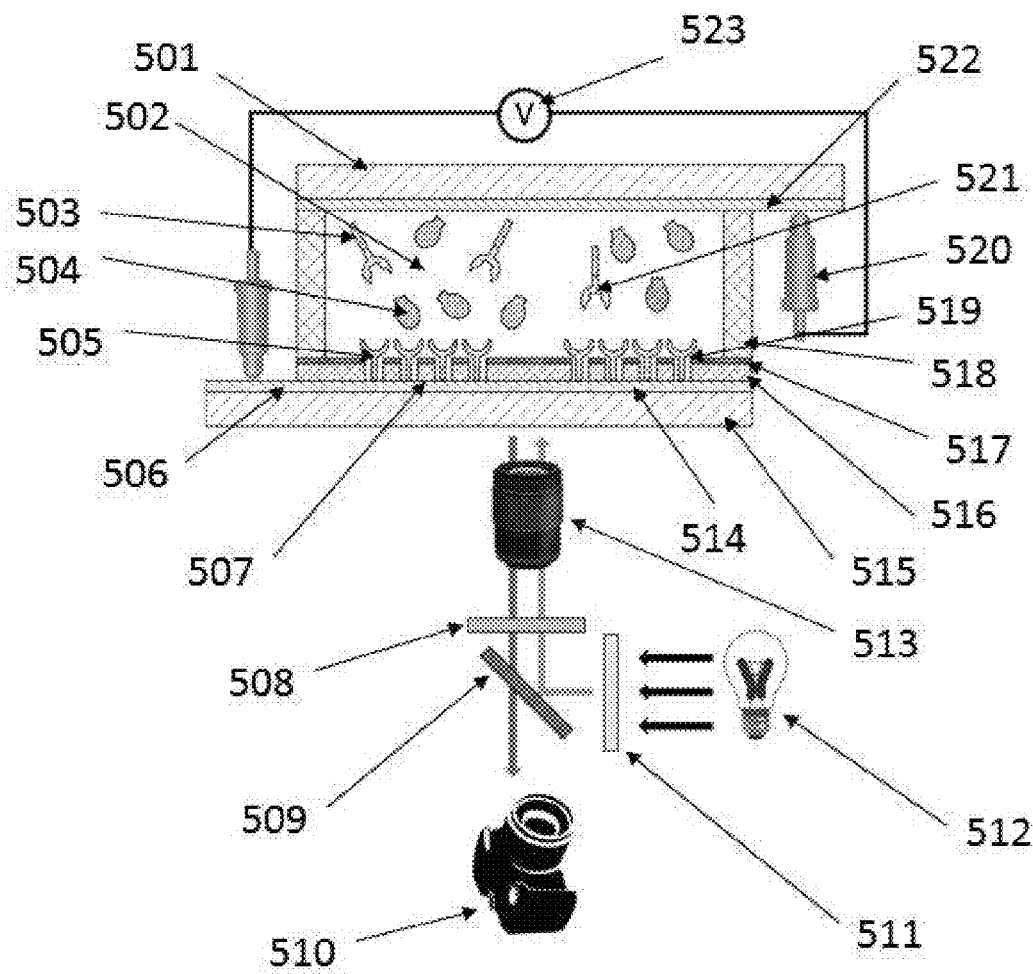
FIG. 5 shows an example of an apparatus of the present disclosure adapted for optical detection of charged analytes.

FIG. 5 shows an example of an apparatus of the present disclosure adapted for optical detection of charged analytes (e.g., using a modified fluorescence based DNA microarray). The apparatus can include a top substrate 501 and a bottom substrate 515 (e.g., which can be an optically transparent material), as well as fluidic walls 518 that define a fluidic chamber. In some cases, the chamber is microfluidic (e.g., having micrometer dimensions) and contains an electrolyte 502. A voltage source 523 can be connected by electrical connectors 520 to a first electrode 522 and a second electrode 506. The electrode can be overlaid by a surface having an insulating layer 516 and a conducting layer 517. The surface can be interrupted by a plurality of field confinement features, which in this embodiment are clustered into a first sensing location 507 and a second sensing location 514, which sensing locations are pixels in the optical detection system shown here. The optical detection system can include a light source 512, an excitation filter 511, a dichroic mirror 509 and an emission filter 508. The light can pass through these components as well as an optics module 513 (e.g., containing lenses) that directs light to the sensing locations at an excitation wavelength and receives light from the fluorescent label 503 at an emission wavelength. The emission radiation can be imaged using an imaging system 510 (e.g., containing a camera). Capture probes (e.g., antibodies) can be tethered in proximity to the sensing locations. In this case, a first antibody 505 is tethered to the surface (e.g., to the electrode) at the first sensing location 507 and a second antibody 519 is tethered at the second sensing location 514. A first target antigen 504 binds to the first antibody 505 (e.g., capture probe) and a secondary antibody 521 having a fluorescent probe 503 can bind to the target antigen in order to concentrate a fluorescent signal at the sensing locations.

The bottom surface can act like the surface of a traditional nucleic acid microarray and is packaged with a fluidic channel on top. Both the top surface of the microarray and the bottom surface of the fluidic channel can be modified to have an electrode. Either one or both electrode surfaces can be a transparent conducting material, for example indium tin oxide (ITO) to allow for simultaneous imaging of the surface and the application of an electric field. The process of detection is shown in FIG. 6A to FIG. 6E. For clarity, it may be assumed that only events on the surface lead to a fluorescent signal and there is very little background. In practice, this can be accomplished by first hybridizing the target nucleic acid on the microarray slide and washing prior to testing. As the voltage is increased, the electrokinetic force on the hybridized nucleic acid may increase until nucleic acid is pulled off. This pull-off voltage can be related to the binding energy of the target analyte to the capture probe, which is identified as the binding energy voltage ($V_{BE}$). This can be used to discriminate between a target that may be a correct complementary match and a target that has a single or plurality of mutations and is not completely complementary to the capture probe. A target that is not completely complimentary to the capture probe may still hybridize to the probe. The methods of the present disclosure can be used to identify this hybridization between a target that is not completely complementary to the capture probe (e.g., due to the target detaching at a lower voltage). This method can be employed to identify mixed mutation samples on a single capture site.

Figure 6A:
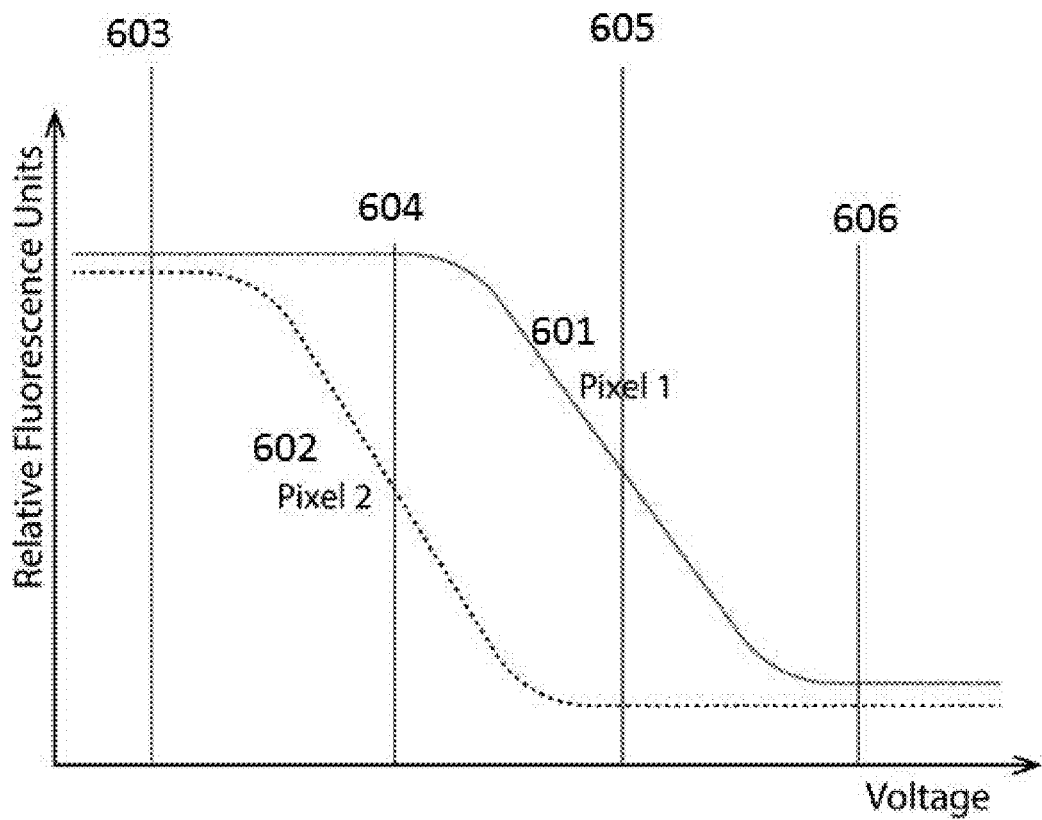
FIG. 6A shows an example of the magnitude of the fluorescent signal as a function of applied voltage for operation of the apparatus of FIG. 5.

FIG. 6A shows an example of the magnitude of the fluorescent signal as a function of applied voltage for operation of the apparatus of FIG. 5. The applied voltage can be increased over time and the fluorescence output at the first pixel 601 and the second pixel 602 can be monitored. The signal begins relatively higher at lower applied voltages as analyte is bound both specifically and non-specifically and decreases according to the curves shown in FIG. 6A as the voltage is increased, providing a force that pulls the charged analytes from the capture probes. A series of drawings are provided which clarify the binding of the analytes at various applied voltages; with the lowest voltage at position 603 corresponding to FIG. 6B, the third highest voltage at position 604 corresponding to FIG. 6C, the second highest voltage at position 605 corresponding to FIG. 6D, and the highest voltage at position 606 corresponding to FIG. 6E.

Figure 6B:
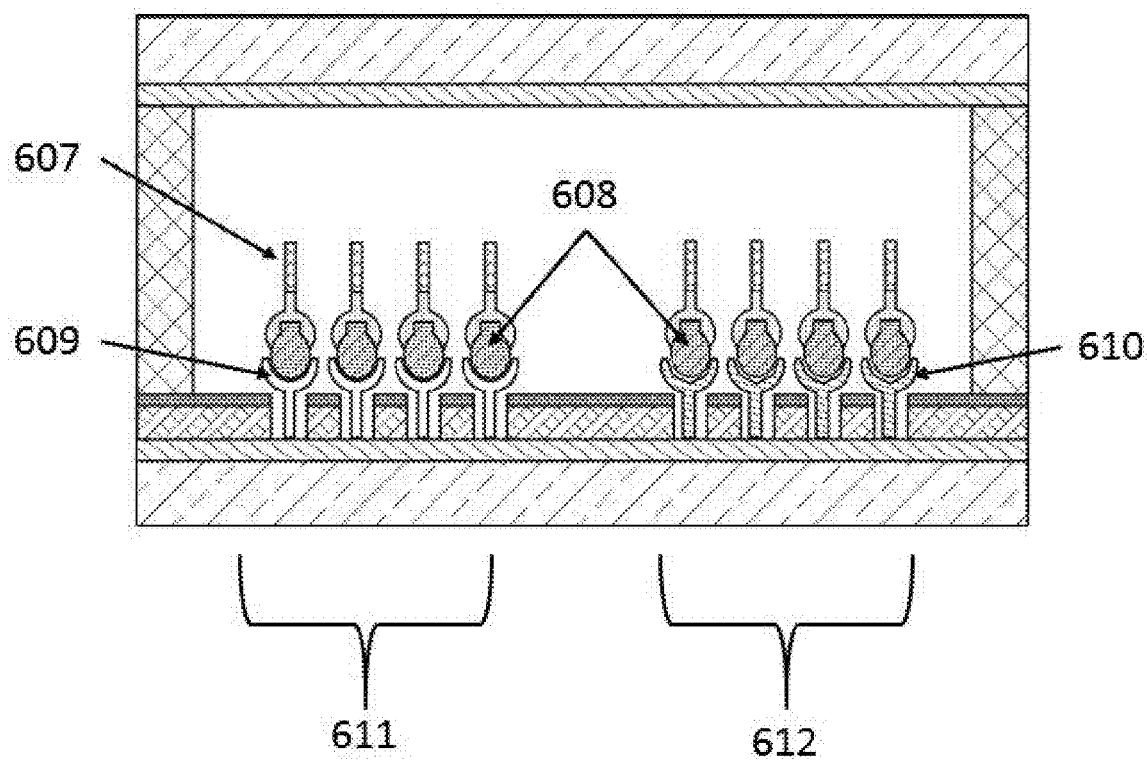
FIG. 6B shows an example of the operation of the apparatus of FIG. 5 at a first voltage.

FIG. 6B shows an example of the operation of the apparatus of FIG. 5 at a first voltage where initial binding occurs. The first pixel 611 has a plurality of the first capture antibodies 609 tethered to it and the second pixel 612 has a plurality of the second capture antibodies 610 tethered to it. The charged analyte 608 can bind specifically (e.g., at high strength) to the first capture antibody and can bind non-specifically (e.g., at low strength) to the second capture antibody. The charged analytes can be bound by a fluorescent label 607. As shown in FIG. 6A, a fluorescent signal can be detected at both the first and second pixel, however, since the magnitudes of the signals are similar at the first voltage, specific versus non-specific binding cannot be easily differentiated at the first applied voltage. Therefore, the applied voltage can be increased to a second voltage.

Figure 6C:
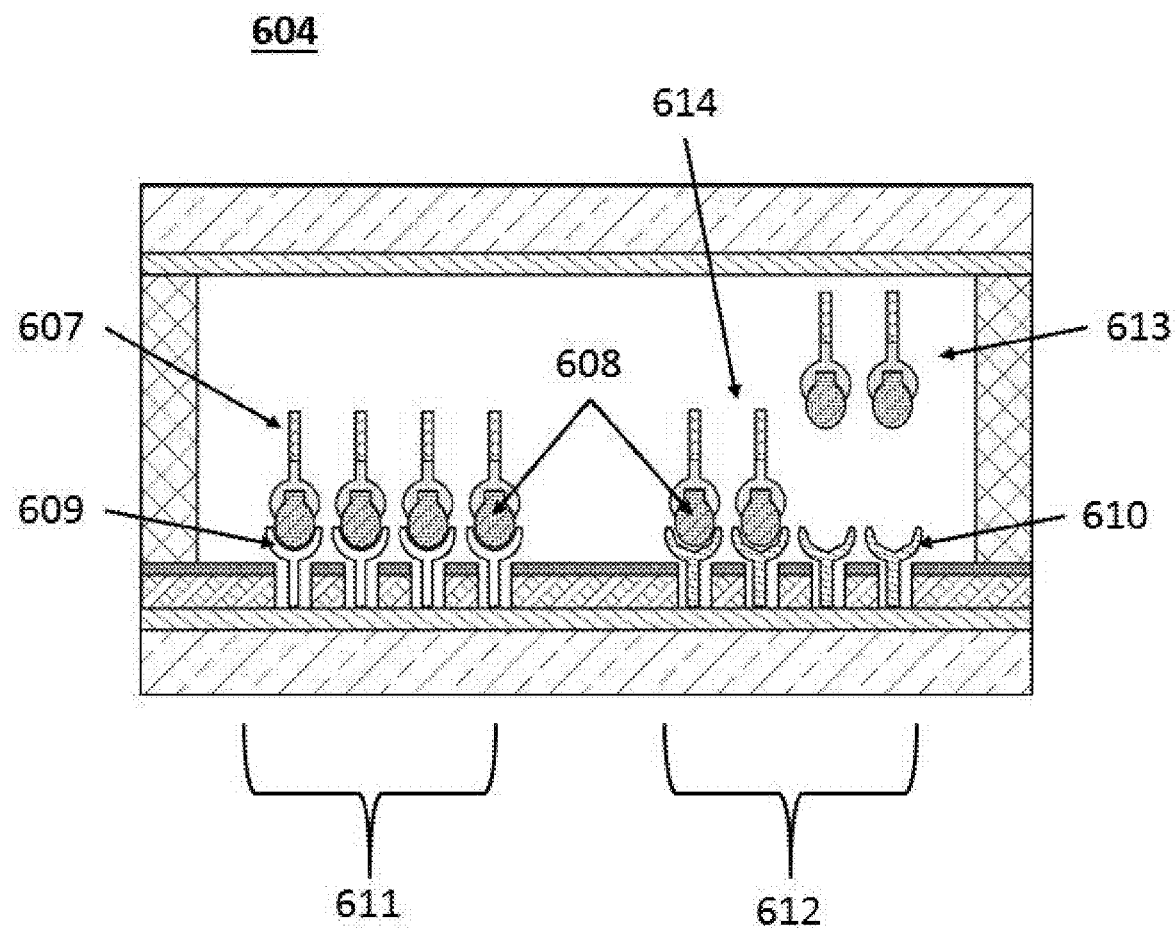
FIG. 6C shows an example of the operation of the apparatus of FIG. 5 at a second voltage.

FIG. 6C shows an example of the operation of the apparatus of FIG. 5 at a second voltage where non-specific components detach 613. The detachment from the second capture antibody can be due to the applied force exerted on the charged analyte by the electric field in proximity to the confinement features. In this case, some non-specifically bound analytes 614 remain bound at the second voltage, which can be detached by increasing the applied voltage further.

Figure 6D:
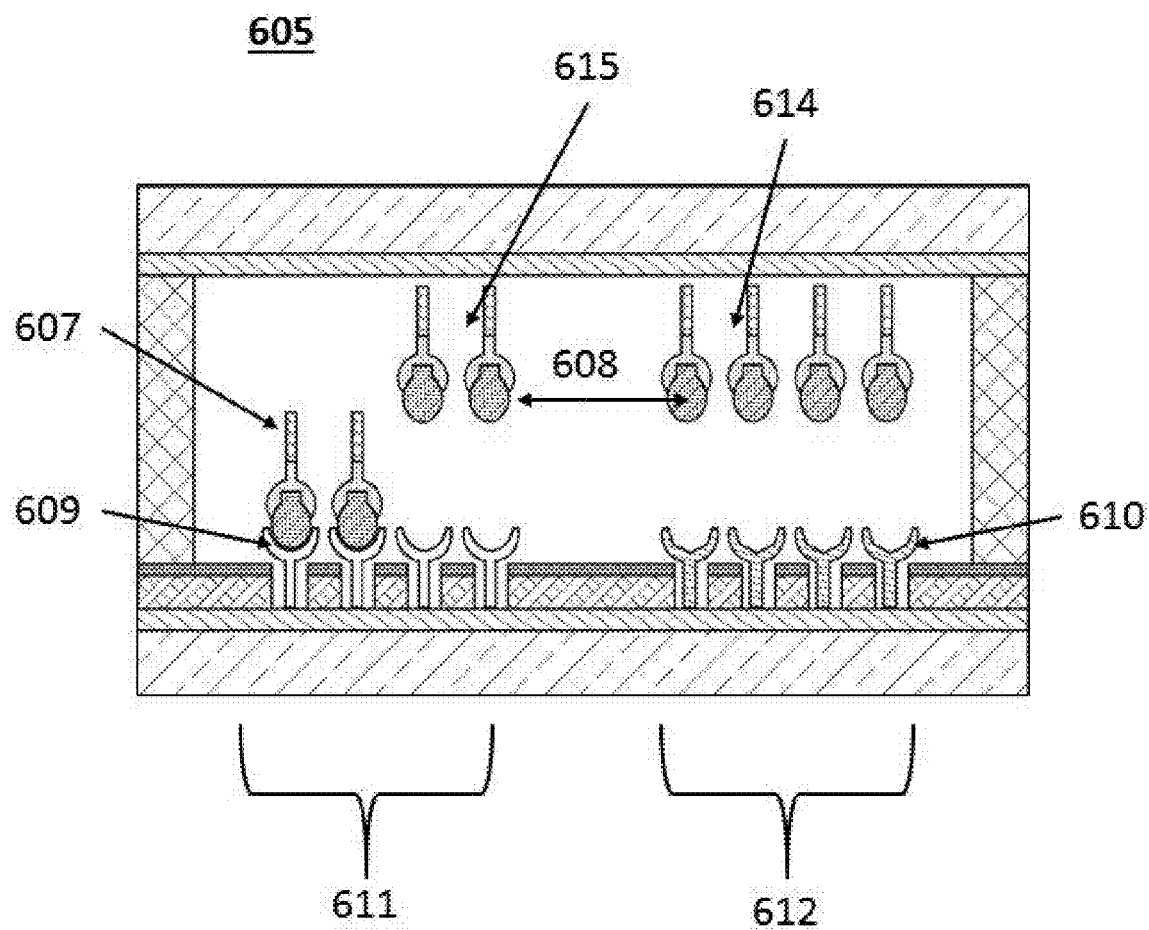
FIG. 6D shows an example of the operation of the apparatus of FIG. 5 at a third voltage.
Figure 6E:
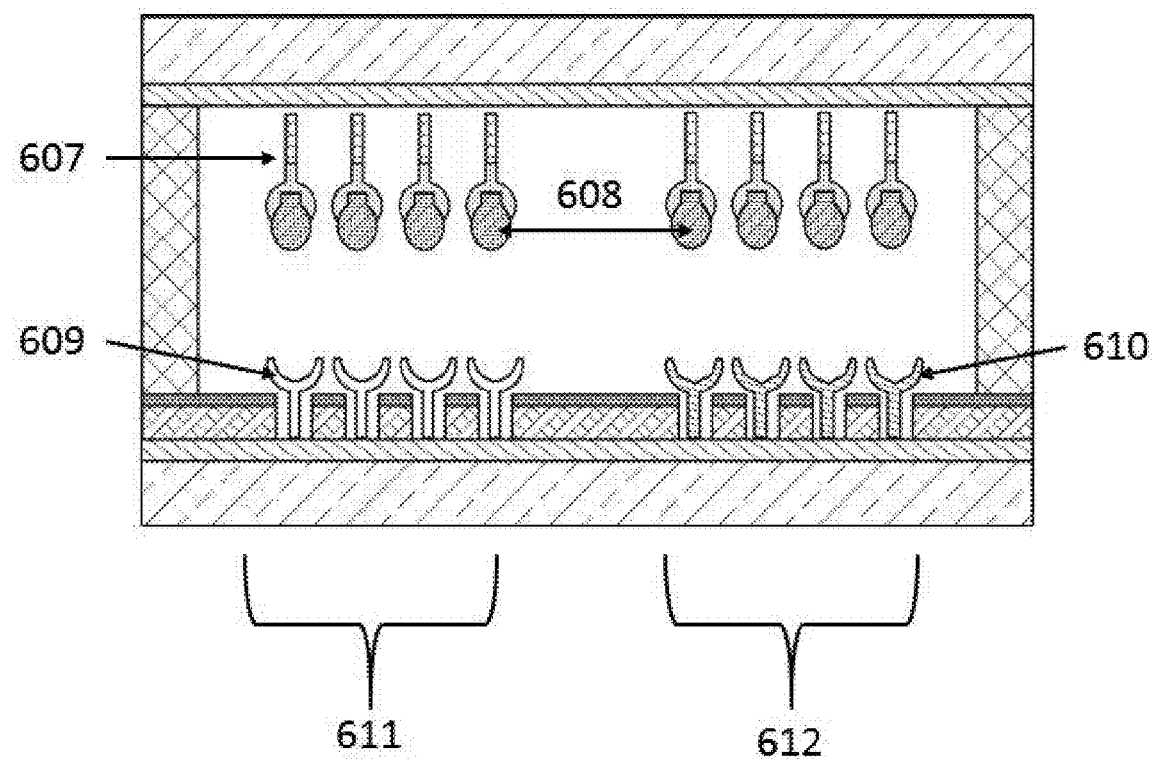
FIG. 6E shows an example of the operation of the apparatus of FIG. 5 at a fourth voltage.

FIG. 6D shows an example of the operation of the apparatus of FIG. 5 at a third voltage. The remaining non-specific binders detach 614. In some cases, some true positives 615 (e.g., specifically bound analytes) detach as well. As shown in FIG. 6E, the applied voltage can be increased yet further to a fourth voltage where all components detach. The third and/or fourth voltages can be used to determine the binding force between the target antigen and the capture probe.

Figure 7:
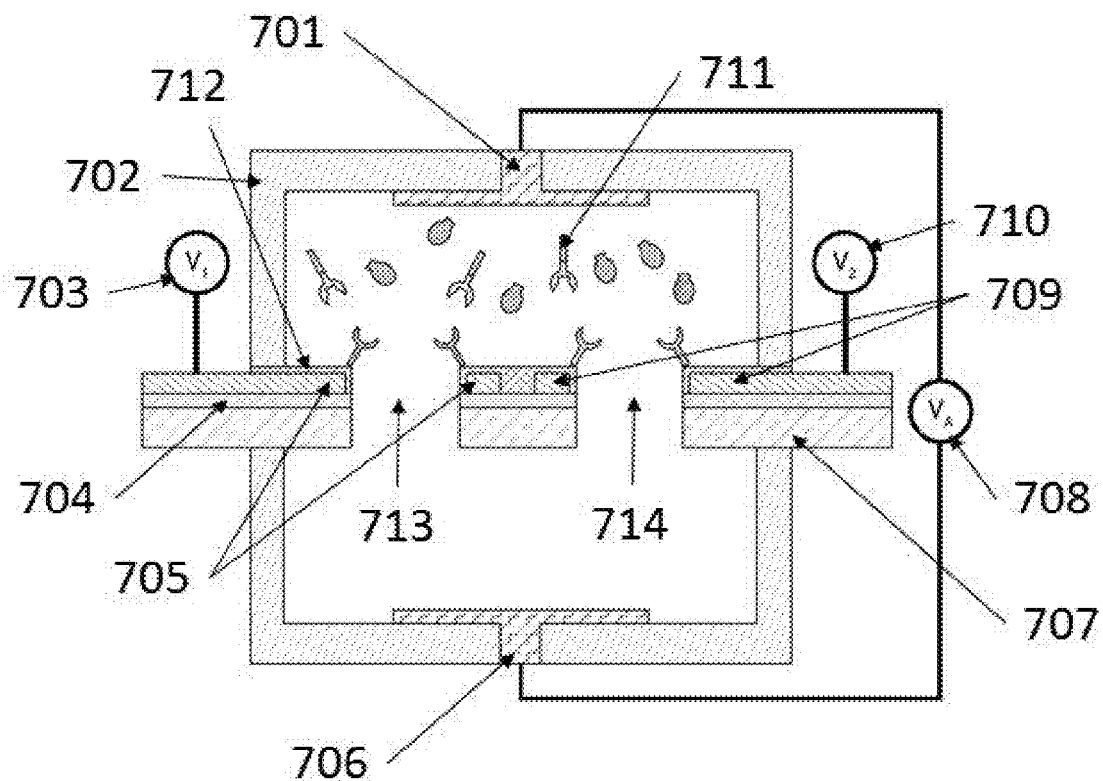
FIG. 7 shows an example of an apparatus of the present disclosure adapted for electrical detection of charged analytes.

In some cases, the charged analytes can be electronically detected. FIG. 7 shows an example of an apparatus of the present disclosure adapted for electrical detection of charged analytes. The apparatus can include a fluidic chamber 702 (e.g., microfluidic) that is bisected by a surface and contains a fluorescent label 711. The surface can include several layers including a substrate 707, an insulating layer 704 (e.g., a dielectric membrane) and a field terminating layer 712 (e.g., a conducting metal such as platinum, copper, aluminum or silver). An applied voltage can be applied using a voltage source 708 in electrical communication with a first electrode 701 and a second electrode 706. A sensing electrode can also be located in proximity to the surface. In this case, a first sensing electrode 705 surrounds the first field confinement feature 713 and a second sensing electrode 709 surrounds the second field confinement feature 714. The sensing electrodes can be individually addressable. The binding of charged analytes in proximity to the first field confinement feature can be monitored by a first voltage output 703. The binding of charged analytes in proximity to the second field confinement feature can be monitored by a second voltage output 710.

Figure 8A:
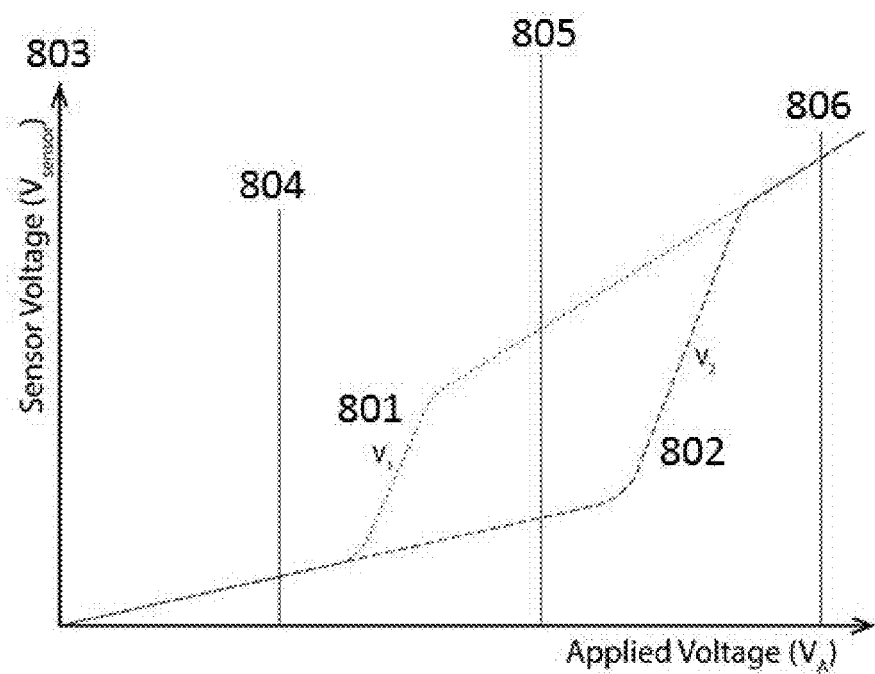
FIG. 8A shows an example of the magnitude of sensor voltage as a function of applied voltage for operation of the apparatus of FIG. 7.

FIG. 8A shows an example of the magnitude of the electrical signal as a function of applied voltage for operation of the apparatus of FIG. 7. The applied voltage can be increased over time and the voltage output near the first confinement feature 801 and near the second confinement feature 802 can be monitored. The signal begins relatively lower at lower applied voltages as analyte is bound both specifically and non-specifically and pulled into the orifice (e.g., field confinement feature) and eventually detach. A series of drawings are provided which clarify the binding of the analytes at various applied voltages; with the lowest voltage at position 803 corresponding to FIG. 8B, the third highest voltage at position 804 corresponding to FIG. 8C, the second highest voltage at position 805 corresponding to FIG. 8D, and the highest voltage at position 806 corresponding to FIG. 8E.

Figure 8B:
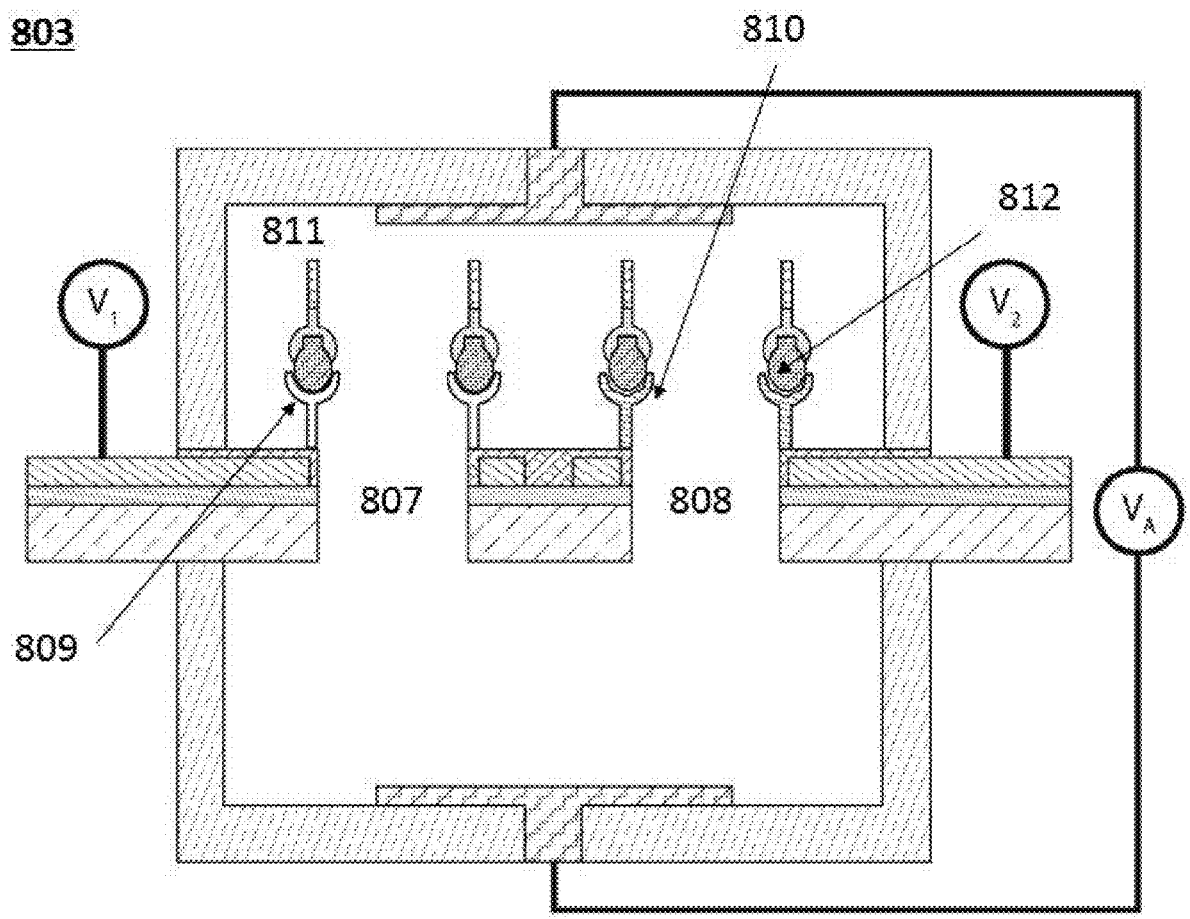
FIG. 8B shows an example of the operation of the apparatus of FIG. 7 at a first voltage.

FIG. 8B shows an example of the operation of the apparatus of FIG. 7. The apparatus has a first orifice 807 and a second orifice 808. A first capture probe 809 is tethered in proximity to the first orifice 807 and a second capture probe 810 is tethered in proximity to the second orifice 808. In this case, the analyte 812 itself is not charged. It can become charged by associating with a charge label 811. The charge label can be covalently or non-covalently attached to the analyte, and the analyte may thereby become a charged analyte. The charge label can be a fixed to a secondary antibody that also binds to the analyte. The analyte can bind to the capture probes and the secondary antibody at a low (or zero) applied voltage 803.

Figure 8C:
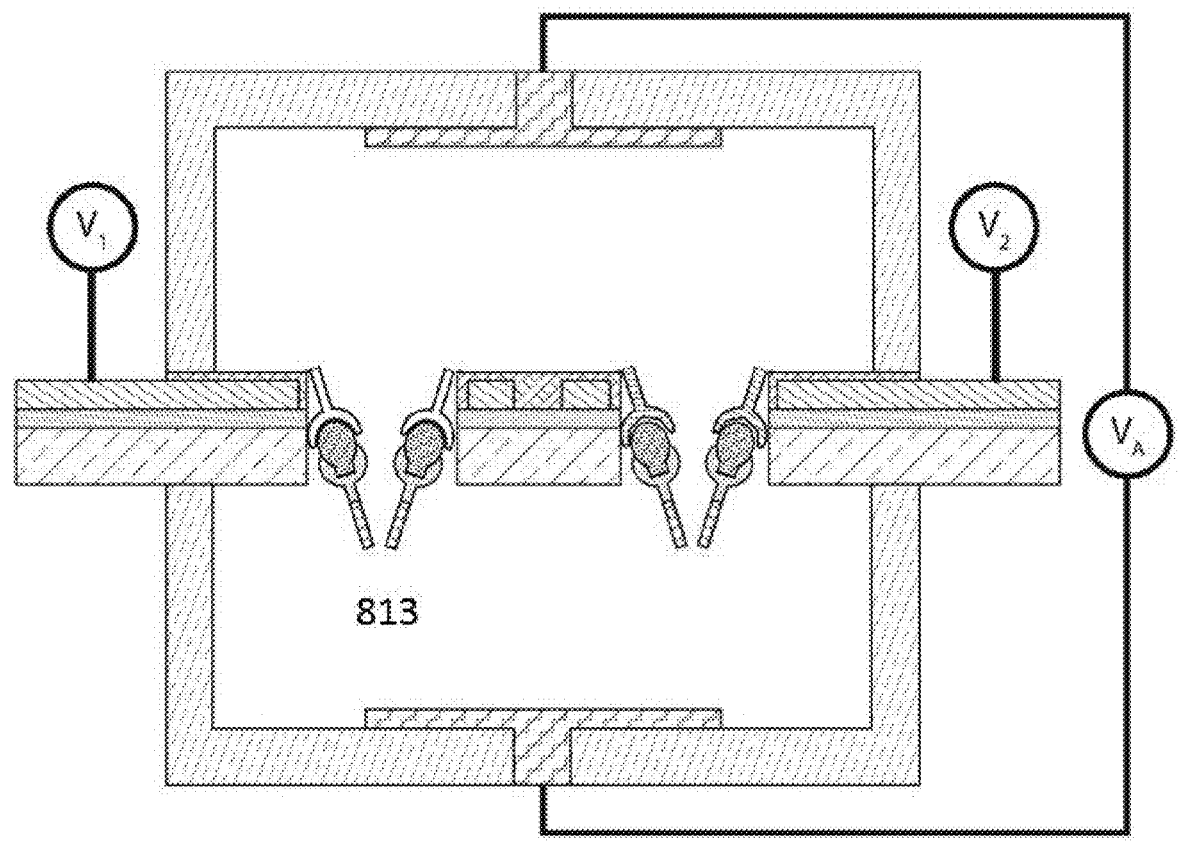
FIG. 8C shows an example of the operation of the apparatus of FIG. 7 at a second voltage.

As shown in FIG. 8C, the applied voltage can be increased to a second voltage sufficient to pull the charged analytes into the orifice 813. An electrical signal can be detected at both the first and second orifice, however, since the magnitudes of the signals are similar at the second voltage, specific versus non-specific binding cannot be easily differentiated at the second applied voltage. Therefore, the applied voltage can be increased to a third voltage.

Figure 8D:
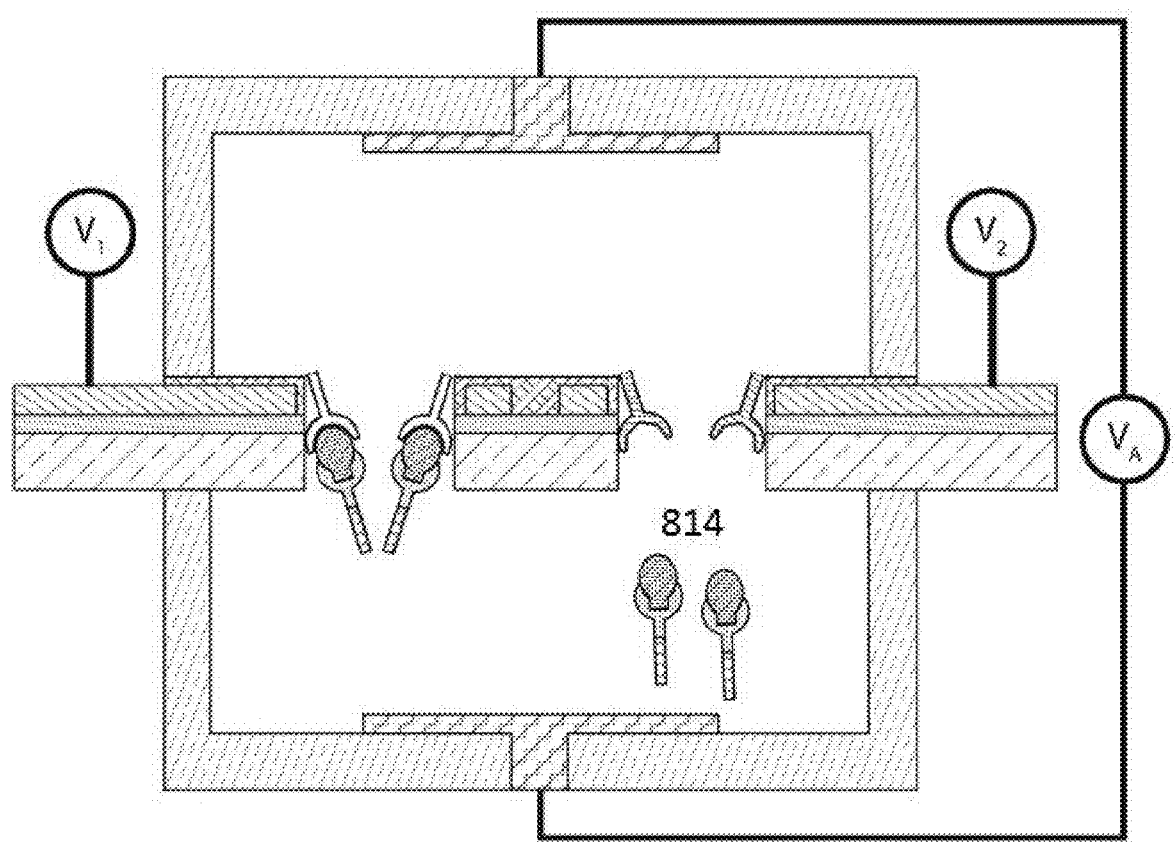
FIG. 8D shows an example of the operation of the apparatus of FIG. 7 at a third voltage.

FIG. 8D shows an example of the operation of the apparatus of FIG. 7 at a third voltage where non-specific components detach 814. The detachment from the second capture antibody can be due to the applied force exerted on the charged analyte by the electric field in proximity to the confinement feature. As shown in FIG. 8A, there is a difference in sensor voltage signal between the first orifice and the second orifice, therefore the third voltage can distinguish between specific and non-specific binding of the analyte in proximity to the field confining feature.

Figure 8E:
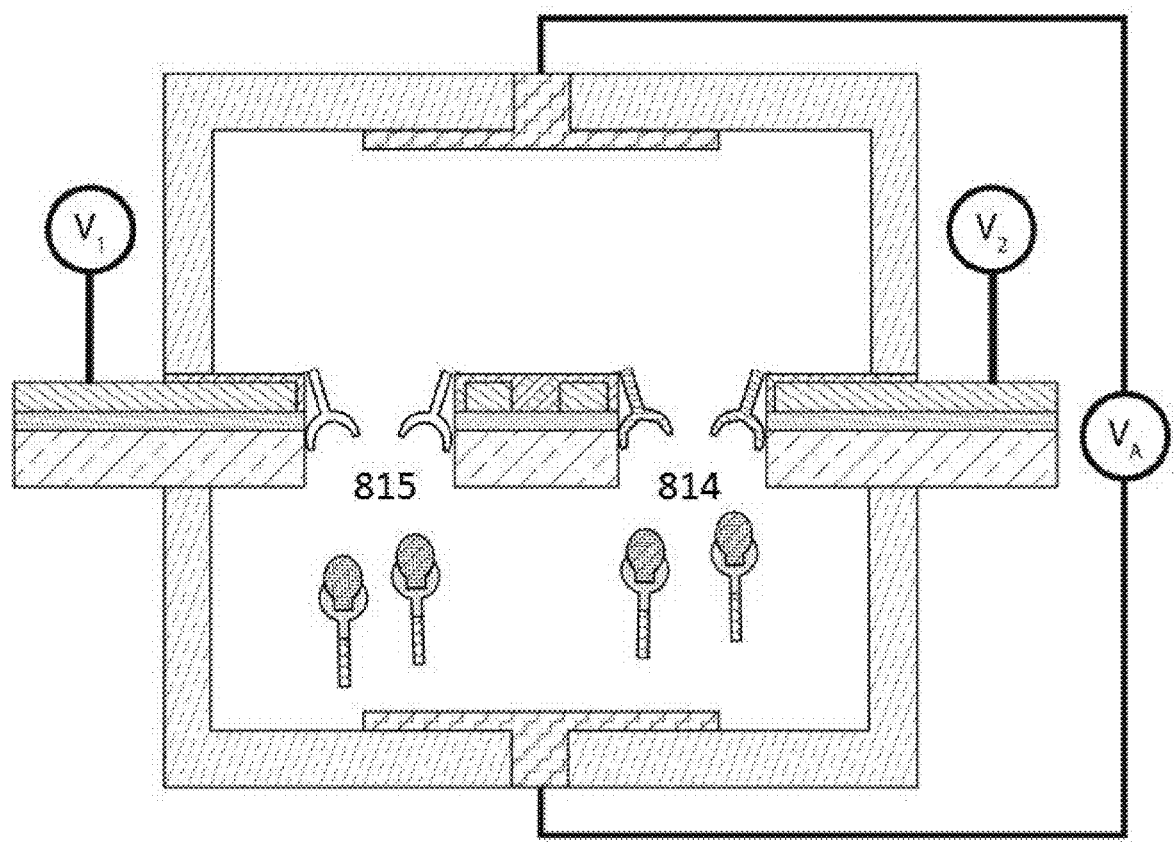
FIG. 8E shows an example of the operation of the apparatus of FIG. 7 at a fourth voltage.

FIG. 8E shows an example of the operation of the apparatus of FIG. 7 at a fourth voltage. The true positives (e.g., specifically bound analytes) can detach 815. The third and/or fourth voltages can be used to determine the binding force between the target antigen and the capture probe.

In some embodiments, the detection of target molecules is based on plasmonics. An example using a surface plasmon resonance imaging setup (SPRI) is provided herein. The gold film of an SPRI chip can be used for one electrode and a conducting film on the bottom of the fluidic cap can be used as a second. In some cases, an electrode for this system may not be transparent.

The methods disclosed herein can be used for probing cross-reactive and non-specific binding events in immunoassays. Non-specific and cross-reactive antibodies may have much lower binding energies than specific antibodies. By applying an electrokinetic force, the approximate binding energy voltage of the molecular pairs can be determined and non-specific and cross-reactive groups can be identified and removed in order to identify the presence of specific antibodies. In some embodiments, the capture probes are antibodies tethered to a polymer chain such as DNA.

In some embodiments, the target analytes are directly detected by the sensor. In such case, cross-reactivity or non-specific binding can occur when a secondary antigen is bound to the surface. The applied electrokinetic force can then act on the analytes themselves, probing the binding strength between the analytes and the capture probe. As the electrokinetic force is increased, the cross-reactive secondary analyte, more weakly bound to the capture probe than the target analyte, can dissociate at a smaller applied electrokinetic force than the target antigen.

In some cases, a sensing or detection antibody is used to enhance the detectability of the antigens. The sensing antibody can be modified to enhance the detectability by the sensor (e.g., by conjugation to a nucleic acid or protein). In embodiments where a sensing antibody is used, possible reactions include, but are not limited to: (a) correct interaction where the capture antibody is attached to the target antigen and the correct sensing antibody, modified or otherwise, binds to the target antigen; (b) a cross-reaction where a secondary antibody binds to the target antigen; (c) a cross-reaction where a secondary antibody binds to the capture antibody; (d) a cross-reaction where a secondary antigen binds to the capture antibody and a secondary antibody binds to the secondary antigen; (e) a secondary antibody binding to the capture antibody in absence of the target antigen; and (f) a secondary antigen binding to the capture antibody and a secondary antibody binds to the secondary antigen. The increasing electrokinetic force can remove the cross-reactive components, such as described in (b)-(f), earlier than the correct interaction, such as described in (a).

Figure 9:
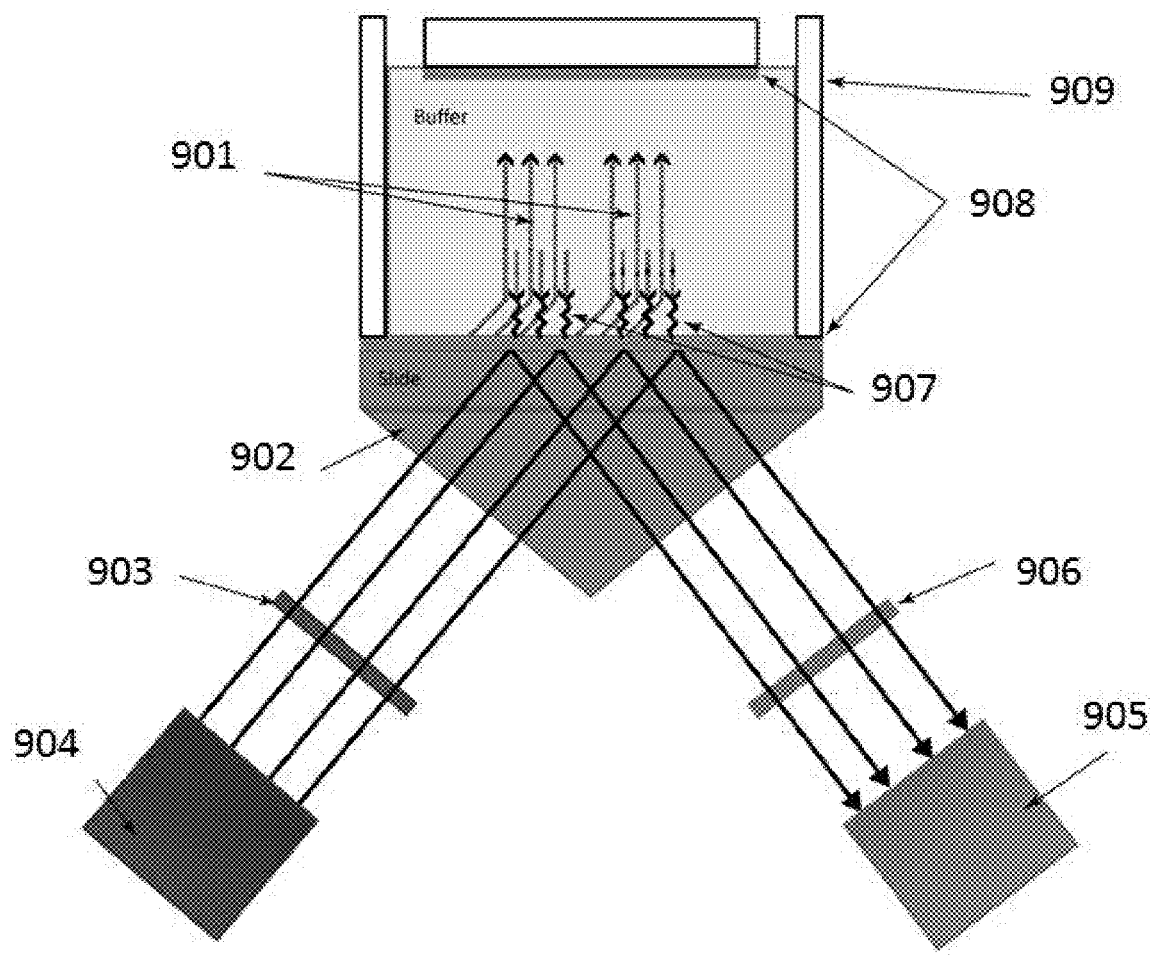
FIG. 9 shows an example of an apparatus of the present disclosure adapted for plasmonic detection of charged analytes.

FIG. 9 shows an example of an apparatus of the present disclosure adapted for plasmonic detection of charged analytes. The apparatus includes charged analytes 901 to be detected, which in this case are nucleic acid molecules. The plasmonic detection system can include a light source 904, a polarizer 903, a prism 902, a metal (e.g., gold) film 908, an optical filter 906 and a detector 905. The charged analytes 901 can be suspended in an electrolyte confined in a fluidic chamber 909. The charged analytes 901 can hybridize to the capture probes 907, thereby becoming detectable by the plasmonic system.

In some embodiments of the present disclosure, the detection of target molecules is based on ionic current blockage of a single pore or porous structure. Some instances of the present disclosure include methods and apparatuses where the applied electrokinetic force is enhanced by the presence of membranes whose thickness ranges from about 0.08 nanometer (nm) to about 1 millimeter (mm). These apparatuses also include one or more electrodes which are embedded within the membrane that are used to sense the presence or absence of the target molecule. In some cases, the embedded electrodes may be used to control the physical location of the capture probes and/or the target molecules. These apparatuses can also include various orifices through which the electrokinetic force is concentrated. These orifices can be any opening in the membrane including pores, slits or gates of various sizes. Via these orifices, the electric field (generating the electrokinetic force) may be directed in any direction. In some cases, the surface of the apparatus is coated with material to change its surface charge in solution, such materials include but are not limited to Silicon Dioxide ($SiO_2$), Silicon Nitride (SiNx), Hafnium Dioxide ($HfO_2$), Zirconium Dioxide ($ZrO_2$), Aluminum Oxide ($Al_2O_3$) and Titanium Dioxide ($TiO_2$).

Figure 10:
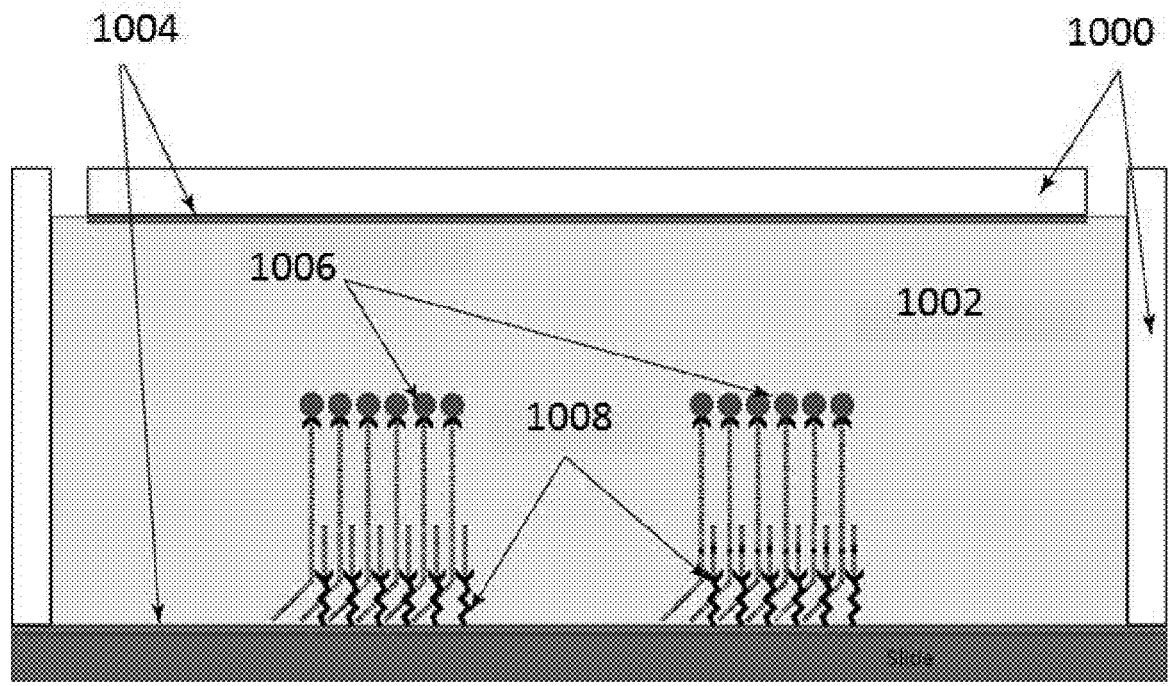
FIG. 10 shows an example of an array of the present disclosure for sensing the presence and binding force of nucleic acid molecules.

FIG. 10 shows an example of an array of the present disclosure for sensing the presence and binding energy of nucleic acid molecules. The system includes a fluidic chamber 1000 containing a buffer 1002 and opposed by a pair of transparent electrodes 1004 capable of creating an electric field. In this case, the field confinement features are not shown. The charged antigens contain fluorescent labels 1006 and can hybridize to the capture probes 1008. Nucleic acids are typically negatively charged, so no secondary charge label may be needed.

Figure 11A:
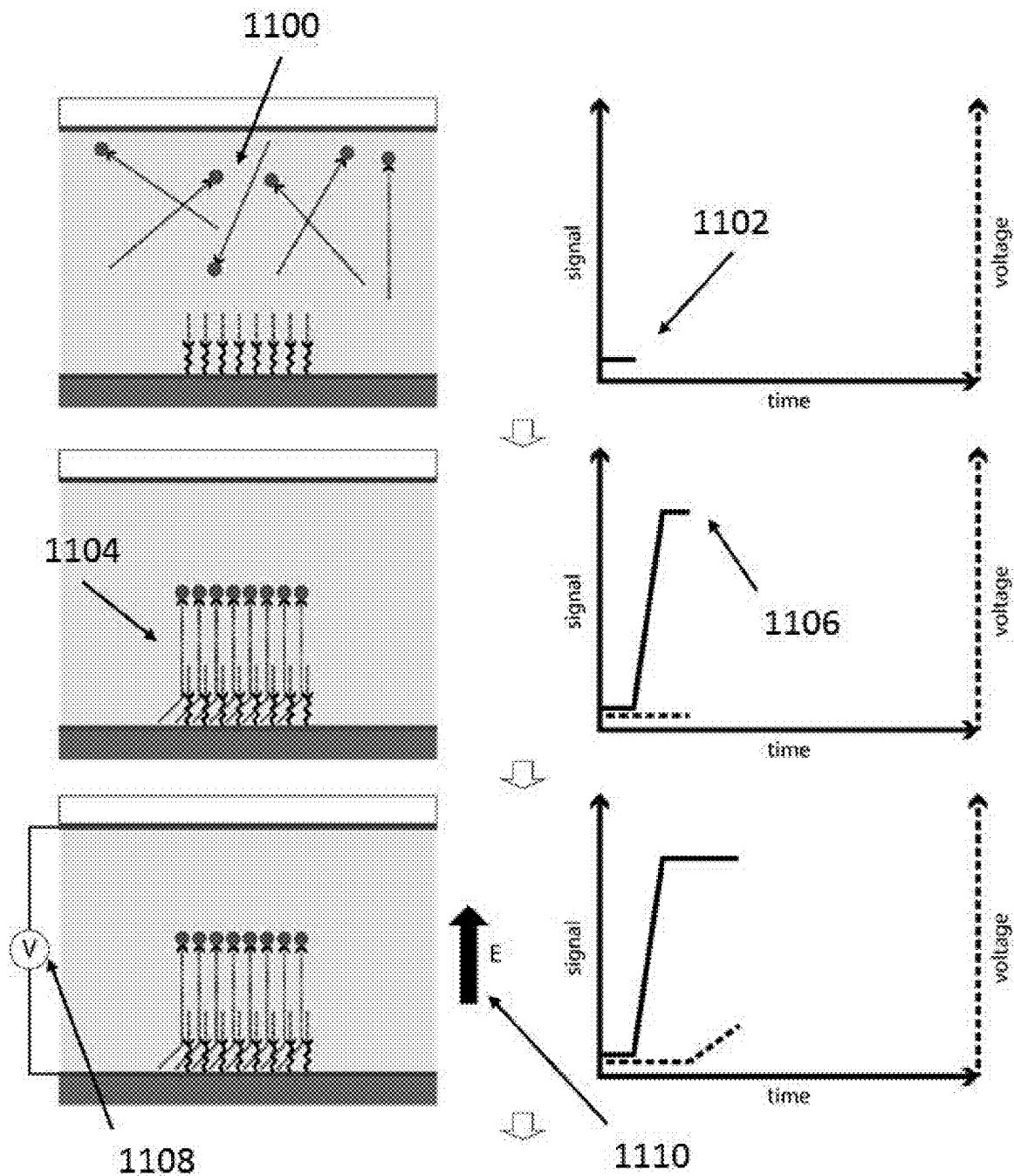
FIG. 11A shows an example of the method of the present disclosure being used to measure the binding force of a complimentary nucleic acid molecule.
Figure 11B:
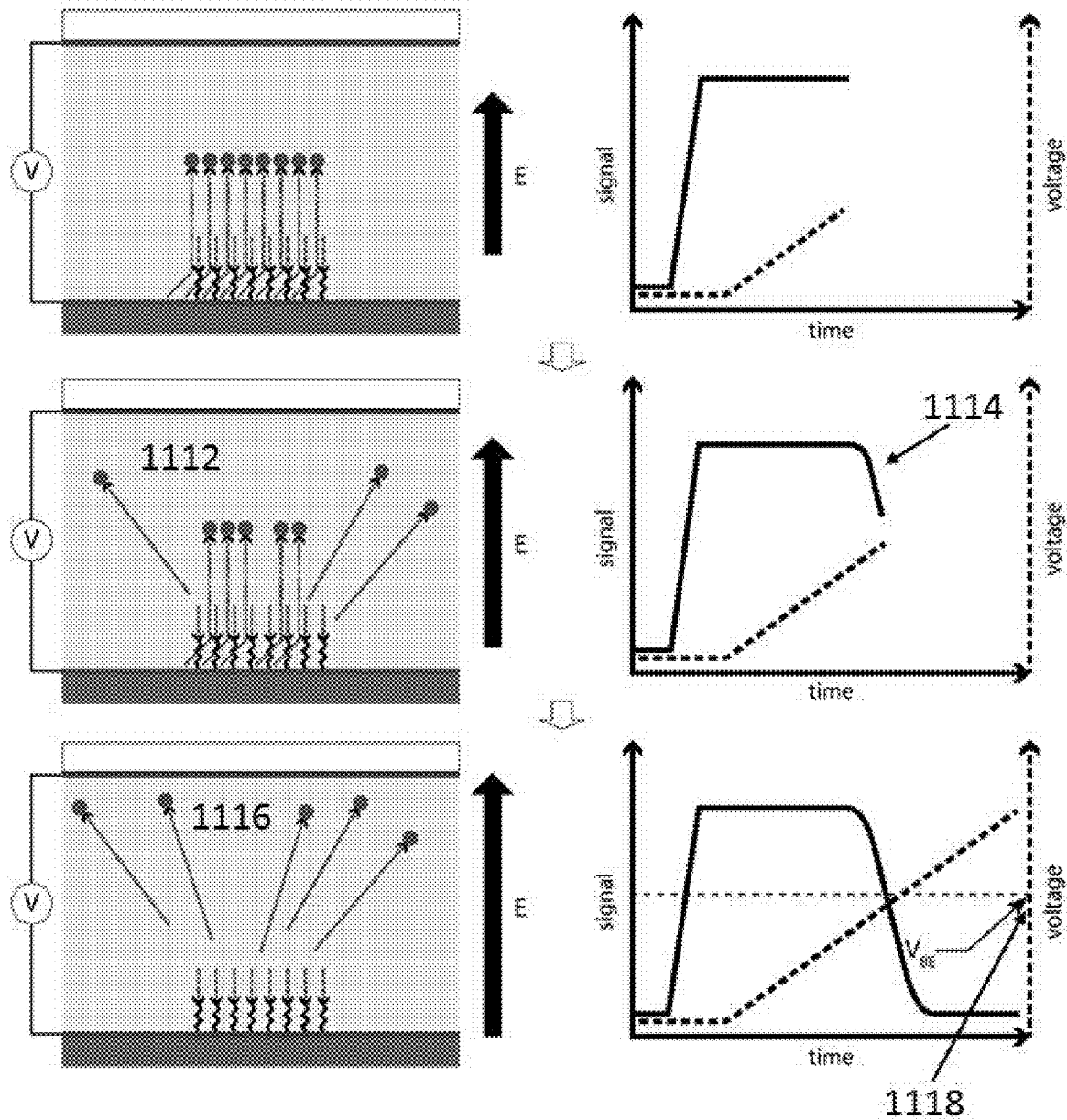
FIG. 11B continues from FIG. 11A and shows an example of the method of the present disclosure being used to measure the binding force of a complimentary nucleic acid molecule.

FIG. 11A shows an example of the method of the present disclosure being used to measure the binding force of a complimentary nucleic acid molecule. The graphic depicts a series of three states of the system (top to bottom) having different relative applied voltages (dashed lines) and fluorescent signals (solid lines). The target analytes are initially not bound to the capture probes 1100 and a baseline signal is detected 1102. The hybridization of the analytes 1104 to the capture probes increases the signal 1106. Application of a linearly increasing applied voltage 1108 creates an electric field 1110 and an applied force on the charged analytes, but does not initially affect the signal. FIG. 11B continues from FIG. 11A and shows the effect of continuing to increase the applied voltage. As the electrokinetic force reaches a level close to the binding force between the analyte and the capture probe, some of the target analytes can dissociate 1112 and the signal can begin dropping 1114. As the voltage continues to increase, eventually all of the analytes can dissociate 1116 and the signal can return to baseline. The binding energy voltage can be defined as the voltage where half of the target analytes are released from the surface 1118. In some cases, the target analyte is bound directly to the capture probe. In some cases, the target analyte is bound indirectly to the capture probe, for example, via a molecular linker as described elsewhere herein.

Figure 12A:
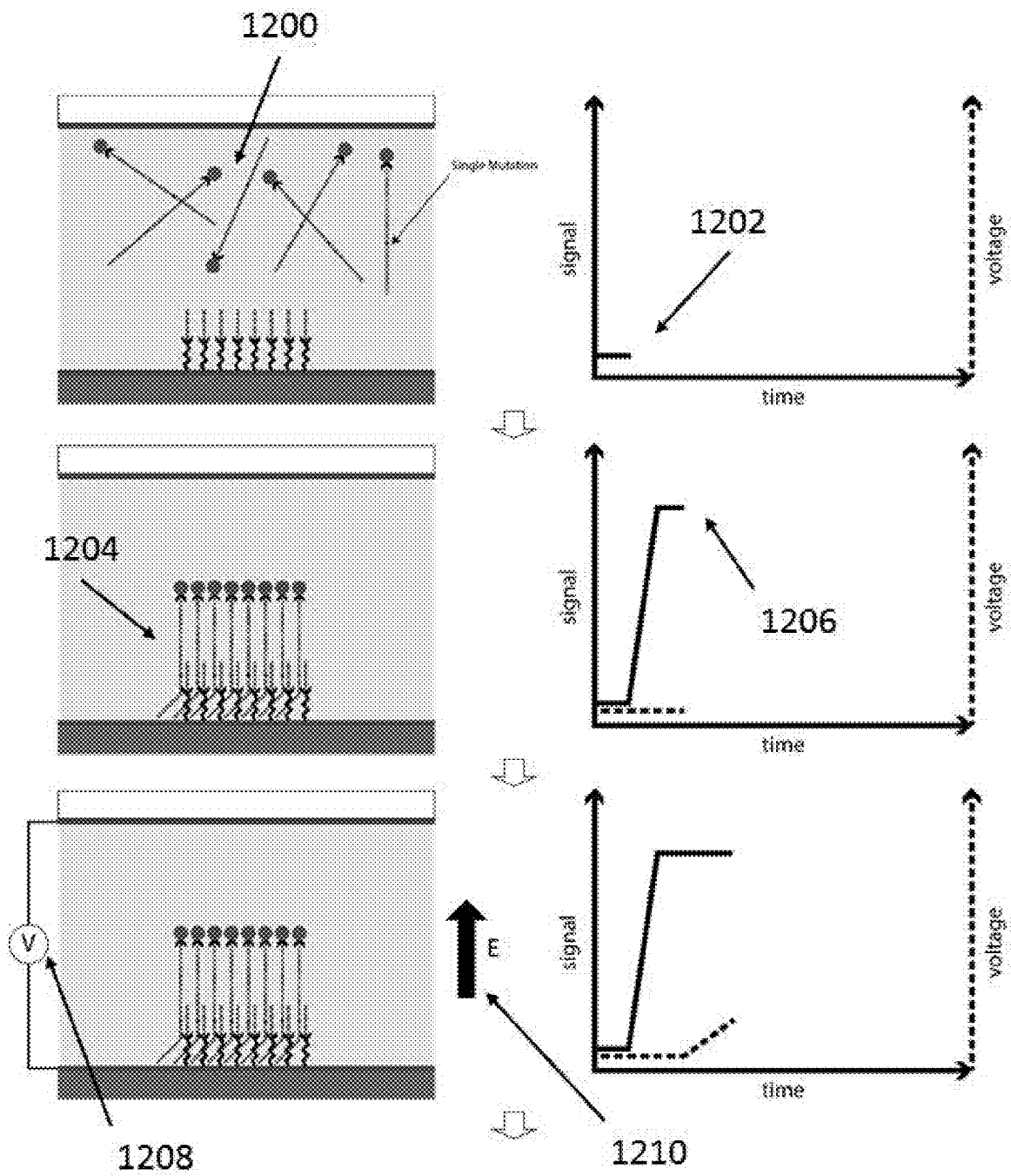
FIG. 12A shows an example of the method of the present disclosure being used to measure the binding force of a nucleic acid molecule having a single base pair mismatch to the capture probe.
Figure 12B:
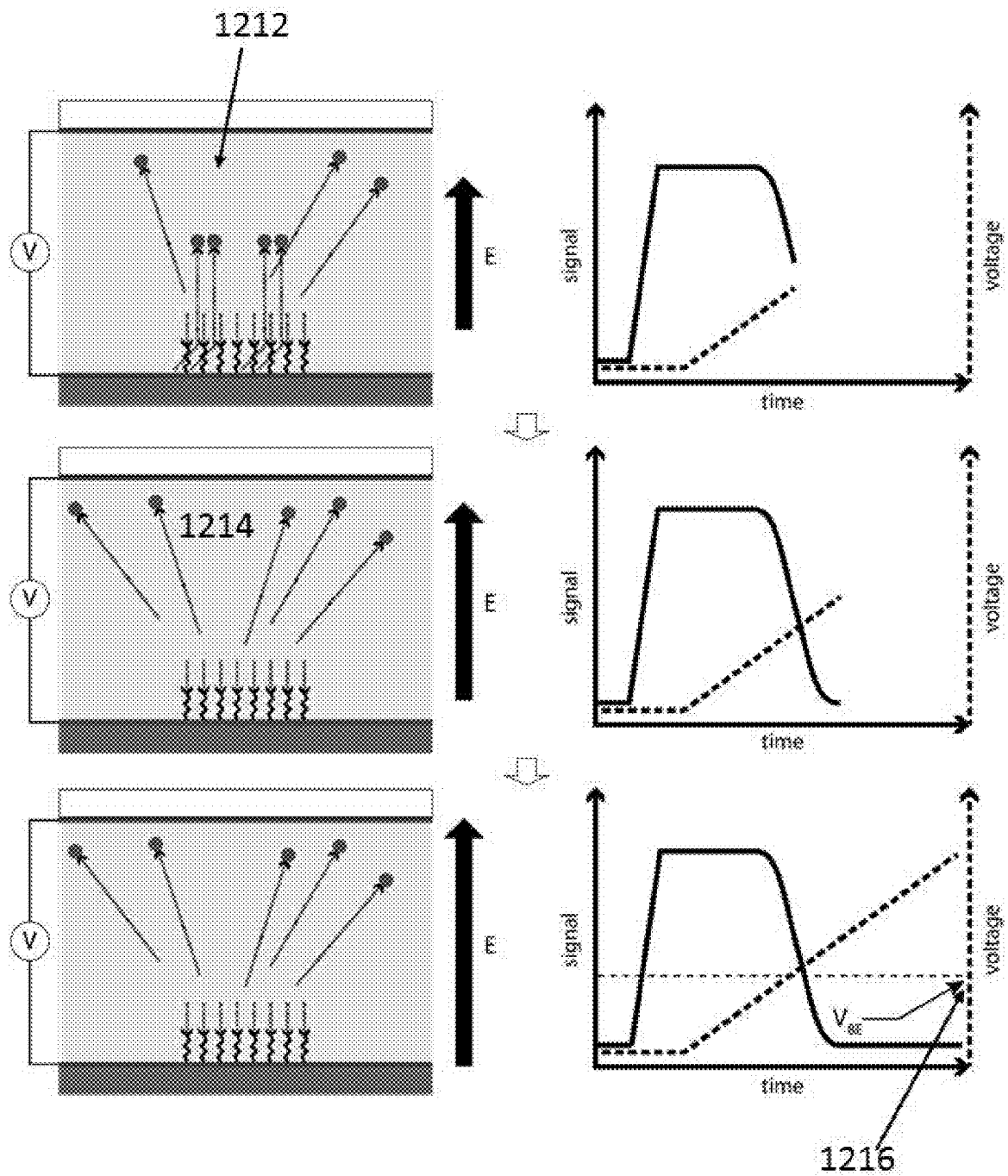
FIG. 12B continues from FIG. 12A and shows an example of the method of the present disclosure being used to measure the binding force of a nucleic acid molecule having a single base pair mismatch to the capture probe.

FIG. 12A and FIG. 12B are similar to FIG. 11A and FIG. 11B, but in this instance show an example of the method of the present disclosure being used to measure the binding force of a nucleic acid molecule having a single base pair mismatch to the capture probe (e.g., a single nucleotide polymorphism (SNP)). The graphic depicts a series of three states of the system (top to bottom) having different relative applied voltages (dashed lines) and fluorescent signals (solid lines). The target analytes are initially not bound to the capture probes 1200 and a baseline signal is detected 1202. The hybridization of the analytes 1204 to the capture probes increases the signal 1206. Application of a linearly increasing applied voltage 1208 creates an electric field 1210 and an applied force on the charged analytes, but does not initially affect the signal. With reference to FIG. 12B, the mismatched analyte dissociates from the capture probe 1212 at a relatively lower voltage compared with the voltage at which a perfectly complimentary analyte dissociates (see 1112 in FIG. 11B). Also, all mismatched analytes dissociate at a relatively lower voltage 1214 and the binding energy voltage 1216 is relatively lower compared with an analyte not having the SNP. The difference in signal versus applied voltage behavior between FIG. 11B and FIG. 12B can be used to identify the presence of the polymorphism. Note that the embodiment described herein is able to distinguish between two or more nucleic acid molecules at a single sensing location using a single capture probe.

Figure 13A:
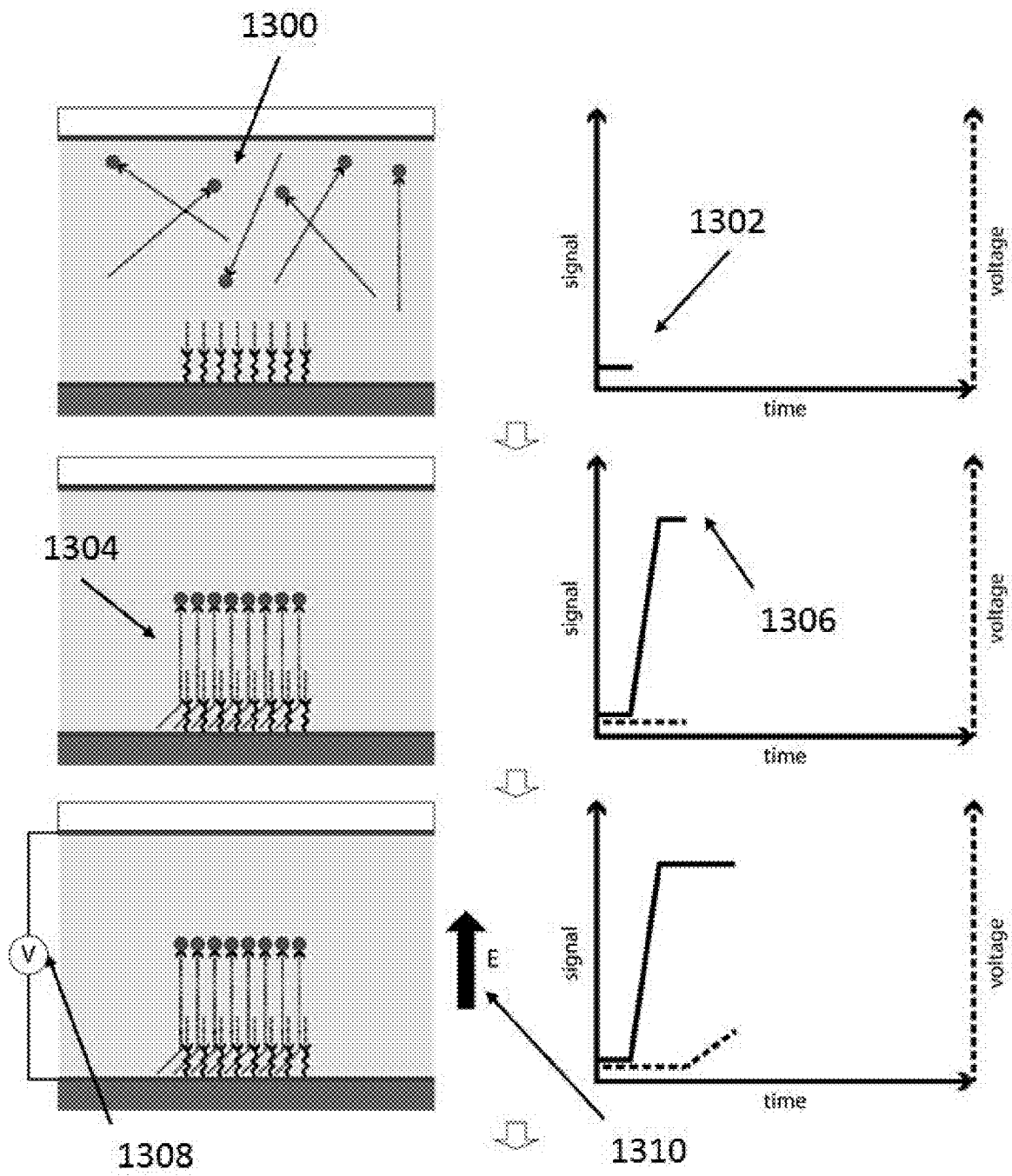
FIG. 13A shows an example of the method of the present disclosure being used to measure the binding force of a mixture of nucleic acid molecules having various amounts of complementarity to the capture probe.
Figure 13B:
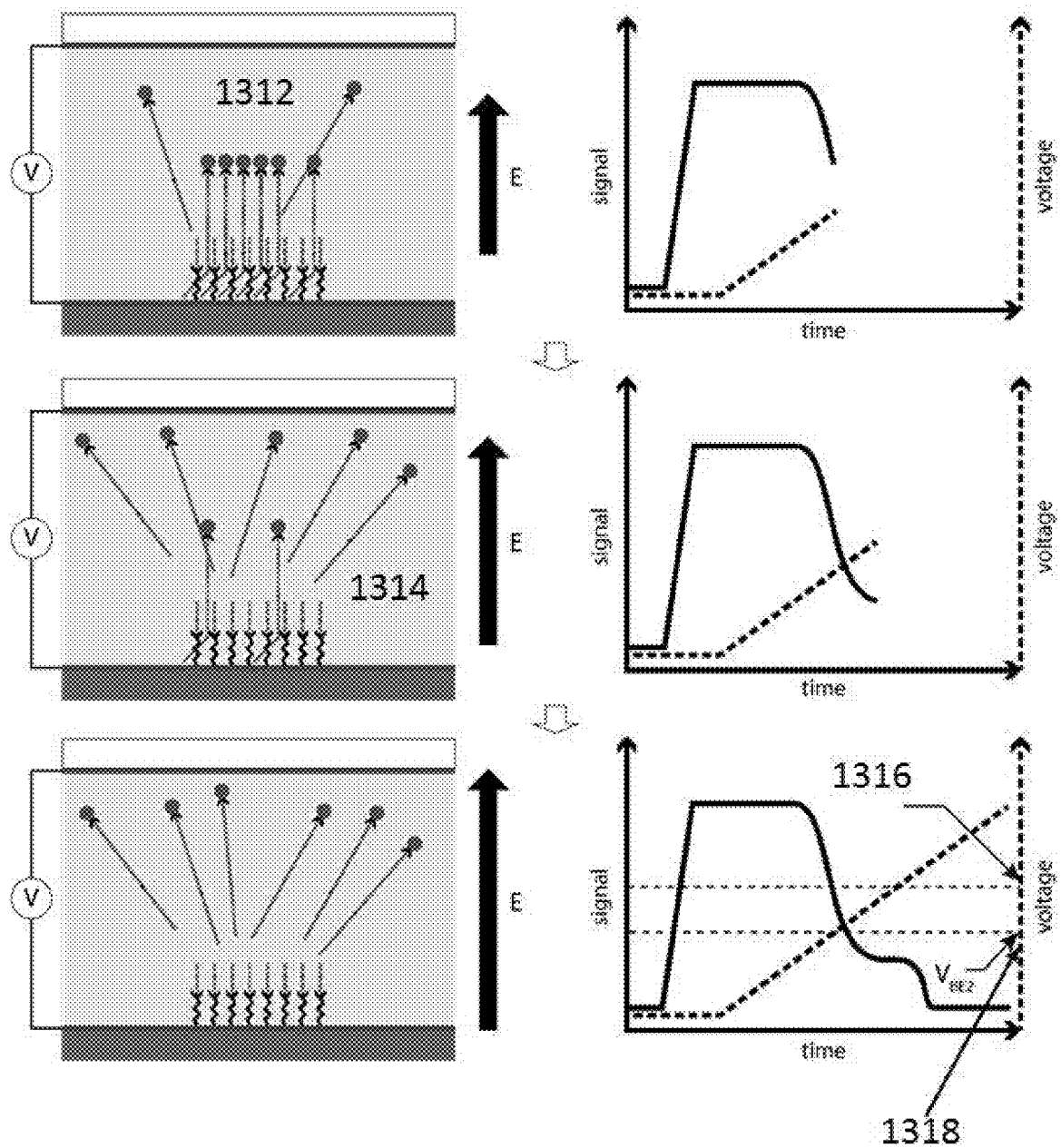
FIG. 13B continues from FIG. 13A and shows an example of the method of the present disclosure being used to measure the binding force of a mixture of nucleic acid molecules having various amounts of complementarity to the capture probe.

The methods described herein can also be used to identify a plurality of different analytes in a mixture. For example, FIG. 13A and FIG. 13B show the method of the present disclosure being used to measure the presence of and/or binding force of a mixture of nucleic acid molecules having various amounts of complementarity to the capture probe. The graphic depicts a series of three states of the system (top to bottom) having different relative applied voltages (dashed lines) and fluorescent signals (solid lines). The target analytes are initially not bound to the capture probes 1300 and a baseline signal is detected 1302. The hybridization of the analytes 1304 to the capture probes increases the signal 1306. Application of a linearly increasing applied voltage 1308 creates an electric field 1310 and an applied force on the charged analytes, but does not initially affect the signal. Turning attention to FIG. 13B, the voltage signal displays two inflection points and two binding energy voltages, 1316 and 1318, corresponding to, first, dissociation of the mismatched nucleic acid analytes 1312 and dissociation of the completely complimentary nucleic acid analytes from the capture probes 1314, respectively.

FIG. 14 shows an example of a multiplexed immunoassay, which depicts the issue of cross reactivity when trying to test for multiple analytes with multiple antibodies. Some instances of the assay use secondary antibodies 1400 that have an attached nucleic acid 1402 (e.g., to increase and control the amount of charge associated with the analyte 1404, which can be bound to a capture probe 1406 tethered to a surface 1408). FIG. 14 shows six different types of cross-reactivity. From left to right, (A, 1409) the molecules can interact correctly, (B, 1410) the secondary antibody can interact with the target analyte (e.g., in a secondary epitope), (C, 1411) the secondary antibody can interact with the capture probe, (D, 1412) the secondary antibody can interact with the capture probe or other entity through an intermediary molecule, (E, 1413) the secondary antibody can interact with the capture probe without the analyte, and (F, 1414) the wrong analyte can be bound by the capture probe and/or the secondary antibody. These are non-limiting examples. The methods of the present disclosure use an applied electrokinetic force to resolve such issues by pulling apart such non-specific interactions.

Figure 15:
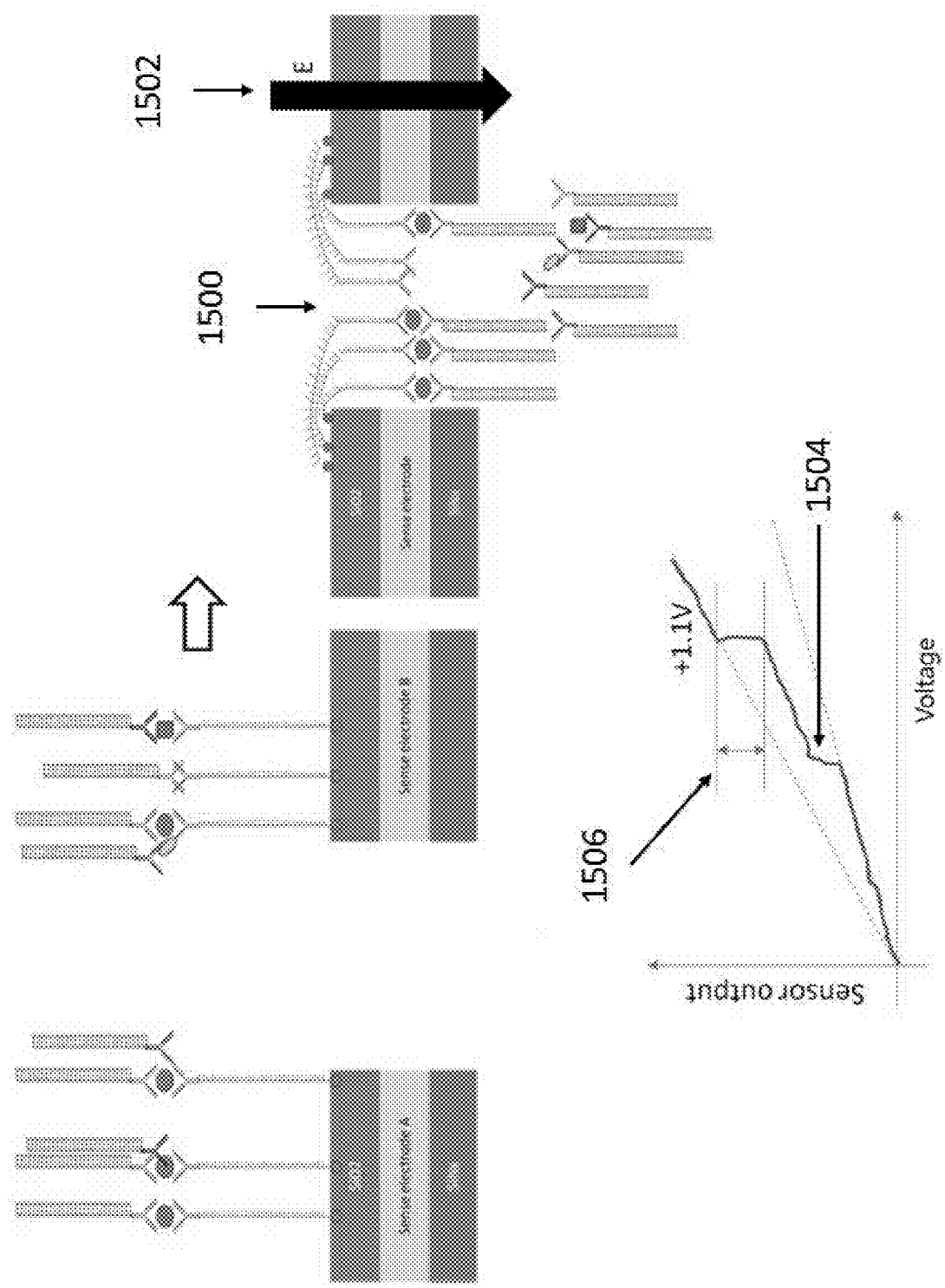
FIG. 15 shows an example of performing the method of the present disclosure using the apparatus shown in FIG. 14.

FIG. 15 shows an example of performing the method of the present disclosure using the apparatus shown in FIG. 14. The various types of correct and non-specifically interacting molecules can be pulled into the sensing orifice 1500 by an applied electric field 1502. A plot of sensor output versus applied voltage shows detachment of non-specific binding 1504, followed by an actual signal 1506 associated with the disruption of the binding of the correctly bound target analyte.

Figure 16:
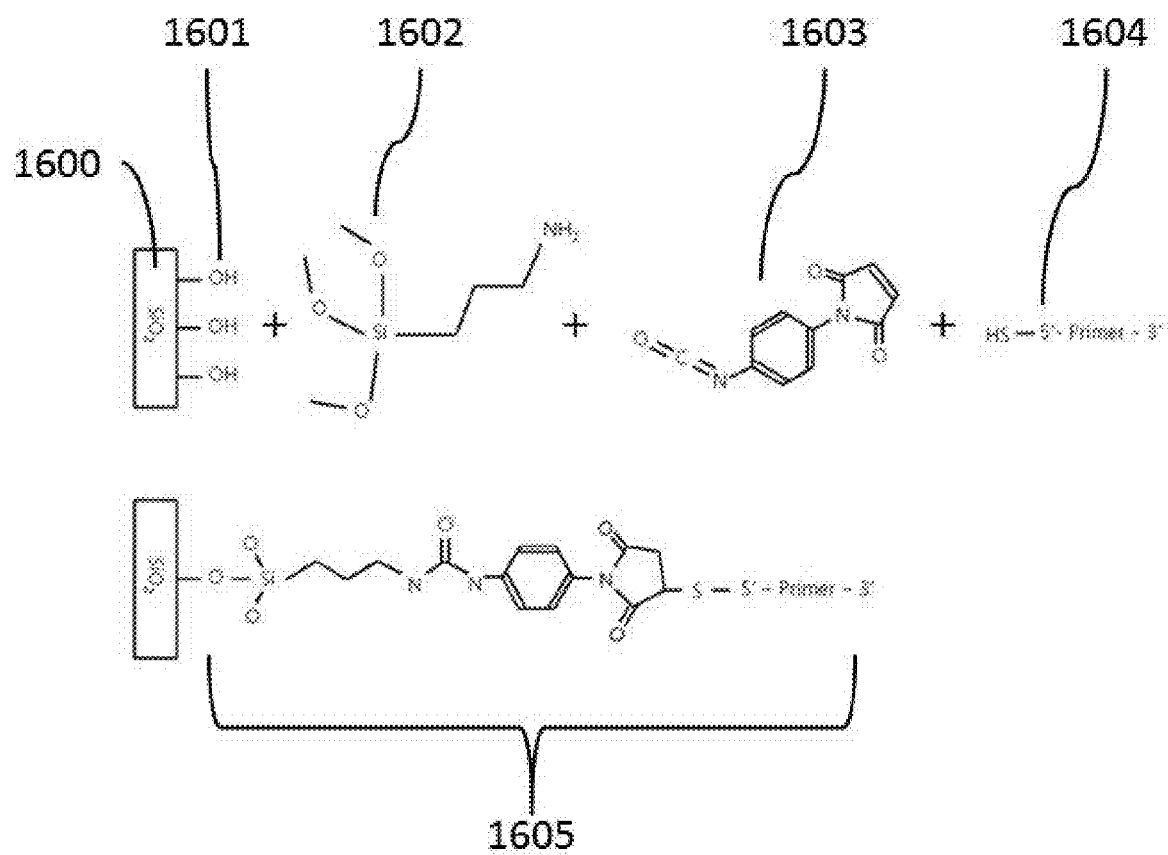
FIG. 16 shows an example of the attachment of a nucleic acid molecule to a surface of the present disclosure.

FIG. 16 shows an example of a process of covalently attaching the capture probe (e.g., nucleic acids) to the surface. A $SiO_2$ surface 1600 comprising hydroxide moieties 1601 (and/or that is hydroxylated) can be silanized (e.g., using aminosilane 1602). Silanization can be performed in gas phase. A crosslinker (e.g., PMPI 1603) can be used to connect the amine group on the silane and the sulfhydryl group of the 5' thiol-modified primer 1604. The resulting product of the surface chemistry described herein is shown at 1605.

In practice, sensors can be plasma cleaned, rehydrated and functionalized with (3-aminopropyl)-trimethoxysilane (APTMS) using a chemical vapor deposition system. The amino-functionalized surfaces can be subsequently transformed into a thiol-reactive moiety by exposure to a 2.3 mM solution of N-(p-maleimidophenyl) isocyanate (PMPI) in anhydrous toluene at 40° C. for 2 hours under an argon atmosphere. The surfaces can be subsequently washed with anhydrous toluene and dried in a stream of argon followed by DNA immobilization using thiolated oligonucleotides. Prior to immobilization, the thiolated oligos can be reduced using tris(2-carboxyethyl)phosphine (TCEP) as a reducing agent and desalted using a spin column (MWCO=3000). Thiolated oligos can be spotted directly onto sensing chips for 6 hours at 10 µM concentration in a 1M NaCl buffer solution under a controlled atmosphere, followed by extensive washing. The various surface modification steps can be followed by x-ray photoelectron spectroscopy and the presence of the expected elements and peak shifts confirmed the transformation of the sensing surface. The presence of immobilized nucleic acid can be verified by fluorescence microscopy with appropriately excited SYBR Gold nucleic acids dye. Subsequently, the immobilized oligonucleotides can be used to further increase the pool of possible surface modifications by introducing probes conjugated to the complementary strand of the immobilized nucleic acid. Additional details pertaining to fabrication or operation of the devices described herein can be found in International Patent Application Publication No. WO2015196148, which is incorporated herein in its entirety for all purposes.

In some cases, the capture probe is a protein such as, but not limited to, an antibody. The protein can be attached to the surface using any suitable approach, such as attachment through cysteine residues or through unnatural amino acids having reactive functionality. In some cases, the protein is attached by the SiteClick™ chemistry as described in U.S. Patent Application Publication No. 20150246146, which is incorporated herein by reference in its entirety. In such cases, the protein is attached to the surface via its carbohydrate groups (i.e., glycosylation sites). In the case of antibodies, glycosylation sites can occur on the constant region (i.e., Fc) of the antibody. In many cases, attachment via the Fc region of an antibody minimally alters or affects the binding region of the antibody, allowing the binding specificity of the antibody to be mostly, if not completely, preserved. This attachment procedure can comprise three operations. First, terminal N-acetylglucosamine (GlcNAc) residues are exposed, for example by removing terminal galactose residues using the enzyme beta-galactosidase. A reactive azide group can be added to the GlcNAc, for example by adding the sugar N-azidoacetylgalactosamine-tetraacylated (GalNAz) by the enzyme beta-galactosyltransferase (GalT). An alkyne group can react with the azide group (referred to as click chemistry) to form a covalent linkage between the protein and the surface, for example by reaction with the dibenzocyclooctyne (DIBO) reagent which is attached to the surface (e.g., in proximity to the pore).

Figure 28:
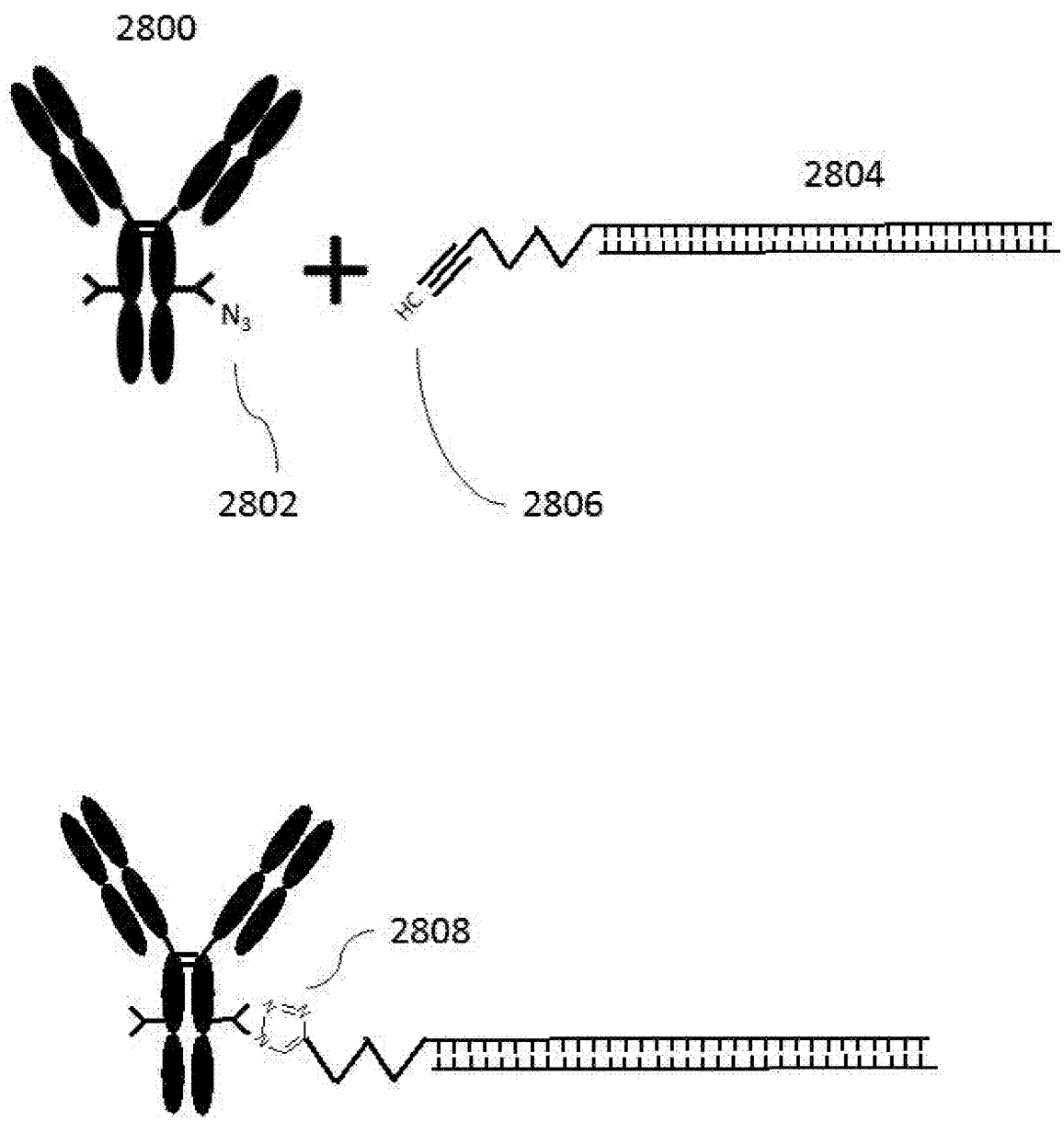
FIG. 28 shows an example of linking an antibody to a nucleic acid molecule.

FIG. 28 shows an example of chemistry for linking an antibody to a nucleic acid molecule (which can be tethered to a surface). As shown, the antibody 2800 has an azide group 2802 and the nucleic acid molecule 2804 has an alkyne group 2806. These groups can be reacted to form a covalent linkage 2808 (e.g., cycloaddition) between the antibody and the nucleic acid molecule.

In some embodiments, the linking chemistry described above has a relatively low efficiency in that a low amount of antibody becomes linked to the nucleic acid molecule. In some cases, this can be overcome by providing the antibody or the nucleic acid molecule in excess, e.g., at least about 5-fold, at least about 10-fold, at least about 20-fold, at least about 50-fold or at least about 100-fold excess. However, inefficient use of reagent can increase the cost associated with the linking step.

The linking of a molecule to a surface as described in methods herein may exhibit a range of efficiencies. In some cases, the efficiency is at least about 10%, at least about 20%, at least about 30%, at least about 40%, at least about 50%, at least about 60%, at least about 70%, at least about 80%, or at least about 90%. For example, upon completion of the linking step, at least 10%, at least about 20%, at least about 30%, at least about 40%, at least about 50%, at least about 60%, at least about 70%, at least about 80%, or at least about 90% of the molecule (e.g., antibody) is linked to the surface. In some cases, high efficiencies (e.g., efficiencies greater than 60%, 70%, 80%, or 90%) can be achieved by use of a linker having a dibenzocylcyooctyne (DIBO) and maleimide moiety to couple the molecule (e.g., antibody) to the surface (e.g., nucleic acid molecule and/or surface, e.g., chip surface, sensor surface). In some cases, the efficiency achieved using a linker having a DIBO and maleimide moiety is at least about 10%, at least about 20%, at least about 30%, at least about 40%, at least about 50%, at least about 60%, at least about 70%, at least about 80%, or at least about 90%.

In an aspect, the present disclosure provides a method for coupling a target molecule to a surface such as a sensor surface. The method can include providing a sensor surface comprising a thiol group, a target molecule comprising an azide group, and a linker molecule comprising a maleimide moiety and strained triple bond. In some cases, the sensor surface comprises a nucleic acid molecule having a thiol group. Such nucleic acids can be produced by a variety of methods, including, for example polymerase chain reaction (PCR). The strained triple bond can be part of a cyclooctyne ring. In some embodiments, the cyclooctyne ring is part of a dibenzocyclooctyne (DIBO) group.

The linker molecule can be reacted with the sensor surface and with the target molecule such that the azide group of the target molecule and the strained triple bond of the linker molecule undergo cycloaddition, and the thiol group of the sensor surface forms a covalent bond with the maleimide moiety of the linker molecule, thereby coupling the target molecule to the sensor surface via the linker molecule.

Figure 29:
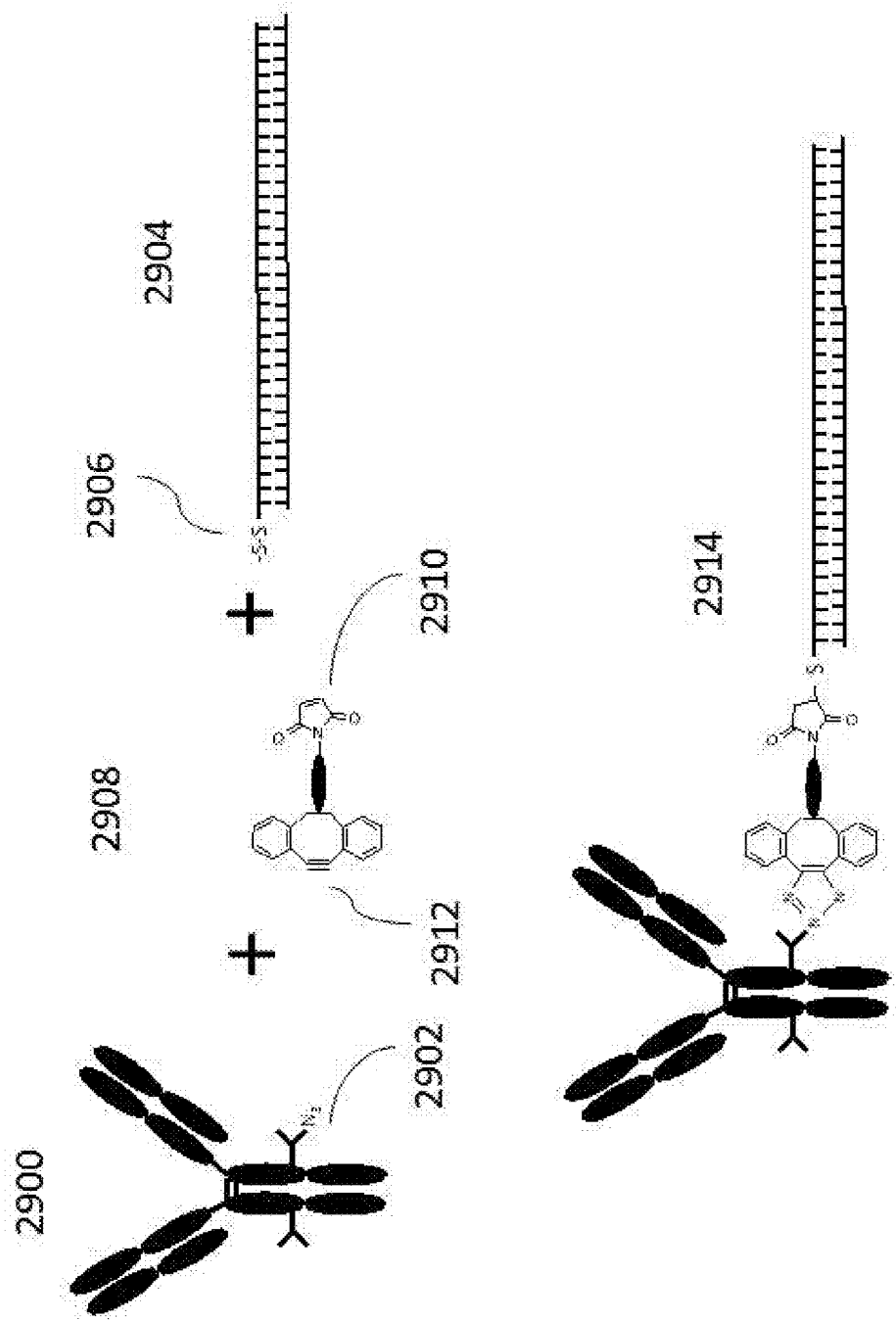
FIG. 29 shows an example of linking an antibody to a nucleic acid molecule using a bifunctional linker.

With attention to FIG. 29, an antibody 2900 comprising an azide group 2902 can be coupled with a nucleic acid molecule 2904 comprising a thiol group 2906 using a linker molecule 2908 comprising a maleimide moiety 2910 and a strained triple bond 2912. The reaction can result in the linkage of the antibody with the nucleic acid molecule 2914. In some embodiments, the reaction is not catalyzed by copper.

In some instances, the linker is reacted simultaneously with the sensor surface and the molecule. In some cases, the linker is reacted with the sensor surface prior to being reacted with the target molecule. In some embodiments, the linker is reacted with the sensor surface subsequent to being reacted with the target molecule.

The target molecule to be coupled to the sensor surface can be a nucleic acid molecule. The target molecule to be coupled to the sensor surface can be an antibody. In some embodiments, the azide group of the antibody is not in proximity to a binding region of the antibody. For example, the azide group is not on a variable region of the antibody. In some cases, the azide group is located on a constant region, e.g., an Fc region, of the antibody.

The azide group can be added to an antibody by any of a variety of methods. In some cases, the azide group can be added to the antibody at least in part by (a) removing terminal galactose residues of terminal N-acetylglucosamine (GlcNAc) residues using the enzyme beta-galactosidase and (b) incorporating a N-azidoacetylgalactosamine-tetraacylated (GalNAz) which contains the azide group into the antibody using a beta-galactosyltransferase (GalT), thereby adding the azide group to the antibody.

The sensor surface can be part of any sensor described in the present disclosure. In some embodiments, the sensor surface is part of a sensor that comprises a plurality of electrodes capable of applying an electric field. The methods described herein can also be used to link any two molecules together (e.g., not to a surface). In some cases therefore, the surface described herein is a second molecule in solution.

Figure 17:
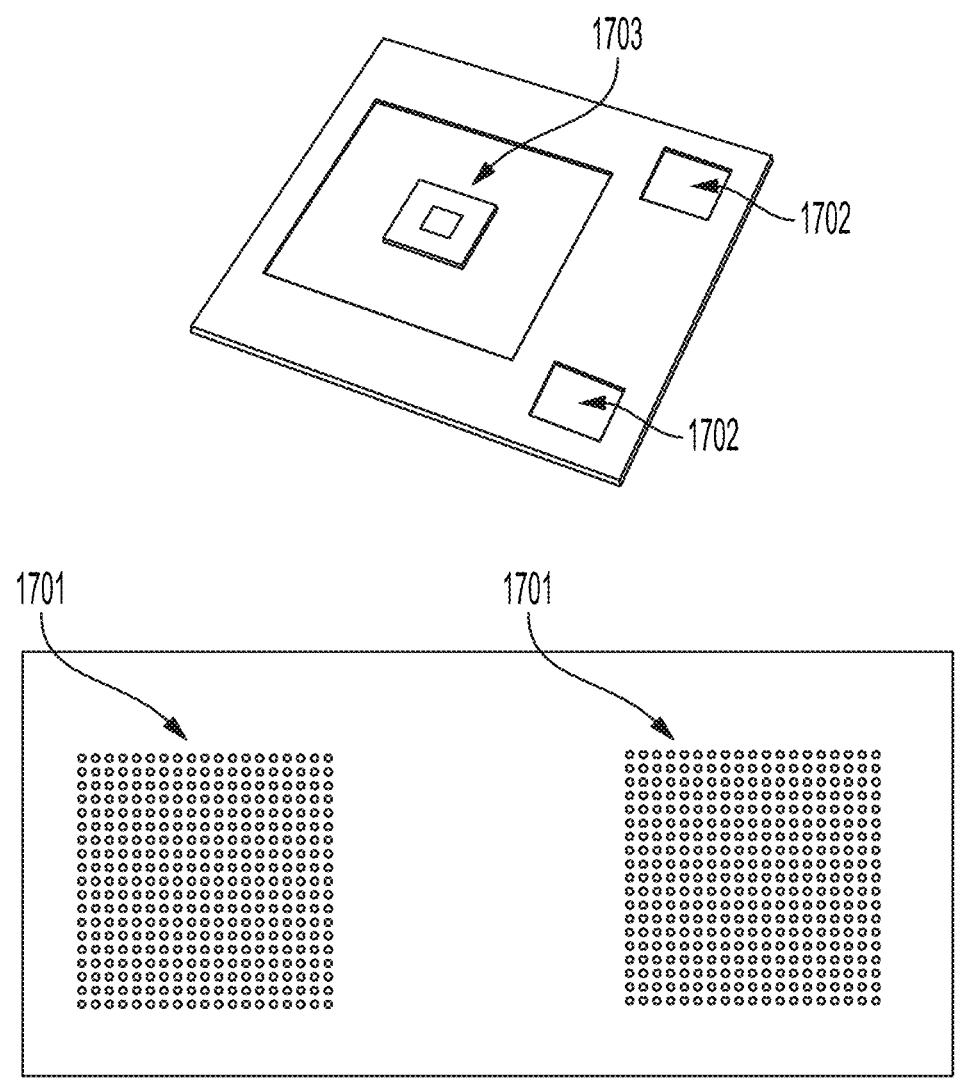
FIG. 17 shows an example of an apparatus of the present disclosure.

FIG. 17 shows an example of an apparatus of the present disclosure, including a fluorescence microscopy image 1701 of TAMRA (5-carboxytetramethylrhodamine) labeled oligonucleotides in an array of wells for concentrating electric fields, transparent indium tin oxide electrodes 1702, and a field terminating metal plate of platinum surrounding the array of wells 1703.

Figure 18:
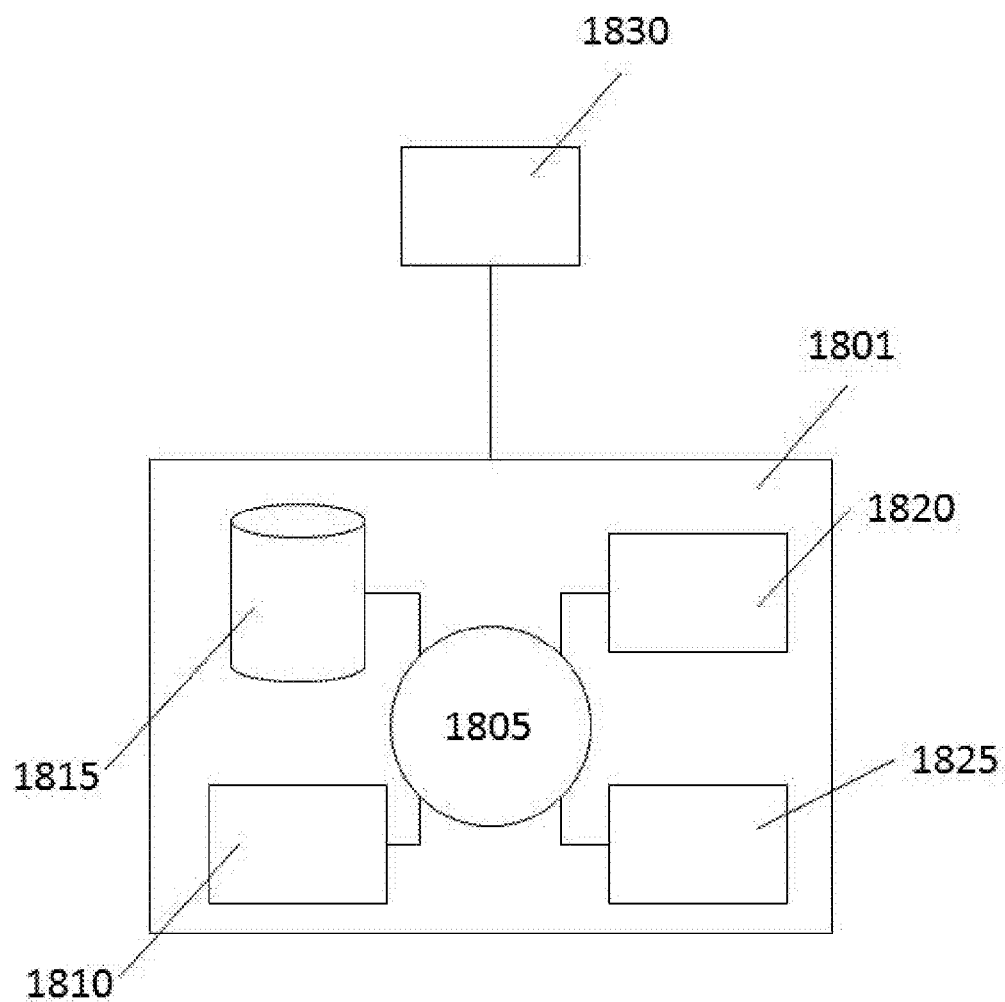
FIG. 18 shows an example of a computer system for operation of the apparatus of the present disclosure.

FIG. 18 shows a computer system 1801 that is programmed or otherwise configured to regulate the operation of the apparatus of the present disclosure. The computer system 1801 can regulate, for example, flow rates, temperatures, pressures, mechanical manipulations, applied voltages or other electrical inputs and/or outputs, and the like.

The computer system 1801 includes a central processing unit (CPU, also "processor" and "computer processor" herein) 1805, which can be a single core or multi core processor, or a plurality of processors for parallel processing. The computer system 1801 also includes memory or memory location 1810 (e.g., random-access memory, read-only memory, flash memory), electronic storage unit 1815 (e.g., hard disk), communication interface 1820 (e.g., network adapter) for communicating with one or more other systems, and peripheral devices 1825, such as cache, other memory, data storage and/or electronic display adapters. The memory 1810, storage unit 1815, interface 1820 and peripheral devices 1825 are in communication with the CPU 1805 through a communication bus, such as a motherboard. The storage unit 1815 can be a data storage unit (or data repository) for storing data.

The CPU 1805 can execute a sequence of machine-readable instructions, which can be embodied in a program or software. The instructions may be stored in a memory location, such as the memory 1810. Examples of operations performed by the CPU 1805 can include fetch, decode, execute, and writeback.

The storage unit 1815 can store files, such as drivers, libraries and saved programs. The storage unit 1815 can store programs generated by users and recorded sessions, as well as output(s) associated with the programs. The storage unit 1815 can store user data, e.g., user preferences and user programs. The computer system 1801 in some cases can include one or more additional data storage units that are external to the computer system 1801, such as located on a remote server that is in communication with the computer system 1801 through an intranet or the Internet.

The computer system 1801 can be in communication with a system 1830, including a device with integrated fluidics and/or process elements. Such process elements can include sensors, flow regulators (e.g., valves), and pumping systems that are configured to direct a fluid.

Methods as described herein can be implemented by way of machine (e.g., computer processor) executable code stored on an electronic storage location of the computer system 1801, such as, for example, on the memory 1810 or electronic storage unit 1815. The machine executable or machine readable code can be provided in the form of software. During use, the code can be executed by the processor 1805. In some cases, the code can be retrieved from the storage unit 1815 and stored on the memory 1810 for ready access by the processor 1805. In some situations, the electronic storage unit 1815 can be precluded, and machine-executable instructions are stored on memory 1810.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

An aspect of the present disclosure provides an apparatus for detecting a presence of an analyte, comprising: (a) a fluidic chamber adapted to contain an electrolyte; (b) two or more electrodes capable of generating an electric field within the fluidic chamber; (c) at least one surface comprising an immobilized capture probe capable of binding the analyte, wherein the at least one surface is between the two or more electrodes and in contact with the fluidic chamber, and wherein the at least one surface comprises an electrically conducting layer and an electrically insulating layer; and (d) at least one field confining feature proximal to the at least one surface, which at least one field confining feature is capable of concentrating an electric field surrounding the at least one field confining feature to a strength of at least about $10^3$ volts per meter (V/m). In some cases, the analyte is a charged analyte. The analyte can be charged directly, or indirectly by binding to a charged molecule such as a charged antibody. The apparatus can further comprise a controller operably coupled to the two or more electrodes, where the controller is programmed to apply a voltage across the two or more electrodes that is sufficient to generate an applied force on the analyte.

The at least one field confining feature can be capable of concentrating the electric field surrounding the at least one field confining feature to any suitable strength. In some cases, the field strength is at least about $10^3$ volts per meter (V/m), at least about $10^4$ V/m, at least about $10^5$ V/m, at least about $10^6$ V/m or at least about $10^7$ V/m. In some cases, the field strength is at most about $10^3$ V/m, at most about $10^5$ V/m, at most about $10^7$ V/m, or at most about $10^9$ V/m.

The voltage applied can sufficient to generate any suitable applied force on the charged analyte. In some cases, the applied force is at least about 1 piconewton (pN), at least about 5 pN, at least about 10 pN, at least about 20 pN, at least about 50 pN, at least about 100 pN, at least about 500 pN, at least about 1000 pN or at least about 5000 pN on the analyte. In some instances, the applied force is at most about 1 piconewton (pN), at most about 5 pN, at most about 10 pN, at most about 20 pN, at most about 50 pN, at most about 100 pN, at most about 500 pN, at most about 1000 pN or at most about 5000 pN on the analyte.

The immobilized capture probe can be capable of binding to the analyte to form a probe-analyte complex on the at least one surface. The immobilized capture probe can be capable of binding to the analyte via non-covalent interaction(s). In some cases, the analyte is bound to the capture probe via a molecular linker. The non-covalent interaction(s) can be disrupted through an applied force generated upon the application of a voltage across the two or more electrodes.

In some cases, the immobilized capture probe is proximal to the at least one field confining feature. For example, the capture probe can be immobilized within about 10 nanometers (nm), within about 20 nm, within about 50 nm, within about 100 nm, within about 500 nm, or within about 1000 nm of the field confining feature.

The at least one field confining feature can be a plurality of field confining features. For example, the surface can have at least about 5, at least about 10, at least about 50, at least about 100, at least about 500, at least about 1000, at least about 5000, at least about 10000, at least about 50000, at least about $10^6$, or at least about $10^7$ field confinement features.

In some cases, the immobilized capture probe is an antibody. In some instances, the analyte is an antigen. In some cases, the immobilized capture probe is a nucleic acid molecule. In some instances, the analyte is a nucleic acid molecule.

Note that the use of the term "immobilized" does not mean that the capture probe cannot move. For example, the capture probe can be tethered to the surface at one or more locations and move within the electrolyte due to fluid flow or other forces.

The analyte can have any suitable charge (e.g., in order to provide an adequate applied force). In some cases, the analyte has a charge of at least about 1 $e^-$, at least about 10 $e^-$, at least about $10^2$ $e^-$, at least about $10^3$ $e^-$, at least about $10^4$ $e^-$, at least about $10^5$ $e^-$ or at least about $10^6$ $e^-$. In some cases, the analyte has a charge of at most about 1 $e^-$, at most about 10 e, at most about $10^2$ $e^-$, at most about $10^3$ $e^-$, at most about $10^4$ $e^-$, at most about $10^5$ $e^-$ or at most about $10^6$ $e^-$. Note that the analyte can have a positive charge or a negative charge. Positive charges of a similar magnitude to those disclosed herein are also encompassed by the present disclosure.

The apparatus can further include a controller operably coupled to the two or more electrodes, where the controller is programmed to apply a potential difference of less than about 100 volts (V) between the two or more electrodes. In some cases, the applied voltage is less than about 50 V, less than about 10 V, less than about 5 V, or less than about 1 V. In some instances, the applied voltage is greater than about 50 V, greater than about 10 V, greater than about 5 V, or greater than about 1 V.

The at least one surface can provide a wall of the fluidic chamber (as shown in FIG. 1A) and the field confining feature is an orifice in the surface. In some cases, the field confining feature comprises an orifice in the at least one surface. In some cases, the fluidic chamber comprises a top portion and a bottom portion partitioned by the at least one surface, and wherein the field confining feature is an orifice in the at least one surface (as shown in FIG. 1C). In some cases, the orifice extends through the surface. The orifice can be, without limitation, an indentation, a well, a pore, a channel, a gap, or a slit. The field confining feature can be any shape, including circular, oval, square, rectangular, or any polygon.

The field confining feature can have any suitable diameter. In some cases, the diameter is less than about 50 micrometers, less than about 10 micrometers, less than about 5 micrometers, less than about 1 micrometer, less than about 500 nanometers, less than about 100 nanometers, or less than about 50 nanometers. In some cases, the diameter is greater than about 50 micrometers, greater than about 10 micrometers, greater than about 5 micrometers, greater than about 1 micrometer, greater than about 500 nanometers, greater than about 100 nanometers, or greater than about 50 nanometers.

The field confining feature can have any suitable aspect ratio. In some cases, the aspect ratio is the ratio of the longest dimension of the field confining feature to the shortest dimension of the field confining feature. In some instances, the aspect ratio is the ratio of the width of the field confining feature to the depth of the field confining feature. Without limitation, the field confining feature can have an aspect ratio of at least about 0.1, at least about 0.5, at least about 1, at least about 2, at least about 3, at least about 5, at least about 10, at least about 50, at least about 100, or more. The field confining feature can have a sharp edge (e.g., having an angle of at least about 60 degrees). The field confining feature can be an elevated portion of the at least one surface.

The electrically conducting layer can be in communication with the electrolyte, such as physically contacting or in electrical communication. The electrically conducting layer can be electrically isolated from the electrolyte, and wherein, during use, the electrically conducting layer is electrically biased. The electrically conducting layer can comprise any suitable metal, such as platinum, copper, gold or silver.

The apparatus can further comprise a sensing electrode configured to measure a charge signal associated with the presence of the analyte. The sensing electrode can be proximal to the at least one field confining feature (e.g., within about 10 nanometers (nm), within about 20 nm, within about 50 nm, within about 100 nm, within about 500 nm, or within about 1000 nm of the field confining feature).

The apparatus can further comprise a light source and a detector configured to detect an optical signal associated with the presence of the analyte. The optical signal can be a fluorescence signal. In some cases, the fluorescence signal is a fluorescence resonance energy transfer, FRET, signal. The fluorescence signal can be provided by a fluorescent probe covalently or non-covalently attached to the analyte.

The apparatus can further comprise a detector configured to detect a surface plasmon resonance signal associated with the presence of the analyte.

The at least one surface can be substantially planar. The at least one surface can be part of (or comprise) an array of sensors, wherein each sensor of the array comprises at least one field confining feature and a plurality of immobilized capture probes. The plurality of immobilized capture probes of a given sensor of the array can be proximal to the field confining feature for the given sensor of the array. The plurality of immobilized capture probes of a given sensor of the array can be clonal. In some cases, a given sensor of the array comprises a plurality of immobilized capture probes that is unique relative to another sensor of the array.

The distance between a given sensor of the array and a nearest neighbor sensor can be any suitable distance. In some cases, the distance is at least about 5 nanometers (nm), at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 150 nm, at least about 200 nm, at least about 250 nm, at least about 500 nm, at least about 1000 nm, at least about 5000 nm or at least about 10000 nm. In some cases, the distance is at most about 50 nanometers (nm), at most about 100 nm, at most about 150 nm, at most about 200 nm, at most about 250 nm, at most about 500 nm, at most about 1000 nm, at most about 5000 nm or at most about 10000 nm.

The array can comprise any suitable number of sensors. In some cases, the array comprises at least about 5, at least about 10, at least about 50, at least about 100, at least about 500, at least about 1000, at least about 5000, at least about 10000, at least about 50000, at least about $10^6$, or at least about $10^7$ sensors.

In another aspect, the present disclosure provides a system for detecting a target analyte. The system comprises a sensor comprising a plurality of electrodes capable of applying an electric field to at least one surface that comprises a capture probe coupled thereto and in proximity to a sensing location; a solution chamber in fluid communication with the at least one surface, wherein the solution chamber is configured to retain a solution containing or suspected of containing the target analyte and a non-target analyte, under conditions sufficient to (i) permit the target analyte to couple to the at least one surface through a first non-covalent interaction, which first non-covalent interaction is with the capture probe, and (ii) the non-target analyte to couple to the at least one surface through a second non-covalent interaction; and a controller operatively coupled to the plurality of electrodes, wherein the controller is programmed to: (i) use a first set of electrodes of the plurality of electrodes to apply a first electric field that is sufficient to disrupt the second non-covalent interaction between the non-target analyte and the at least one surface, (ii) subsequent to applying the first electric field, use a second set of electrodes of the plurality of electrodes to apply a second electric field that is sufficient to disrupt the first non-covalent interaction between the target analyte and the capture probe, and (iii) detect a signal indicative of (1) a presence or absence of the target analyte, or (2) a disruption of the first non-covalent interaction. The target analyte may couple directly to the surface. In some cases, the target analyte couples indirectly to the surface (e.g., via a molecular linker). Examples of linkers include, but are not limited to, chemical compounds (e.g., polyethylene glycol), proteins (e.g., one of a protein-protein binding pair, e.g., biotin-avidin, or protein-binding partner pair), nucleic acids (e.g., a nucleic acid that is hybridizable to a capture probe comprising a nucleic acid or a nucleic acid of a nucleic acid-binding partner pair), or any combination of these.

In some cases, the sensor is part of an array of sensors. Each sensor of the array of sensors can be independently addressable. In some cases, each sensor of the array comprises at least one field confining feature. The capture probe of a given sensor can be proximal to the field confining feature for the given sensor of the array. The sensor can comprise a plurality of immobilized capture probes. The plurality of immobilized capture probes of a given sensor of the array can be proximal to the field confining feature for the given sensor of the array. The plurality of immobilized capture probes of a given sensor of the array can be clonal. In some cases, a given sensor of the array comprises a plurality of immobilized capture probes that is unique relative to another sensor of the array.

The distance between a given sensor of the array and a nearest neighbor sensor can be any suitable distance. In some cases, the distance is at least about 5 nanometers (nm), at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 150 nm, at least about 200 nm, at least about 250 nm, at least about 500 nm, at least about 1000 nm, at least about 5000 nm or at least about 10000 nm. In some cases, the distance is at most about 50 nanometers (nm), at most about 100 nm, at most about 150 nm, at most about 200 nm, at most about 250 nm, at most about 500 nm, at most about 1000 nm, at most about 5000 nm or at most about 10000 nm.

The system can comprise an array comprising any suitable number of sensors. In some cases, the array comprises at least about 5, at least about 10, at least about 50, at least about 100, at least about 500, at least about 1000, at least about 5000, at least about 10000, at least about 50000, at least about $10^6$, or at least about $10^7$ sensors.

The sensor can comprise a bias stabilization unit. A bias stabilization unit, in some cases, comprises a bias stabilization layer. As described elsewhere herein, a bias stabilization layer can be made from any electrically conductive material, such as a metal (e.g., silver, copper, gold, and platinum). Bias stabilization can minimize a voltage drop. Bias stabilization can provide a steady voltage over a period of at least about 0.01 seconds, 0.5 seconds, 1 seconds, 2 seconds, 3 seconds, 4 seconds, 5 seconds, 10 seconds, 30 seconds, 1 minute, 10 minutes, 30 minutes, or 1 hour. Bias stabilization can provide voltage stability with a deviation in voltage by at most about 10%, 5%, 4%, 3%, 2%, 1%, 0.5%, or 0.1% over an application period, such as over an application period of at least about 0.01 seconds, 0.5 seconds, 1 seconds, 2 seconds, 3 seconds, 4 seconds, 5 seconds, 10 seconds, 30 seconds, 1 minute, 10 minutes, 30 minutes, or 1 hour.

The sensor can further comprise a sensing unit operatively coupled to the controller, wherein the controller detects the signal using the sensing unit. In some cases, the sensing unit is an optical sensing unit, and the signal indicative of the presence of the target analyte is an optical signal. The bias stabilization layer, in some cases, is optically opaque and does not occlude the sensing locations.

In some cases, the first set of electrodes is the second set of electrodes. In some cases, the first set of electrodes is not the second set of electrodes.

In another aspect, the present disclosure provides method for detecting a presence of a target analyte, comprising (a) activating at least one sensor comprising one or more surfaces between two or more electrodes, wherein the one or more surfaces comprise two or more immobilized capture probes; (b) bringing the one or more surfaces in contact with a solution containing or suspected of containing a target analyte and a non-target analyte, under conditions that are sufficient to permit the target analyte and non-target analyte to each bind to a given one of the two or more immobilized capture probes; (c) applying a voltage across the two or more electrodes that is sufficient to release the non-target analyte, but not the target analyte, from a given one of the two or more immobilized capture probes; and (d) detecting a presence of the target analyte on the one or more surfaces. The target analyte and/or the non-target analyte can be a charged analyte. The voltage can be sufficient to exert an applied force of at least about 1 piconewton (pN) on the non-target analyte. Operations (c) and/or (d) can be performed in the absence of washing the one or more surfaces. In some cases, the target analyte couples indirectly to the surface (e.g., via a molecular linker). Examples of linkers include, but are not limited to, chemical compounds (e.g., polyethylene glycol), proteins (e.g., one of a protein-protein binding pair, e.g., biotin-avidin, or protein-binding partner pair), nucleic acids (e.g., a nucleic acid that is hybridizable to a capture probe comprising a nucleic acid or a nucleic acid of a nucleic acid-binding partner pair), or any combination of these.

The method of can further comprise applying an additional voltage across the two or more electrodes that is sufficient to release the target analyte from a given one of the two or more immobilized capture probes. The additional voltage can be sufficient to exert an applied force of at least about 1 piconewton (pN) on the target analyte.

The force applied on the target or non-target analytes can be at least about 1 piconewton (pN), at least about 5 pN, at least about 10 pN, at least about 20 pN, at least about 50 pN, at least about 100 pN, at least about 500 pN, at least about 1000 pN or at least about 5000 pN. In some instances, the applied force is at most about 1 piconewton (pN), at most about 5 pN, at most about 10 pN, at most about 20 pN, at most about 50 pN, at most about 100 pN, at most about 500 pN, at most about 1000 pN or at most about 5000 pN on the analyte.

The method can further comprise detecting the presence of the target analyte on the one or more surfaces subsequent to application of the additional voltage. The voltage can be less than the additional voltage.

The voltage and the additional voltage can be individual voltages of a continuously applied voltage that is changed over time, as shown in FIG. 6A or FIG. 8A.

The voltage and/or the additional voltage can be applied in the absence of washing the one or more surfaces. For example, the methods of the present disclosure can be performed in complex mixtures such as biological fluids (e.g., blood) or environmental samples.

The applied voltage can be sufficient to generate an electric field having a strength of less than about $10^9$ volts per meter (V/m) and the additional applied voltage can be sufficient to generate an additional electric field having a strength of less than about $10^9$ V/m, less than about $10^8$ m, less than about $10^7$ V/m, less than about $10^6$ V/m, less than about $10^5$ V/m, less than about $10^4$ V/m, less than about $10^3$ V/m, or lower.

In some cases, each of the target analyte and non-target analyte non-covalently binds to a given one of the two or more immobilized capture probes to form a target probe-analyte complex immobilized and a non-target probe-analyte complex immobilized on the one or more surfaces, respectively.

The applied voltage can be increased from a first voltage to a second voltage overtime. The applied voltage can be increased from the first voltage to the second voltage at a rate of at least about 1 millivolt per second (mV/s), at least about 5 mV/s, at least about 10 mV/s, at least about 50 mV/s, at least about 100 mV/s, at least about 500 mV/s, at least about 1000 mV/s, at least about 5000 mV/s, or more.

In some cases, the applied voltage is increased from the voltage to the additional voltage over a period of time greater than about 10 microseconds, greater than about 50 microseconds, greater than about 100 microseconds, greater than about 500 microseconds, greater than about 1000 microseconds, greater than about 5000 microseconds, greater than about 10000 microseconds or more. In some cases, the applied voltage is increased from the voltage to the additional voltage over a period of time less than about 1 second.

The applied voltage can be a periodic voltage waveform. The periodic voltage waveform can have any suitable frequency, such as a frequency of less than about $10^9$ Hertz (Hz), less than about $10^8$ Hz, less than about $10^7$ Hz, less than about $10^6$ Hz, less than about $10^5$ Hz, less than about $10^4$ Hz, less than about $10^3$ Hz, less than about $10^2$ Hz, less than about 10 Hz, less than about 1 Hz, less than about $10^{-2}$ Hz, or less than about $10^{-3}$ Hz. The periodic voltage waveform can have a frequency of greater than about $10^9$ Hertz (Hz), greater than about $10^8$ Hz, greater than about $10^7$ Hz, greater than about $10^6$ Hz, greater than about $10^5$ Hz, greater than about $10^4$ Hz, greater than about $10^3$ Hz, greater than about $10^2$ Hz, greater than about 10 Hz, greater than about 1 Hz, greater than about $10^{-2}$ Hz, or greater than about $10^{-3}$ Hz.

The method of can further comprise monitoring a signal indicative of the presence of the target analyte on the one or more surfaces as the applied voltage is varied over time.

The method can further comprise determining a binding force of the target analyte bound to a given one of the two or more immobilized capture probes (e.g., the force required to dissociate the analyte from the binding probe).

The applied force can be less than a binding force of the target analyte bound to a given one of the two or more immobilized capture probes.

The electrolyte (solution) can comprise charged molecules that bind with the target analyte and/or the non-target analyte, to provide a change in charge on the target analyte and/or non-target analyte. The charged molecules can be antibodies.

The presence of the target analyte on the one or more surfaces can be detected by measuring a signal associated with the target analyte. The signal can be a charge signal. The charge signal can be detected using a sensing electrode and a reference electrode. The charge signal can be a voltage.

The presence of the target analyte on the one or more surfaces can be detected by measuring an optical signal associated with the target analyte. The optical signal can be a fluorescence signal. The fluorescence signal can be provided by a fluorescent probe covalently or non-covalently attached to the target analyte.

The presence of the target analyte on the one or more surfaces can be detected using surface plasmon resonance.

The one or more surfaces can comprise a membrane having a thickness of between about 0.08 nanometers and 1 millimeter. The one or more surfaces can include a plurality of surfaces. Each of the plurality of surfaces can comprise a subset of the two or more immobilized capture probes.

The voltage can be a direct current voltage or an alternating current voltage.

In another aspect, the present disclosure provides a method for detecting a target analyte. The method comprises (a) providing a sensor comprising a plurality of electrodes capable of applying an electric field to at least one surface that comprises a capture probe coupled thereto and in proximity to a sensing location; (b) contacting the at least one surface with a solution containing or suspected of containing a target analyte and a non-target analyte, under conditions sufficient to (i) permit the target analyte to couple to the at least one surface through a first non-covalent interaction, which first non-covalent interaction is with the capture probe, and (ii) permit the non-target analyte to couple to the at least one surface through a second non-covalent interaction; (c) using a first set of electrodes of the plurality of electrodes to apply a first electric field that is sufficient to disrupt the second non-covalent interaction between the non-target analyte and the at least one surface; (d) subsequent to (c), using a second set of electrodes of the plurality of electrodes to apply a second electric field that is sufficient to disrupt the first non-covalent interaction between the target analyte and the capture probe; and (e) detecting a signal indicative of (1) a presence or absence of the target analyte, or (2) a disruption of the first non-covalent interaction. In some cases, the target analyte couples indirectly to the surface (e.g., via a molecular linker). Examples of linkers include, but are not limited to, chemical compounds (e.g., polyethylene glycol), proteins (e.g., one of a protein-protein binding pair, e.g., biotin-avidin, or protein-binding partner pair), nucleic acids (e.g., a nucleic acid that is hybridizable to a capture probe comprising a nucleic acid or a nucleic acid of a nucleic acid-binding partner pair), or any combination of these.

In some cases, the non-target analyte is charged, and the first electric field provides a force on the non-target analyte that is sufficient to disrupt the second non-covalent interaction. In some cases, the target analyte is charged, and applying the second electric field provides a force on the target analyte sufficient to disrupt the first non-covalent interaction. In some cases, the method further comprises applying a third electric field that is sufficient to dissociate the capture probe from the at least one surface. In some cases, the first electric field has a strength of less than about $10^9$ volts per meter (V/m), $10^8$ V/m, $10^7$ V/m, $10^6$ V/m, $10^5$ V/m, $10^4$ V/m, $10^1$ V/m, $10^2$ V/m, 10 V/m, or less. In some cases, the second electric field has a strength of less than about $10^9$ volts per meter (V/m), $10^8$ V/m, $10^7$ V/m, $10^6$ V/m, $10^5$ V/m, $10^4$ V/m, $10^3$ V/m, $10^2$ V/m, 10 V/m, or less. The third electric field, when applied, can have a strength of less than about $10^9$ volts per meter (V/m), $10^8$ V/m, $10^7$ V/m, $10^6$ V/m, $10^5$ V/m, $10^4$ V/m, $10^3$ V/m, $10^2$ V/m, 10 V/m, or less.

The force provided by any one of the first electric field, the second electric field, and the third electric field on the target analyte, non-target analyte, and/or capture probe can be of any suitable magnitude. For example, the force provided can be at least about 1 piconewton (pN), at least about 5 pN, at least about 10 pN, at least about 20 pN, at least about 50 pN, at least about 100 pN, at least about 500 pN, at least about 1000 pN or at least about 5000 pN. In some instances, the applied force is at most about 1 piconewton (pN), at most about 5 pN, at most about 10 pN, at most about 20 pN, at most about 50 pN, at most about 100 pN, at most about 500 pN, at most about 1000 pN or at most about 5000 pN. In some cases, the first electric field and/or the second electric field is applied without washing the at least one surface.

The first electric field and the second electric field can be applied by establishing a first voltage and a second voltage across the first set of electrodes and the second set of electrodes, respectively. In some cases, the second voltage is greater than the first voltage. In some cases, the second voltage is not greater than the first voltage. In some cases, the first voltage and the second voltage are individual voltages of a continuously applied voltage changed over time (e.g., increasing from a lower first voltage to a higher second voltage or decreasing from a higher first voltage to a lower second voltage). The first voltage can be increased to the second voltage at a rate of at least about 1 millivolt per second, at least about 5 mV/s, at least about 10 mV/s, at least about 50 mV/s, at least about 100 mV/s, at least about 500 mV/s, at least about 1000 mV/s, at least about 5000 mV/s, or more. The first voltage can be increased to the second voltage at a rate of at least about 1 millivolt over a period of time of less than about 1 second. The first voltage can be decreased to the second voltage at a rate of at least about 1 millivolt per second, at least about 5 mV/s, at least about 10 mV/s, at least about 50 mV/s, at least about 100 mV/s, at least about 500 mV/s, at least about 1000 mV/s, at least about 5000 mV/s, or more. The first voltage can be decreased to the second voltage at a rate of at least about 1 millivolt over a period of time of less than about 1 second.

In some cases, the method further comprises detecting an additional signal indicative of (1) a presence or absence of the non-target analyte, or (2) a disruption of the second non-covalent interaction between the non-target analyte and the at least one surface. In some cases, in (b), the second non-covalent interaction is with another capture probe coupled to the at least one surface.

The signal can be detected in real time or substantially in real time. The signal may be detected during the disruption and/or over a time period of less than or equal to about 1 minute, 30 seconds, 10 seconds, 5 seconds, 1 second, or 0.5 seconds after disruption. For example, the signal is detected as the second non-covalent interaction between the non-target analyte and the at least one surface is disrupted or substantially in real time (e.g., within about femtoseconds, picoseconds, nanoseconds, microseconds, milliseconds, centiseconds, deciseconds, seconds, or within about minutes of the disruption). The additional signal can be detected before applying the second electric field.

The target analyte can be detected using a detectable tag. Detectable tags can be detected in various ways. For example, a detectable tag may be detected optically, such as by fluorescent or chemical staining, electronically, electrically, electromagnetically, plasmonically, or any combination thereof. In some cases, a detectable tag comprises a fluorophore. Detectable tags comprising fluorophores can be detected by subjecting the tag to visible or infrared light at an excitation wavelength. The detectable tag can absorb and reemit the light energy, for example at a greater wavelength, and the reemitted light can be detected as distinct from the excitation light energy. Non-fluorescent detectable tags can also be used. Non-fluorescent detectable tags, in some cases, may rely upon a mechanism other that reemission of excitation energy in order to be detected. Detectable tags, in some cases, can comprise a radiolabel that emits at least one alpha or beta particle for detection. In some cases, a detectable tag comprises a chemical moiety having distinct charge or conductance properties, such that when passed through a current such as an electromagnetic current, the current is predictably altered in a manner such that the presence of the label may be detected. In some cases, the detectable tag is coupled to a detectable antibody that binds to the target analyte.

In some cases, the first electric field is not sufficient to release the target analyte. The first electric field and/or second electric field can be stabilized using a bias stabilization unit. A bias stabilization unit, in some cases, comprises a bias stabilization layer. As described elsewhere herein, a bias stabilization layer can be made from any electrically conductive material, such as a metal (e.g., silver, copper, gold, and platinum). Bias stabilization units can be useful for minimizing voltage drops.

The signal can be indicative of a binding energy associated with the non-covalent interaction between the target analyte and the capture probe. In some cases, the capture probe is a nucleic acid molecule.

The signal can be detected with a sensing unit operatively coupled to the sensing location. In some cases, the sensing unit is an optical sensing unit, and the signal is an optical signal. For example, the signal can be a fluorescence signal. An optical detection system can include a light source, an excitation filter, a dichroic mirror and an emission filter. When using an optical sensing unit to detect an optical signal, the at least one surface of the sensor may comprise optically transparent material. In some cases, the sensing unit senses an electronic signal, an electric signal, an electromagnetic signal, a plasmonic signal, or any combination thereof. The signal can be detected in real time or substantially in real time. The signal may be detected during the disruption and/or over a time period of less than or equal to about 1 minute, 30 seconds, 10 seconds, 5 seconds, 1 second, or 0.5 seconds after disruption. For example, the signal is detected as the first non-covalent interaction between the target analyte and the capture probe is disrupted or substantially in real time (e.g., within about femtoseconds, picoseconds, nanoseconds, microseconds, milliseconds, centiseconds, deciseconds, seconds, or within about minutes of the disruption).

The first set of electrodes or the second set of electrodes can comprise two or more electrodes (e.g., three, four, five, six, seven, eight, nine, ten or more electrodes). In some cases, the first set of electrodes is the second set of electrodes.

In another aspect, the present disclosure provides a system for detecting a presence of a target analyte, comprising: (a) at least one sensor comprising one or more surfaces between two or more electrodes, wherein the one or more surfaces comprise two or more immobilized capture probes; (b) a solution chamber in fluid communication with the one or more surfaces, wherein the solution chamber is configured to retain a solution containing or suspected of containing the target analyte and a non-target analyte, under conditions that are sufficient to permit the target analyte and non-target analyte to each bind to a given one of the two or more immobilized capture probes; and (c) a controller that is operably coupled to the two or more electrodes, wherein the controller is programmed to (i) apply a voltage across the two or more electrodes that is sufficient to release the non-target analyte, but not the target analyte, from a given one of the two or more immobilized capture probes, and (ii) detect a presence of the target analyte on the one or more surfaces.

The target analyte and/or the non-target analyte can be a charged analyte. In some cases, the target analyte and/or the non-target analyte can have a first charge (e.g., zero charge) and may obtain a second charge (e.g., +2, −2) upon coupling to a charged molecule.

The voltage across the two or more electrodes can be sufficient to exert an applied force of at least 1 piconewton on the non-target analyte. The at least one sensor can comprise an array of sensors. Each sensor of the array of sensors can be independently addressable (e.g., have measurements taken from it).

EXAMPLES

Various aspects of the present disclosure are further illustrated by the following non-limiting examples.

Example 1: Apparatus and Sensor Array

Figure 19:
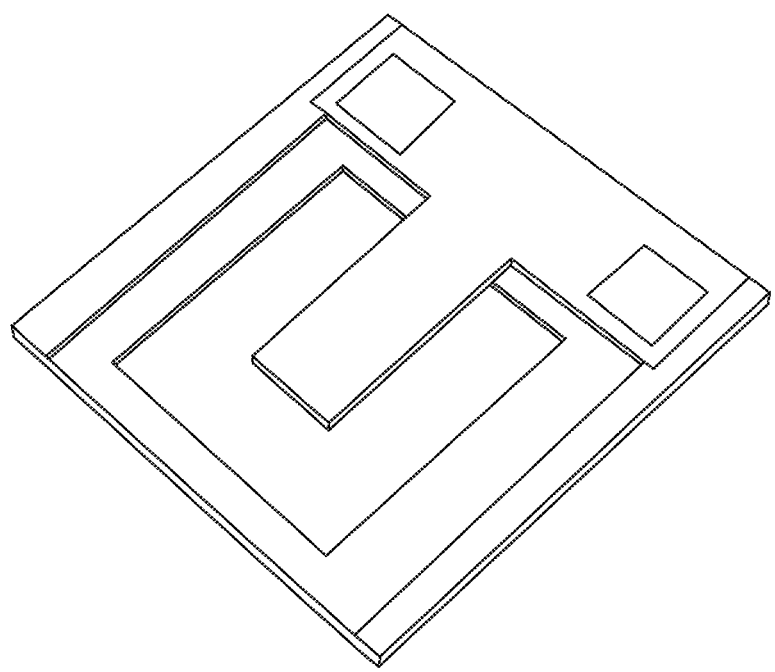
FIG. 19 shows a photograph of an example of a chip of the present disclosure.

The sensor array is constructed on a quartz substrate. A layer of transparent material acts as the electrode and the surface for capture molecule attachment is deposited (e.g. 7-10 ohm Indium Tin Oxide). Subsequently, 500 micrometers of insulating layer is deposited by low pressure chemical vapor deposition of silicon dioxide. The opaque and conducting optical and electrical isolating surface is deposited by sputter deposition of 10 nanometers (nm) of Titanium and 50 nm of Platinum. The stack of insulating layer and opaque metal are patterned via photolithography and ion etching to expose the underlying transparent electrode. The chip used for this example is shown schematically in FIG. 1A. A photograph of the chip is shown in FIG. 19.

Example 2: SNP Detection

The chip surface is cleaned for 10 min with $O_2$ plasma and a gas phased deposition of amino silane is completed. PMPI (p-maleimidophenyl isocyanate) molecules are attached to the amine group on the chip in an anhydrous toluene environment at 40° C. for 2 hrs, enabling subsequent oligo attachment. The following two single nucleotide polymorphism (SNP) capture probes are used, TCA TCT CCT AGT AGA TAA AA/3ThioMC3-D/(SEQ ID NO: 1) and TCA TCT CGT AGT AGA TAA AA/3ThioMC3-D/(SEQ ID NO: 2). The thiol group in the SNP capture probes are reduced by 1 mM TCEP (tris(2-carboxyethyl)phosphine) overnight at 4° C. The reduced probes are spotted on the appropriate area of the chip by a Scienion spotter.

The following detecting molecule with fluorescent TAMRA (tetramethylrhodamine) modification is purchased ATC TAC TAG GAG ATG AAT AGA CTA CCA ACA GGA GCA CCG GAA CCC ATG TAT GAC TCC CAG TAA GTT AAA GTT AGG TCA GTC GTG TAA CCG TAG TAT AGA/36-TAMSp/(SEQ ID NO: 3). The detecting molecule hybridizes without mismatch to the first probe (SEQ ID NO: 1) and has a single base mismatch to the second capture probe (SEQ ID NO: 2). The detecting molecule is introduced to the chip by hand spotting a 100 nM concentration of the molecule in 20× saline-sodium citrate (SSC) buffer overnight in a heated (80° C.) and humid environment. The target hybridized chip is then immersed in a mild acidic buffer 10 mM HEPES pH 6.7. A sinusoidal excitation of a suitable amplitude is applied to the bulk electrode (100 kHz for 30 seconds) and subsequently imaged to observe the detecting molecule's response to external force.

Figure 20:
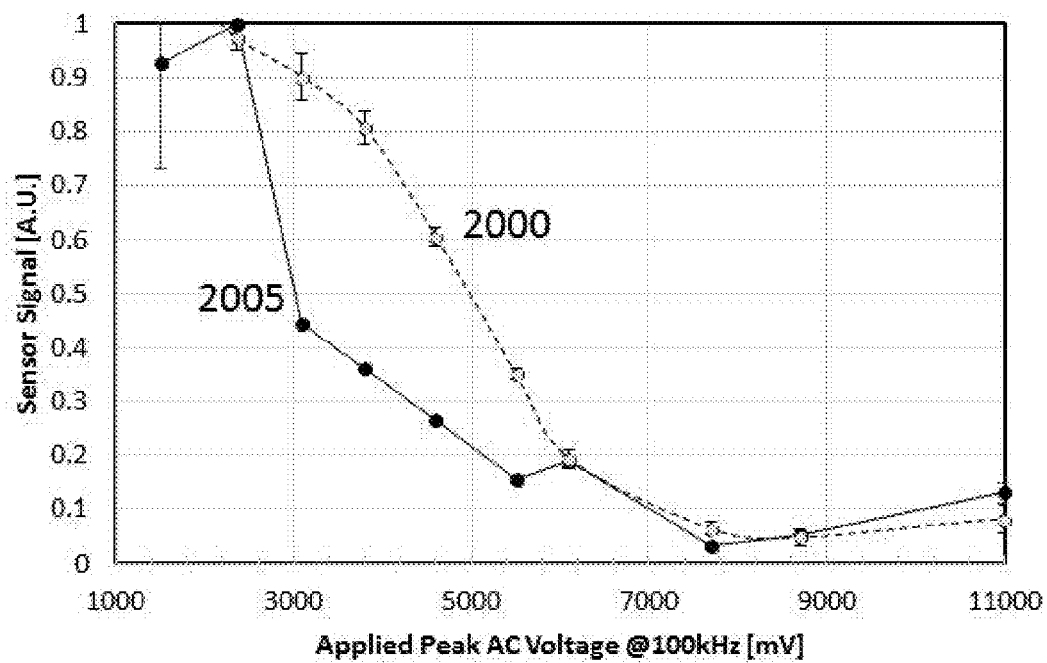
FIG. 20 shows an example of a sensor signal output versus applied voltage for a single nucleotide polymorphism (SNP) detection assay of the present disclosure.

The results of the SNP detection assay are shown in FIG. 20. The vertical axis is in arbitrary units (A.U.) of sensor signal ranging from 0 to 1. The horizontal axis is the applied peak AC voltage in units of millivolts (mV) ranging from 1,000 to 11,000. The AC voltage is applied at a frequency of 100 kHZ. The force spectroscopy assay performed here can distinguish amongst 15mer oligonucleotides having a single base difference (i.e., a SNP). The sensor signal decreases at a higher applied voltage for the perfectly matched oligonucleotide 2000 compared with the mis-matched oligonucleotide 2005.

Example 3: Cytokine Assay

The sensor chip is prepared with both anti-IL6 and anti-IL8 capture antibodies. A commercially available IL8 antibody pair is purchased from Thermo Fisher Scientific (Catalog No. CHC1303). The capture antibody is modified with the following oligo/5ThioMC6-D/TCA CGG TAG CAT AAG GTG CAC GTT ACC TTG ATT CCC GTC C/3AmMO/(SEQ ID NO: 4). The oligo and the capture antibody are conjugated using an Antibody-Oligonucleotide All-in-One Conjugation Kit, available from Solulink (Catalog No. A-9202-001). The conjugated antibody oligo complex has the thiol group reduced in mild TCEP overnight at 4° C. The reduced conjugate are spotted onto the appropriate area of the sensor chip by a Scienion spotter. Anti-IL6 capture antibodies are similarly immobilized onto the sensor chip.

The entire chip, which has both immobilized anti-IL6 and anti-IL8 capture antibody, is exposed to an equal mix of IL6 and IL8 antigen for 1 hour. The chip is subsequently washed with deionized (DI) water to remove excess antigens. Biotinylated anti-IL6 detecting antibody is diluted to 10 pg/mL concentration in PBS and incubated over the chip sensor area for 1 hour at room temperature. The chips are subsequently washed with DI water to remove excess detecting antibodies. 1 nM concentration of streptavidin in phosphate buffered saline (PBS) is hand spotted on to the chip surface to bind to the biotinylated detecting antibodies for 15 min. The chips are subsequently washed with DI water to remove excess streptavidin. 100 nM biotinylated oligo with Alexa 647 fluorophore conjugated are spotted onto the chip and incubated for 30 min. A sinusoidal excitation of a suitable amplitude is applied to the bulk electrode (100 kHz for 30 seconds) and subsequently imaged to observe the detecting molecule's response to external force.

Figure 21:
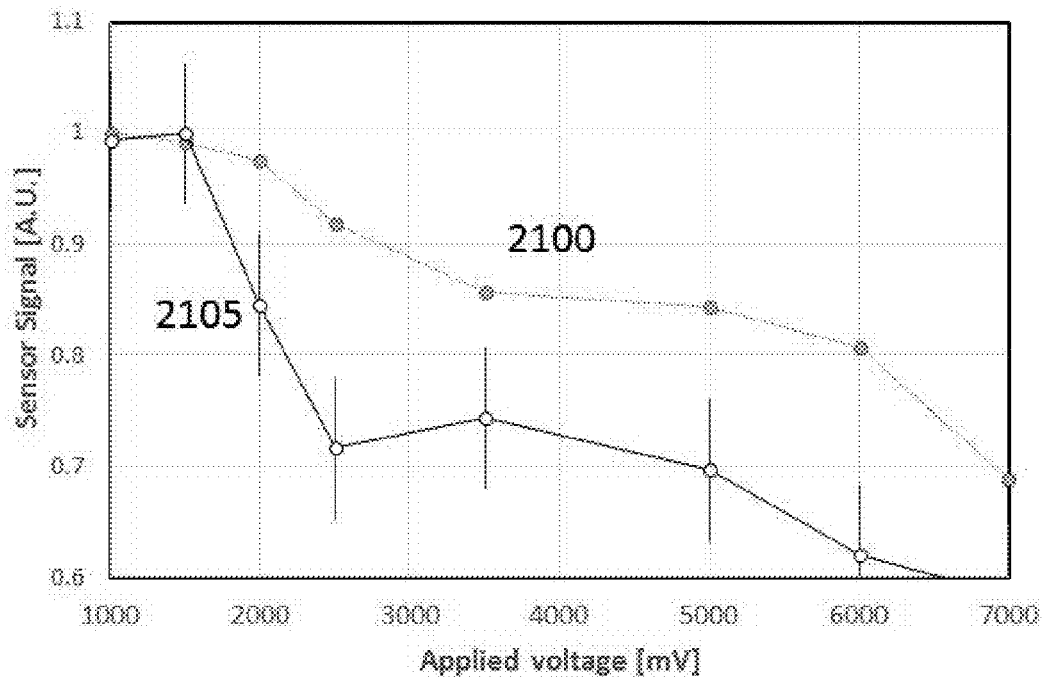
FIG. 21 shows an example of a sensor signal output versus applied voltage for a single cytokine detection assay of the present disclosure.

The results of the cytokine detection assay are shown in FIG. 21. The vertical axis is in arbitrary units (A.U.) of sensor signal ranging from 0.6 to 1.1. The horizontal axis is the applied voltage in units of millivolts (mV) ranging from 1,000 to 7,000. The force spectroscopy assay performed can distinguish amongst specifically and non-specifically bound antigens. The sensor signal decreases at a higher applied voltage for the perfectly matched antigen 2100 (IL6 cytokine bound to an anti-IL6 antibody) compared with the mis-matched antigen 2105 (IL8 cytokine bound to an anti-IL6 antibody).

Example 4: Sandwich Assay

Figure 22:
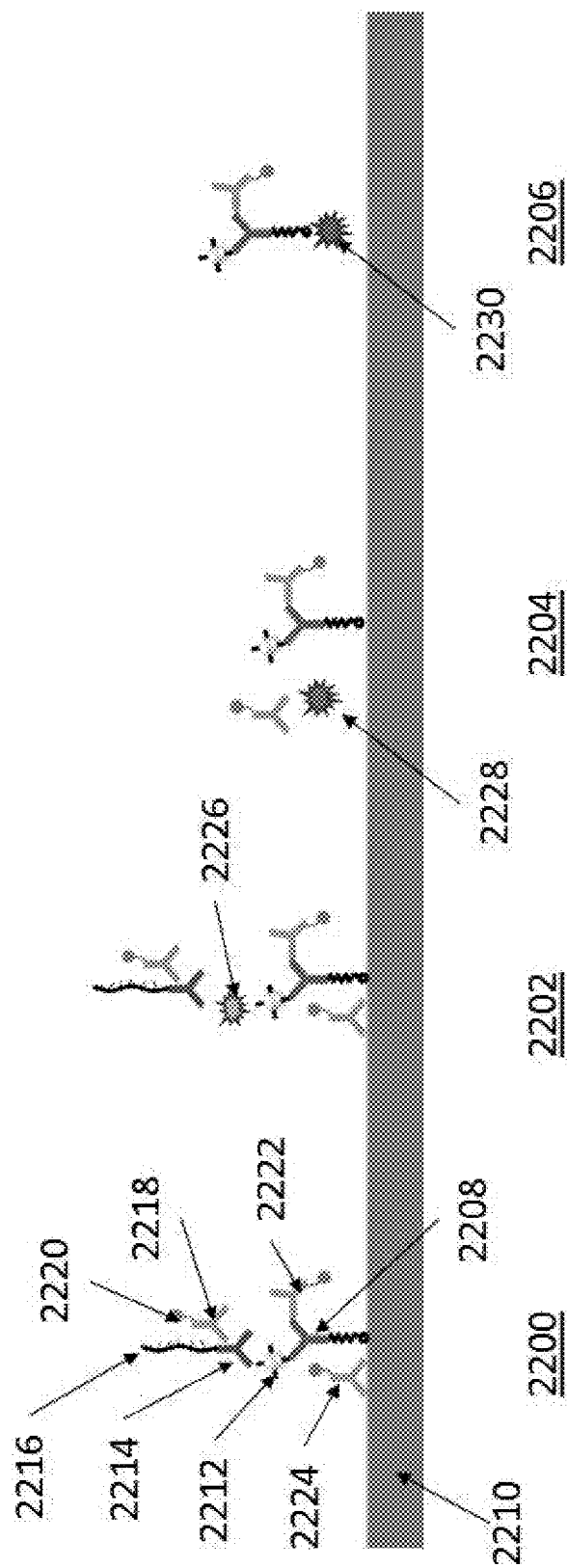
FIG. 22 shows an example of a sandwich assay performed according to the methods of the present disclosure.

FIG. 22 shows an example of a sandwich assay. FIG. 22 illustrates four exemplary states of the system as the applied force increases from an initial state (e.g., no applied voltage) 2200 to a second state 2202, a third state 2204 and a fourth state 2206 (e.g., having the highest applied voltage). Intermediate states can exist. Additional states can exist. Not all of the depicted states may exist. A capture antibody 2208 can be tethered to a substrate 2210 (e.g., by a linker). The antigen 2212 can bind to the capture antibody. A secondary antibody 2214 can also bind to the antigen. The secondary antibody can have a charged tag 2216 which can be used to exert a force on the secondary antibody in an applied electric field. The system can also include a detection antibody 2218 which has a detectable tag 2220 such as a fluorophore. The detection antibody can bind specifically to the capture antibody (as shown). In some cases, the system does not have a detection antibody and the secondary antibody is detectable (e.g., by a fluorophore attached to the secondary antibody). In addition to the specific binding of the detection antibody (at 2218), the detection antibody can bind non-specifically, such as to the capture antibody 2222 or to the substrate 2224. An initial signal can be detected that has components attributable to the specifically bound 2218 and the non-specifically bound 2222 and 2224 detection antibodies.

Increasing the applied voltage to a second state 2202 can create an applied force on the secondary antibody that can disrupt 2226 the bond between the secondary antibody and the antigen. This bond is disrupted first because the charge tag can assist in creating a large applied force at a low applied voltage. The detection antibody associated with the secondary antibody (specifically bound 2218) can diffuse away, which can decrease the detected signal.

Increasing the applied voltage to a third state 2204 can create an applied force on the detection antibody that can disrupt 2228 the bond between the detection antibody and the substrate. The detection antibody can diffuse away, which can further decrease the detected signal.

Increasing the applied voltage to a fourth state 2206 can create an applied force on the detection antibody that can disrupt 2230 the bond between the capture antibody and the substrate. The capture antibody (along with the bound detection antibody) can diffuse away, which can further decrease the detected signal (e.g., to no detectable signal).

Figure 23:
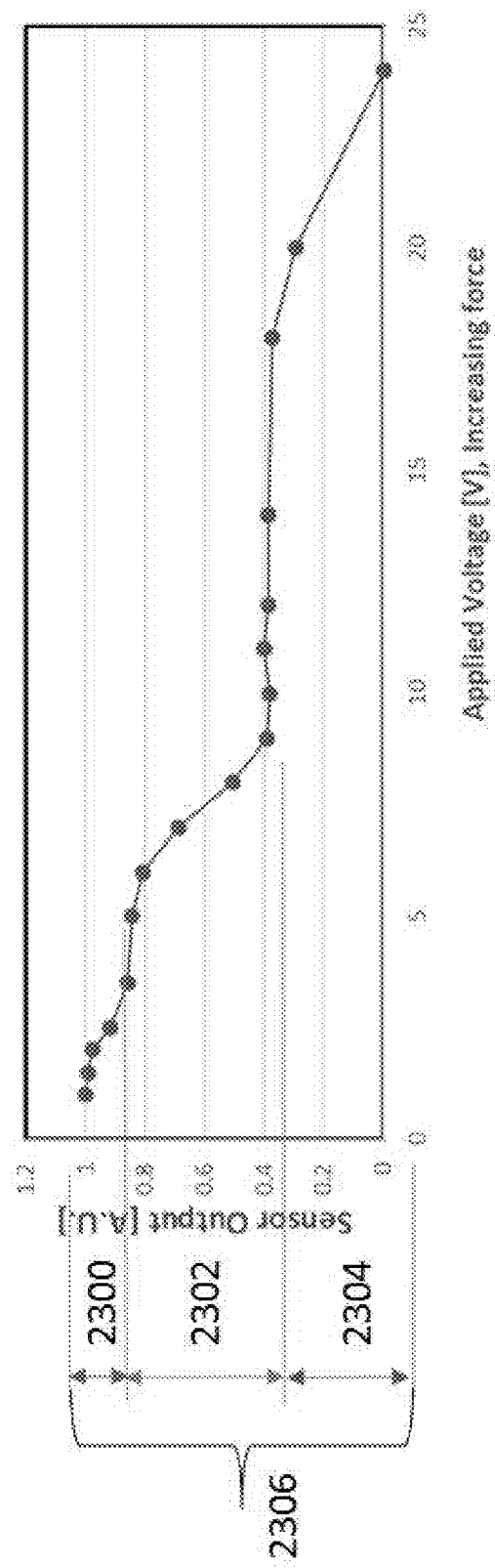
FIG. 23 shows an example of a sensor signal output versus applied voltage for a sandwich assay of the present disclosure.

The results of the sandwich assay described herein are shown in FIG. 23. The vertical axis is in arbitrary units (A.U.) of sensor signal ranging from 0 to 1.2. The horizontal axis is the applied voltage in units of volts (V) ranging from 0 to 25. The force spectroscopy assay performed here can distinguish amongst specifically and non-specifically bound detection antibody. The sensor signal decreases as the applied voltage increases according to a pattern that can be associated with the states of the system shown in FIG. 22. The first decrease in signal 2300 can correspond with detachment of the secondary antibody from the antigen (2202 in FIG. 22). The second decrease in signal 2302 can correspond with detachment of the detection antibody from the substrate (2204 in FIG. 22). The third decrease in signal 2304 can correspond with detachment of the capture antibody from the substrate (2206 in FIG. 22). The sandwich assay described herein can provide more detailed information than a traditional sandwich assay, which has as its endpoints the complete change in signal 2306 rather than the components of the signal (2300, 2302 and 2304).

Example 5: Sandwich Assay

Figure 24A:
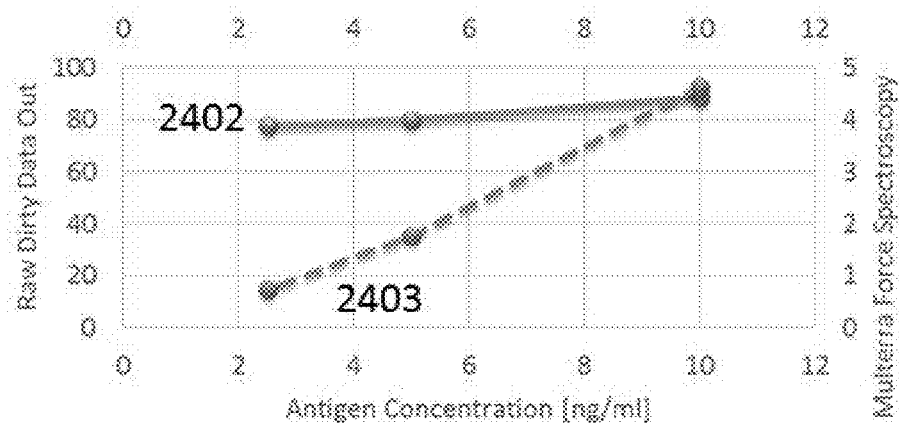
FIGS. 24A-24C show an example of a sandwich assay of the present disclosure.
Figure 24B:
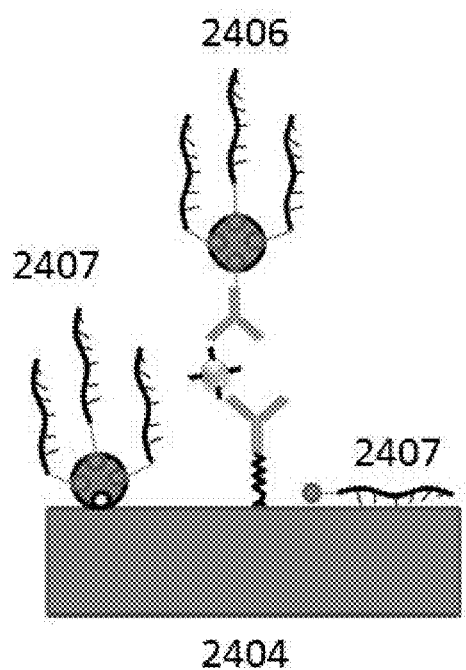
Figure 24C:
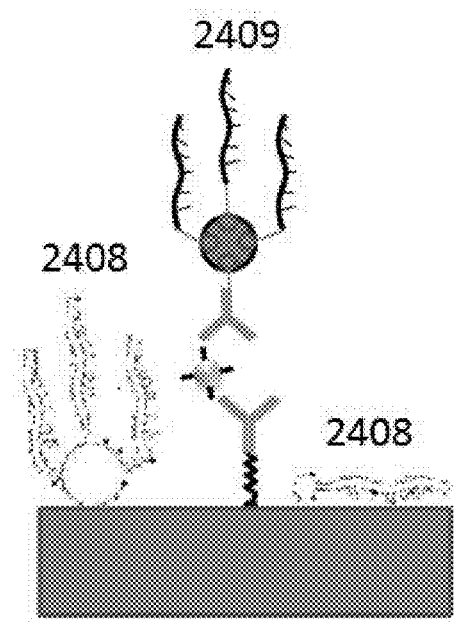

FIGS. 24A-C depict a sandwich assay of the present disclosure. In FIG. 24A, graph 2401 shows a comparison between the signal without force spectroscopy 2402 and the signal derived using the force spectroscopy methods described herein 2403. The illustration of FIG. 24B shows a state of the system without force spectroscopy 2404, and the illustration of FIG. 24C shows a state of the system with force spectroscopy 2405. As shown, without force spectroscopy, the signal gets contributions from reporting molecules that are bound to the antigen 2406 and to the surface 2407. Because of this convolution of signal and background, the signal 2402 is less sensitive to the antigen concentration. In contrast, the force spectroscopy methods described herein remove the reporting molecules that are weakly associated with the surface 2408, leaving only those bound to the antigen 2409, thereby making the signal 2403 sensitive to antigen concentration.

Example 6: Detection Assay Using a Nanopore Apparatus

The systems and methods described herein may not require a pore having a nanometer scale opening (i.e., nanopore) or passage of ions through the pore, which may become blocked. However, in some cases, nanopore devices may be used with methods and systems of the present disclosure. Such nanopore devices may be, for example as described in U.S. Pat. No. 8,324,914, PCT Patent Publication WO2013/191793A1, PCT Patent Publication WO2008/102120A1, PCT Patent Publication WO2010/004273A1, or PCT Patent Publication WO2015/110777A1, each of which is incorporated herein by reference in its entirety.

Figure 25A:
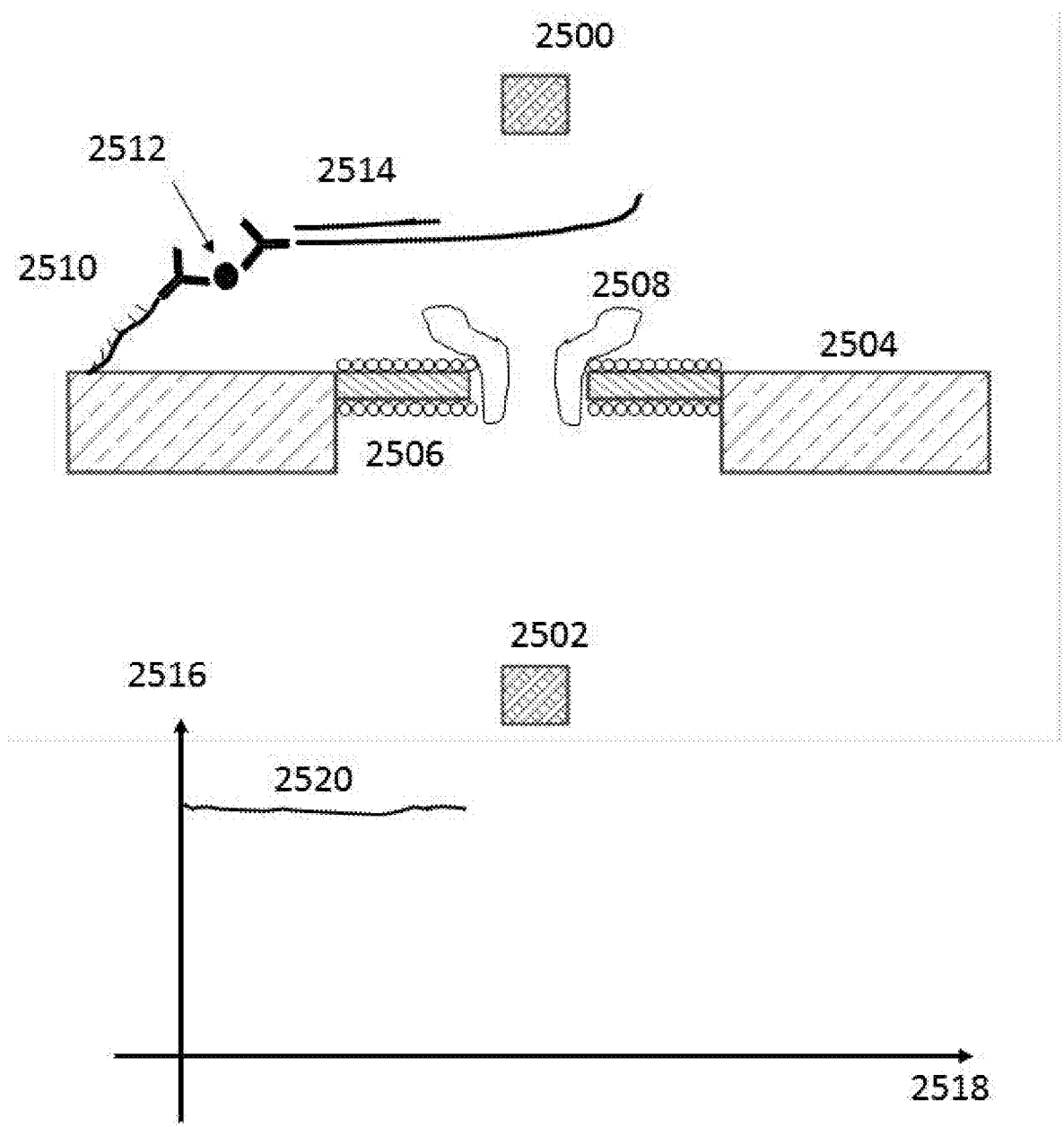
FIGS. 25A-25D show an example of a sandwich assay of the present disclosure performed using a nanopore.

With reference to FIG. 25A, the systems and methods can be performed with a nanopore such as the phi29 motor protein pore which has an approximately 3.5 nanometer (nm) diameter opening. This opening is large enough to pass a double stranded nucleic acid through it, but not typically large enough to pass a protein. In some embodiments, the pore is alpha hemolysin. The system comprises a first electrode 2500 and a second electrode 2502 capable of providing an electromotive force across a substrate 2504. The substrate can have an opening that can be partially spanned by a lipid bilayer 2506 having a nanopore 2508 therein. A capture probe 2510 such as an antibody can be attached to the substrate in proximity to the pore. The capture probe can bind to an analyte of interest 2512 such as an antigen, which in turn can bind a detection probe 2514 in order to perform a sandwich assay as described herein.

Figure 25B:
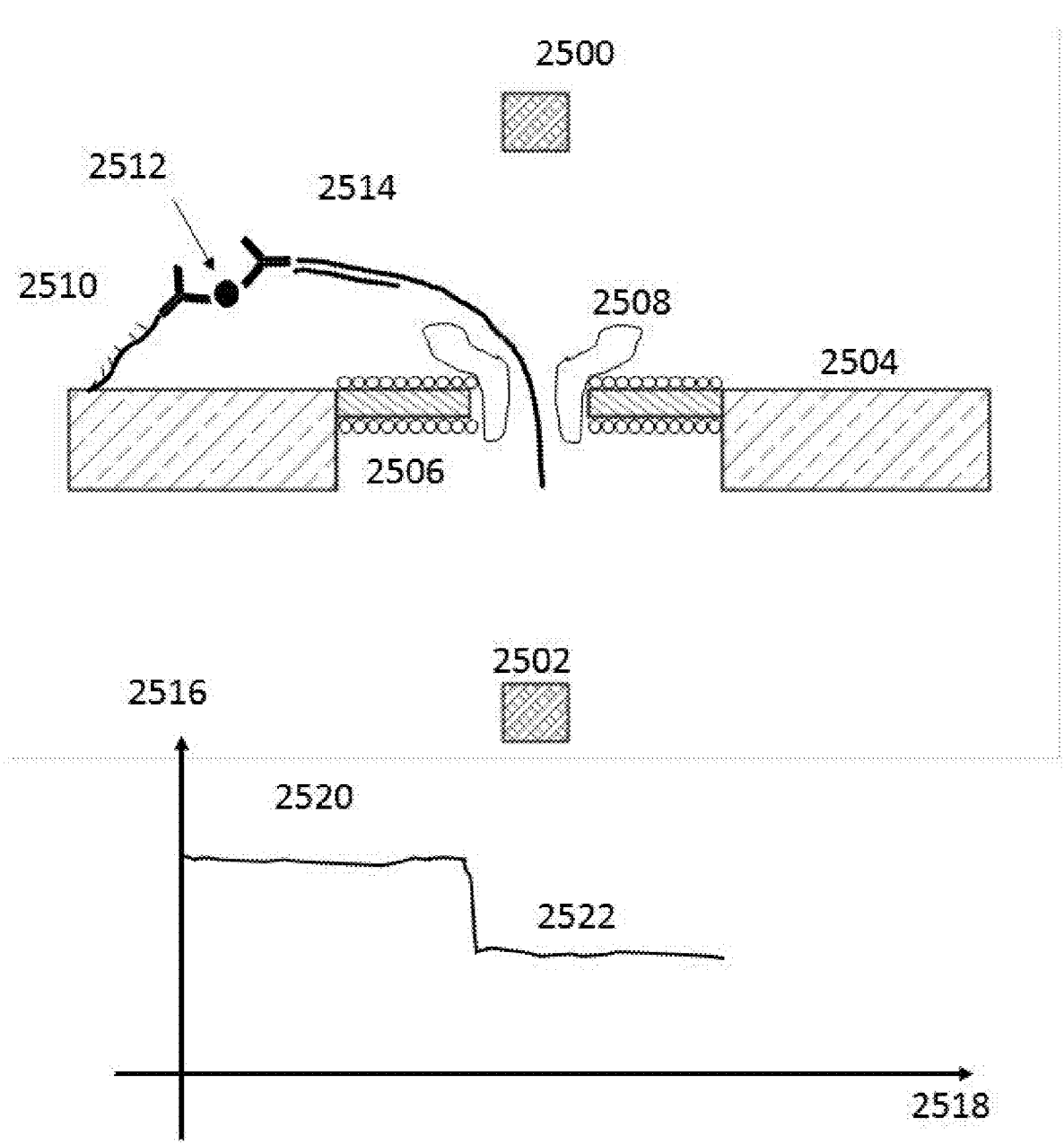
Figure 25C:
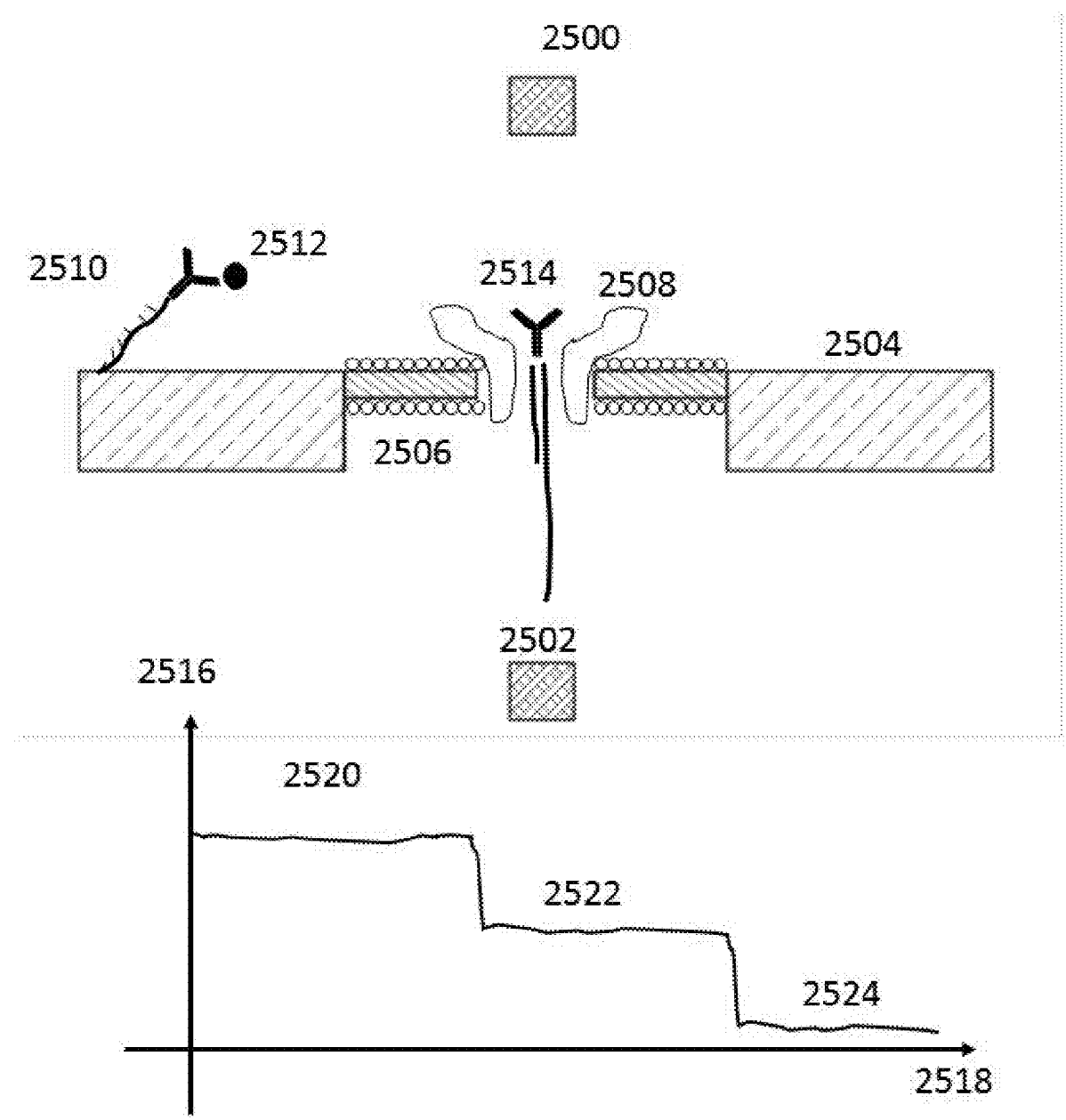
Figure 25D:
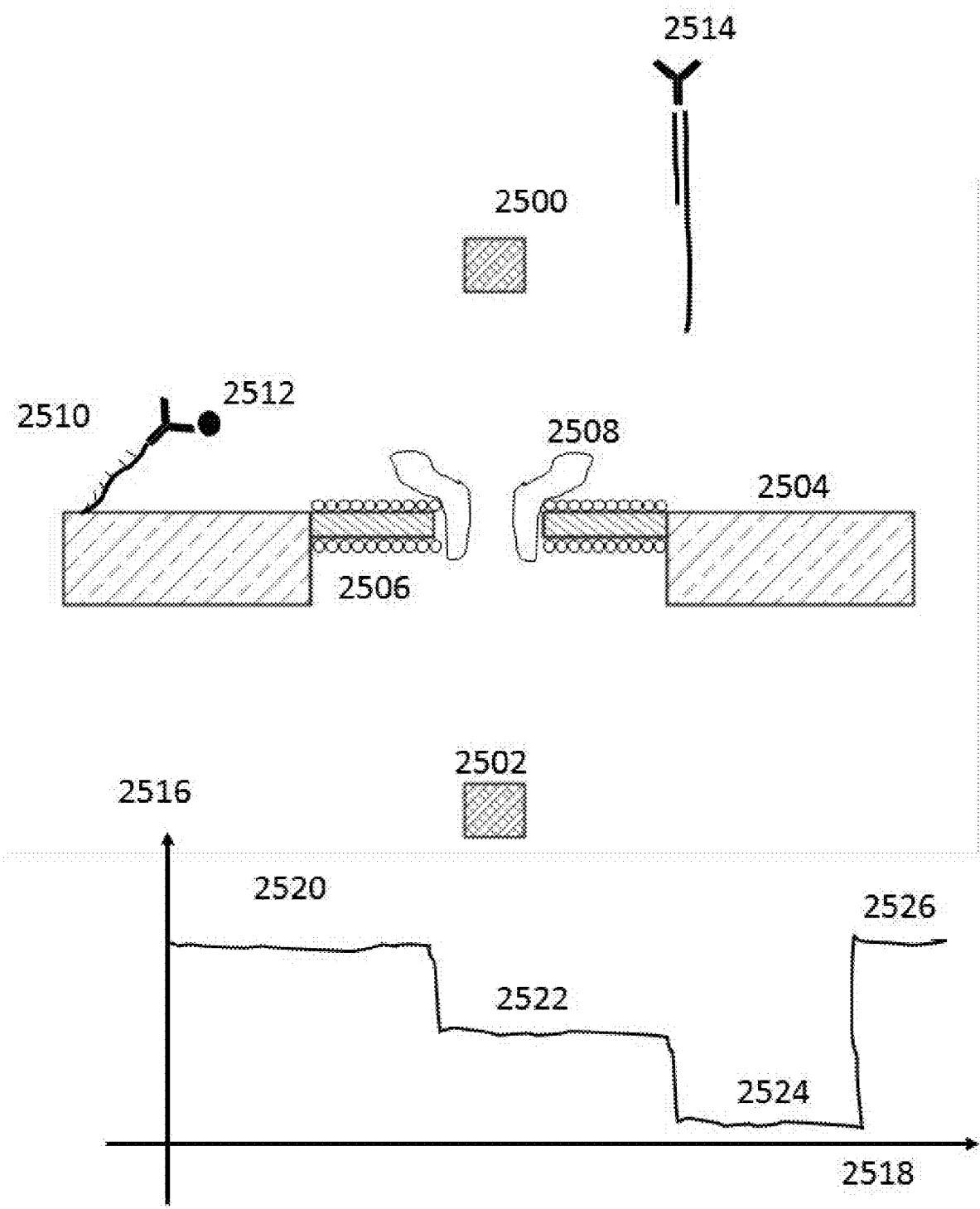

In this example, the detection probe comprises a binding molecule (e.g., antibody) bound to a nucleic acid comprising a single stranded region and a double stranded region. With reference to FIG. 25A, a plot of signal 2516 (e.g., current) versus time 2518 is shown. The current passing through the pore is relatively high 2520 when the pore is not obstructed by the detection probe. With reference to FIG. 25B, applying a first bias across the first electrode 2500 and the second electrode 2502 can cause the single stranded portion of the detection probe to pass into the pore and partially obstruct the pore, thereby decreasing the current 2522. At this first bias, the force exerted on the detection probe is not large enough to disrupt the bond between the detection probe 2514 and the antigen 2512. The length of the double stranded nucleic acid can be chosen such that when bound to the antigen, the double stranded portion of the detection probe does not extend into the pore. However, with reference to FIG. 25C, applying a second bias to the electrodes which is stronger than the first bias, can cause the detection probe to dissociate from the antigen and pass further into the pore. When located further in the pore, the double stranded nucleic acid portion of the detection probe can more fully obstruct the pore and thereby result in a further decrease in the signal 2524 (current). Following the sandwich assay described in this example, the polarity of the applied bias can be reversed, thereby resulting in ejection of the detection probe from the pore as shown in FIG. 25D and an increase in the signal 2516, for example to its initial state 2526.

Figure 26:
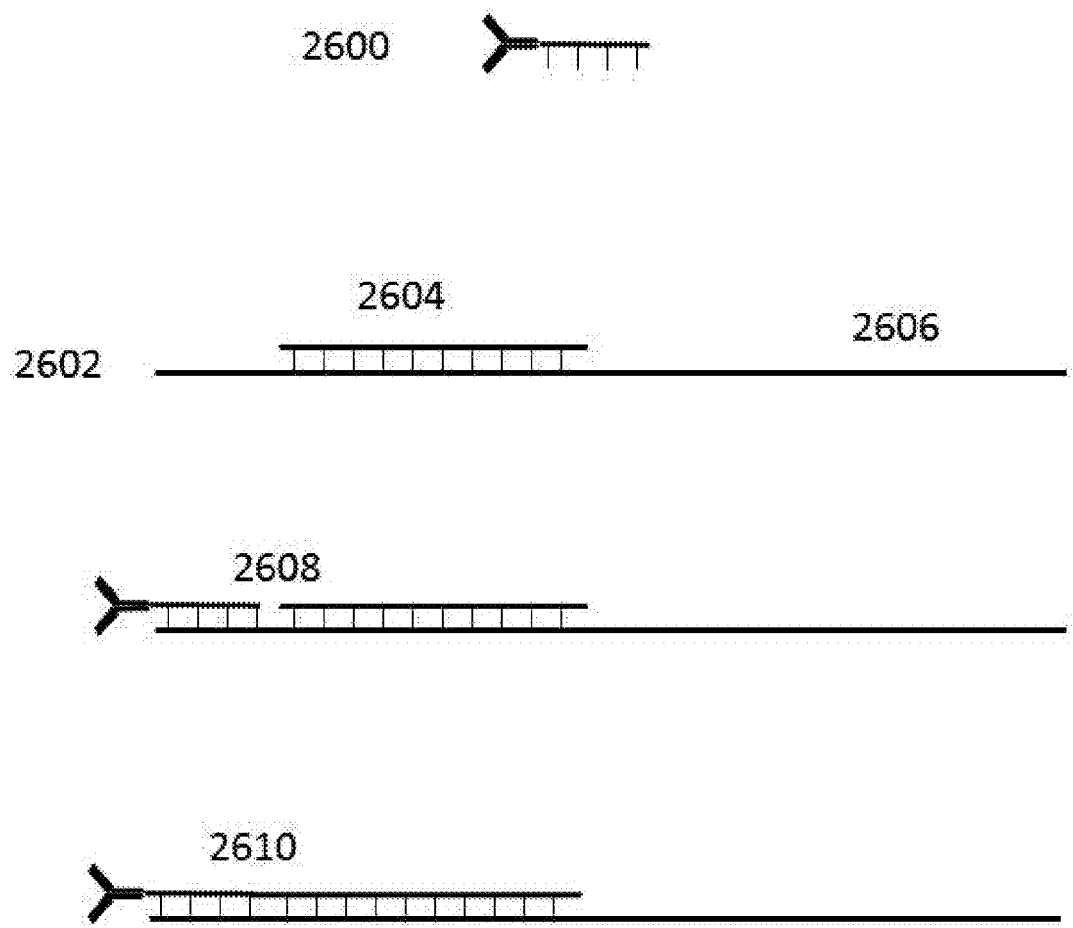
FIG. 26 shows an example of a method for producing a detection probe suitable for use in a nanopore.

As described herein, the bias can be increased over time to apply a greater and greater force on the detection probe. The force at which the signal decreases (e.g., from 2522 to 2544) can be used to differentiate between specific binding and non-specific of the antigen to the detection probe. In some cases, the methods and systems disclosed herein can be used to differentiate non-specific binding associated with false positive results from specific binding associated with true positive results Example 7: Synthesis of Detection Probes Example 6 describes a method for using a two-state detection probe that generates different signal levels depending on whether the detection probe partially blocks the pore or fully blocks the pore. The two-state detection probe can have any suitable composition. For example, the two-state detection probe can be an antibody conjugated to a nucleic acid molecule. To make such a detection probe, an oligonucleotide conjugated antibody 2600 can hybridize 2608 to a nucleic acid molecule 2602 having a single stranded portion 2606 and a double stranded portion 2604 as shown in FIG. 26. The hybridized molecules can be ligated 2610 to form the two-state detection probe.

Example 8: Binding Energy Analysis Using Oligonucleotide Arrays

Figure 27:
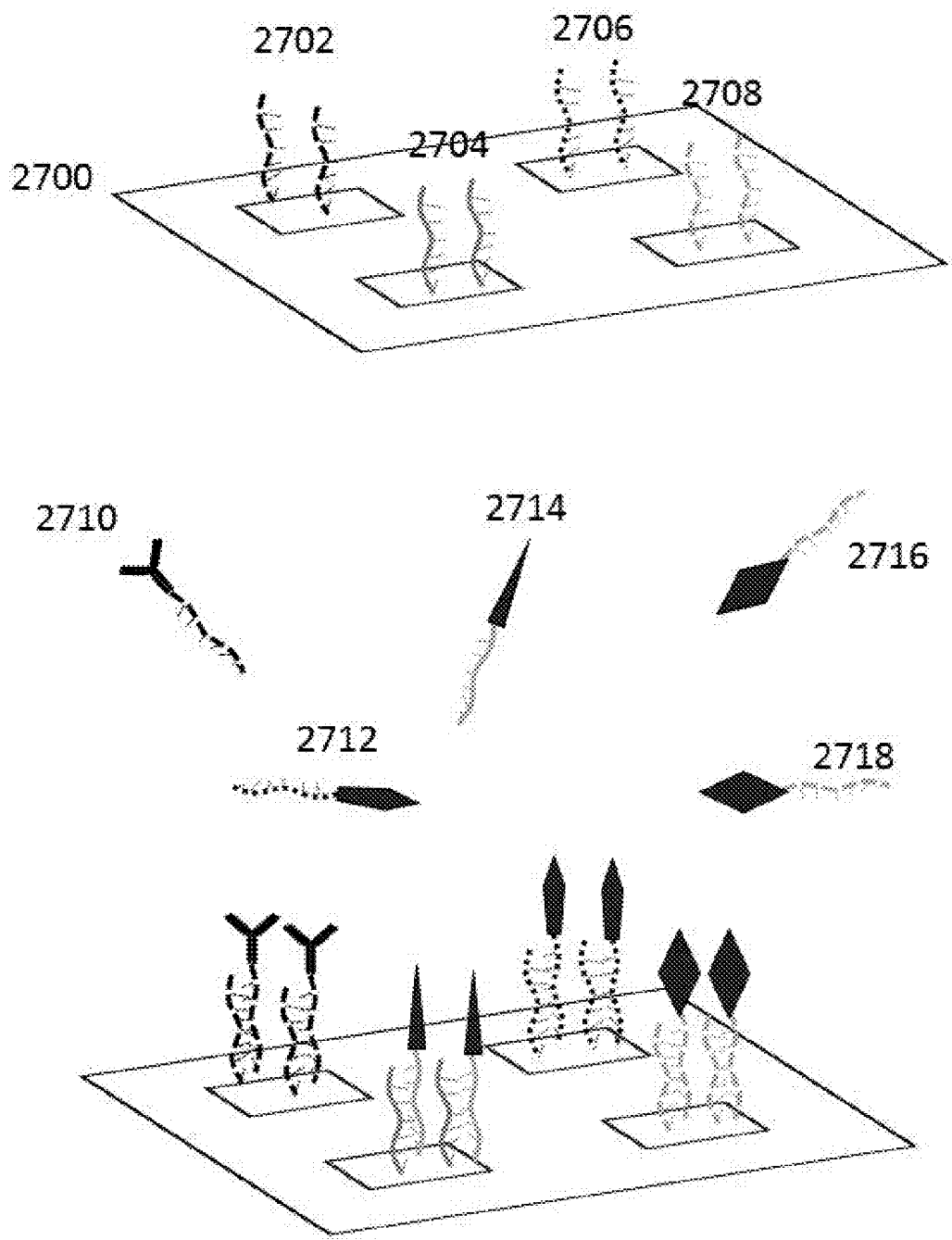
FIG. 27 shows an example of performing the methods of the present disclosure using an oligonucleotide array.

Systems and methods for making oligonucleotide arrays are known (e.g., using photolithography), for example as described in U.S. Pat. Nos. 5,831,070, 5,925,525, International Patent Application Publication No. WO2003100012 and International Patent Application Publication No. WO2003064699, each of which is incorporated herein by reference in its entirety. With reference to FIG. 27, a chip 2700 for binding energy analysis can comprise a plurality of integrated sensors. The sensors can have different types of oligonucleotide linkers attached in proximity to the sensors (i.e., 2702, 2704, 2706 and 2708). The oligonucleotide array can be transformed into a protein (e.g., antibody) array. Transforming an oligonucleotide array into a protein array can be accomplished, for example, by immobilizing a suite of complimentary proteins (i.e., 2710, 2712, 2714, 2716 and 2718) to the array. The proteins, for example, can be functionalized with nucleic acid sequences that are hybridizable to certain oligonucleotide linkers on the oligonucleotide array. The protein array can be used to perform a sandwich assay (e.g., to determine binding energy) as described herein.

Example 9: Binding Probe Conjugation

In some cases, insufficient yield of the PCR product using a hexanyl modified primer renders such methods impractical. This example describes the use a DIBO-maleimide linker molecule to couple a molecule to a surface. A linker molecule comprising a DIBO-Maleimide was reacted with PCR product containing thiol modification (i.e., rather than alkyne modification). The conjugate was purified using Agencourt Ampure XP magnetic beads.

To make the PCR product, a PCR reaction was performed with a 3'-thiol containing and a 5'-Cy5 modified primer to produce a 107 base pair (bp) product of approximately 130 kDa molecular weight. The PCR product was purified using a GeneJET PCR Purification Kit from ThermoFisher Scientific and quantified using a Nanodrop 1000. Antibody was activated by incubating with a 30:1 molar excess of DIBO-Maleimide overnight in the dark at room temperature.

Then, a DNA charge tag was conjugated to the antibody. Thiol-PCR-Cy5 product was incubated at room temperature for 30 minutes in 5 millimolar (mM) tris(2-carboxyethyl) phosphine (TCEP) immediately prior to conjugation. A 50 microliter (ul) aliquot of maleimide activated antibody (c.a. 100 micrograms (ug)) and 50 ul of PCR product (100 ug) were combined and the reaction proceeded at room temperature in a dark room for 72 hours.

The conjugated product was purified using DNA capture with Agencourt Ampure XP beads. A PCR column purification approach was used in parallel and gave similar yields. Conjugate yield and QC were performed. Protein concentration was determined for both the supernatant (unconjugated antibody) and the bead eluate (conjugated antibody).

About 39.5 micrograms (ug) of the original 100 ug was conjugated with DNA. About 42 ug of unconjugated antibody was found in the supernatant from the bead purification. This suggests that approximately 20 ug of antibody is lost during the conjugation process.

Example 10: Functional Testing

To perform functional testing, the following reagents were prepared: (a) monoclonal mouse anti-human IL8 antibody biotinylated using Siteclick chemistry; (b) monoclonal mouse anti-human IL8 antibody conjugated with succinimidyl 3-(2-pyridyldithio)propionate (SPDP); (c) SPDP conjugated NeutrAvidin; (d) polyclonal goat anti-human IL8 antibody with charge tag conjugated using Siteclick chemistry; (e) recombinant human IL8; (f) maleimide functionalized oxide coated chips; (g) maleimide functionalized force spectroscopy chips described herein; (h) blocking buffer: 0.5% BSA in 1×PBS; and (i) Alexa 647 conjugated rabbit anti-goat antibody for optical detection.

SPDP conjugated anti-IL8 antibody and SPDP conjugated NeutrAvidin were first spotted onto the chip surfaces via hand spotting or using a Scienion S3 spotter. The chips were then incubated in blocking solution (0.5% BSA in 1×PBS) for 1 hour. The chip surfaces were then incubated with 10 ug/ml concentration of biotinylated anti-IL8 antibody for 30 min. Following incubation, the chips were washed in PBS for 10 minutes. Next, the chips were incubated with antigen (recombinant human IL8, 1 ng/ml concentration) for 1 hr. Then, the chips were washed in PBS for 10 minutes. Following the wash, the chips were incubated with 1 ng/ml concentration polyclonal charge tag conjugated anti-IL8 detecting antibody. Then, the chips were washed in PBS for 10 minutes. Following the wash, the chip was incubated with 1 ng/ml concentration of Alexa modified antibody for 30 min. Then, the chips were washed in PBS for 10 minutes. The chip was examined by microscopy. Force spectroscopy was performed on the force spectroscopy chips (see Example 11).

Figure 30:
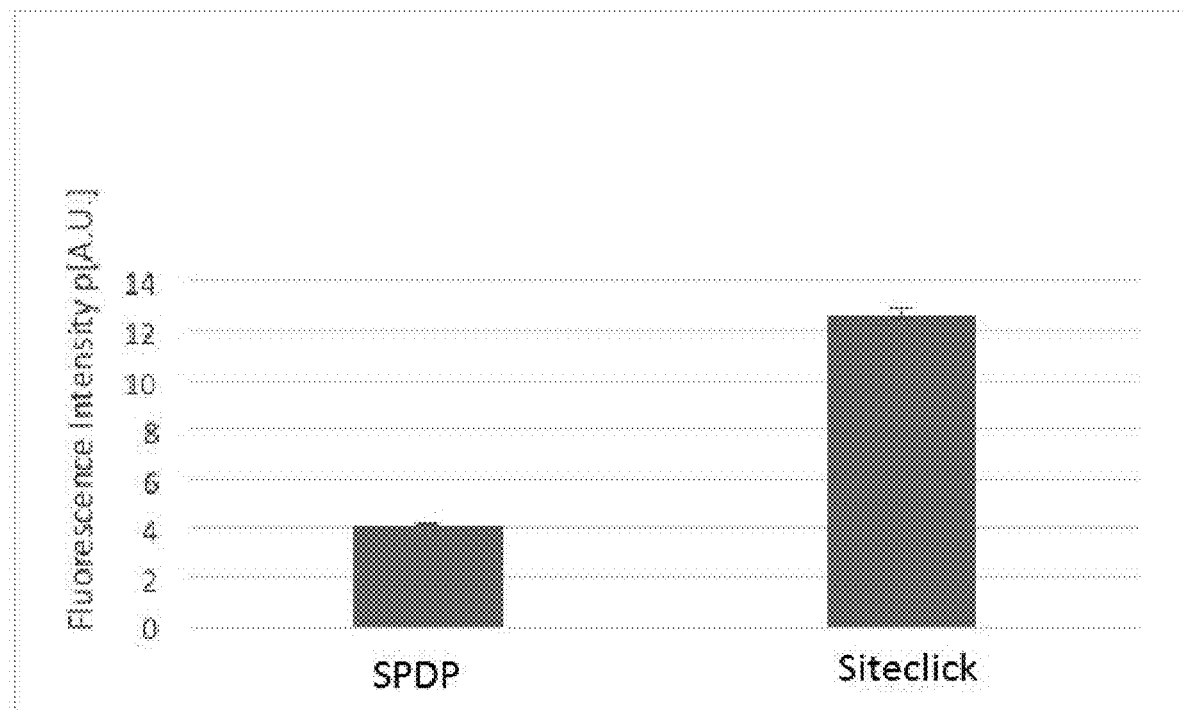
FIG. 30 shows an example of fluorescent signal achieved by two different linking methods.

The results from chip examination by microscopy are provided in FIG. 30. FIG. 30 shows a comparison of SPDP conjugated antibody capture (left) vs. Siteclick protocol described in Example 9 (i.e., SPDP conjugated NeutrAvidin+siteclick biotinylated antibody capture). A 3.1× increase was observed in optical signal level by using Siteclick vs. SPDP conjugation, suggesting that the density of active sites is significantly higher.

Example 11: Force Spectroscopy

Figure 31:
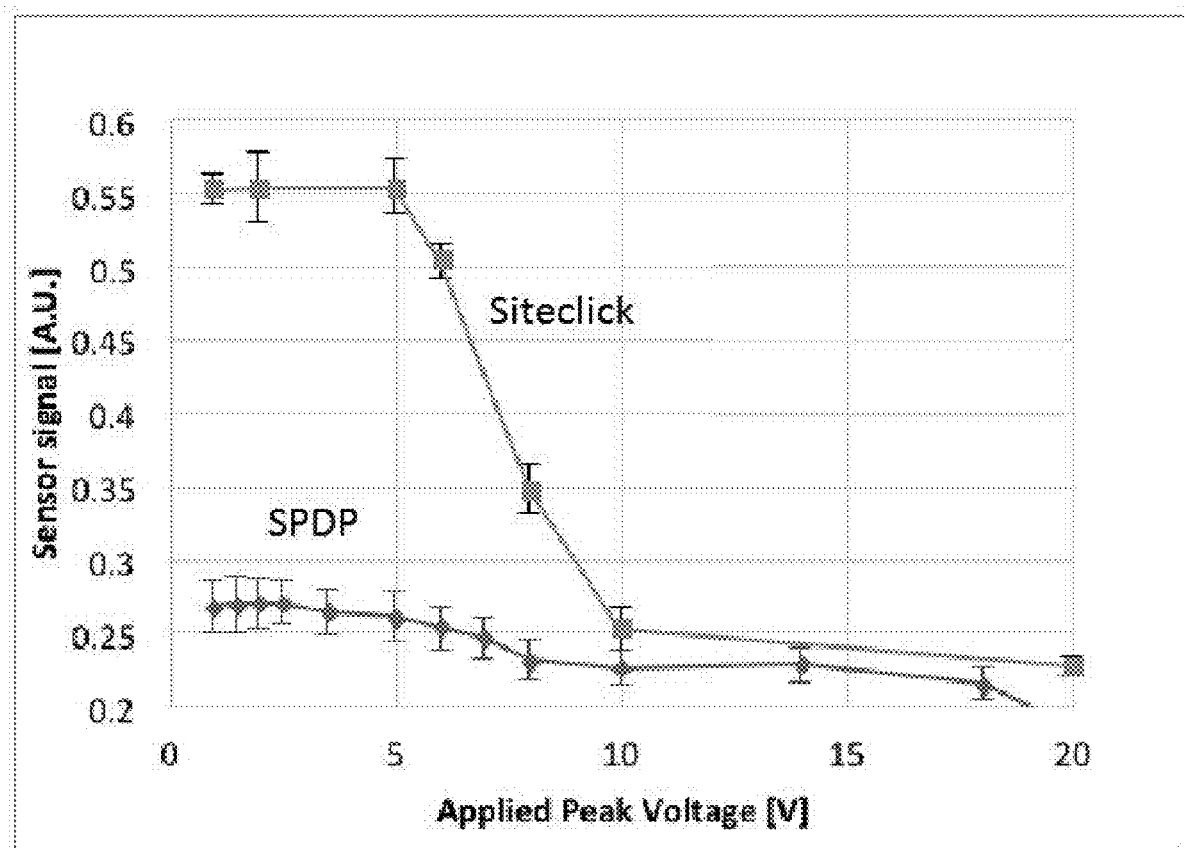
FIG. 31 shows an example of sensor signal as a function of applied peak voltage for two different capture antibody immobilization methods.

A force spectroscopy assay was performed using the reagents described in Example 9 and Example 10. The result from the force spectroscopy assay is shown in FIG. 31. Using Siteclick based reagents both significantly improved the signal level and reduced the noise level, yielding a cleaner experimental result. The experiments were not run simultaneously.

It should be understood from the foregoing that, while particular implementations have been illustrated and described, various modifications can be made thereto and are contemplated herein. For example, the embodiments described herein can be combined with or modified to yield yet more embodiments of the present invention. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for detecting a presence of a target analyte, comprising:
    a) activating at least one sensor comprising one or more surfaces between two or more electrodes, wherein the one or more surfaces comprise an electrically insulating layer, an electrically conducting layer, a bias stabilization layer, and two or more capture probes tethered to the surface;
    b) bringing the one or more surfaces in contact with a solution containing or suspected of containing the target analyte and a non-target analyte, under conditions sufficient to permit the target analyte and the non-target analyte to bind to at least one of the two or more capture probes;
    c) applying a first voltage across the two or more electrodes that is sufficient to release the non-target analyte, but not the target analyte, from at least one of the two or more capture probes;
    d) applying a second voltage across the two or more electrodes that is sufficient to release the target analyte from at least one of the two or more capture probes and
    e) detecting a signal indicative of a presence of the target analyte on the one or more surfaces.

2. The method of claim 1, wherein the signal is indicative of a binding energy of the target analyte on the one or more surfaces.

3. The method of claim 1, wherein the one or more surfaces comprise a field confining feature that concentrates an electric field to a strength of at least about $10^3$ volts per meter.

4. The method of claim 3, wherein the field confining feature comprises an orifice in the one or more surfaces.

5. The method of claim 1, wherein the two or more capture probes are nucleic acid molecules that hybridize with the target analyte.

6. The method of claim 5, wherein the target analyte is a nucleic acid molecule.

7. The method of claim 1, wherein the two or more capture probes comprise antibodies that bind the target analyte.

8. The method of claim 7, wherein the target analyte is a protein.

9. The method of claim 1, wherein the target analyte is a charged analyte.

10. The method of claim 1, wherein the first voltage is sufficient to exert an applied force of at least about 1 piconewton (pN) on the non-target analyte.

11. The method of claim 10, wherein the applied force is less than a binding force of the target analyte bound to the at least one of the two or more capture probes.

12. The method of claim 1, wherein the first voltage is less than the second voltage.

13. The method of claim 1, wherein the first voltage and the second voltage are individual voltages of a continuously applied voltage that is changed over time.

14. The method of claim 1, wherein the second voltage is applied without washing the one or more surfaces after applying the first voltage.

15. The method of claim 1, further comprising monitoring a signal indicative of the presence of the target analyte on the one or more surfaces as the applied voltage is varied over time.

16. The method of claim 1, wherein the solution comprises charge-labeled antibodies that bind with the target analyte.

17. The method of claim 1, wherein the signal indicative of the presence of the target analyte on the one or more surfaces is detected by measuring an optical signal associated with the target analyte.

18. The method of claim 17, wherein the optical signal is a fluorescence signal.

19. The method of claim 1, wherein the electrically conducting layer is electrically isolated from the solution.

* * * * *